US007622453B2

(12) United States Patent
Frieden et al.

(10) Patent No.: US 7,622,453 B2
(45) Date of Patent: Nov. 24, 2009

(54) OLIGOMERIC COMPOUNDS FOR THE MODULATION OF BCL-2

(75) Inventors: Miriam Frieden, Kobenhavn N (DK); Jens B. Hansen, Vaerlose (DK); Henrik Orum, Vaerlose (DK); Majken Westergaard, Birkerod (DK); Charlotte A. Thrue, Residence Not Provided (DK)

(73) Assignee: Santaris Pharma A/S, Horsholm ( * ) Notice: Subject to any disclaimer, the term of this patent is extended or adjusted under 35 U.S.C. 154(b) by 320 days.

(21) Appl. No.: 11/021,729

(22) Filed: Dec. 23, 2004

(65) Prior Publication Data
US 2005/0203042 A1 Sep. 15, 2005

Related U.S. Application Data

(60) Provisional application No. 60/621,594, filed on Oct. 22, 2004, provisional application No. 60/586,340, filed on Jul. 7, 2004, provisional application No. 60/558,392, filed on Mar. 31, 2004, provisional application No. 60/532,844, filed on Dec. 23, 2003.

(30) Foreign Application Priority Data

| Dec. 23, 2003 | (DK) | ................. | 2003 01929 |
| Mar. 31, 2004 | (DK) | ................. | 2004 00517 |
| Jul. 7, 2004 | (DK) | ................. | 2004 01069 |
| Oct. 22, 2004 | (DK) | ................. | 2004 01629 |

(51) Int. Cl.
A01N 61/00 (2006.01)
A01N 43/04 (2006.01)
C12Q 1/68 (2006.01)
C07H 21/02 (2006.01)
C07H 21/04 (2006.01)

(52) U.S. Cl. ............................ 514/44; 435/6; 435/91.1; 435/91.31; 435/455; 514/1; 514/2; 536/23.1; 536/24.5

(58) Field of Classification Search ...................... 435/6, 435/91.1, 91.31, 455, 458; 536/23.1, 24.5; 514/44, 1, 2
See application file for complete search history.

(56) References Cited

U.S. PATENT DOCUMENTS

| 5,108,921 | A | | 4/1992 | Low et al. |
| 5,227,400 | A | | 7/1993 | Holton et al. |
| 5,248,796 | A | | 9/1993 | Chen et al. |
| 5,250,683 | A | | 10/1993 | Holton et al. |
| 5,254,580 | A | | 10/1993 | Chen et al. |
| 5,272,171 | A | | 12/1993 | Ueda et al. |
| 5,278,324 | A | | 1/1994 | Kingston et al. |
| 6,040,181 | A | * | 3/2000 | Reed ............................ 435/377 |
| 6,133,246 | A | * | 10/2000 | McKay et al. ................. 514/44 |
| 6,794,499 | B2 | * | 9/2004 | Wengel et al. ............. 536/23.1 |

FOREIGN PATENT DOCUMENTS

| EP | 0 253 739 B1 | 10/1989 |
| WO | WO 92/09589 | 6/1992 |
| WO | WO 93/18210 | 9/1993 |
| WO | WO 95/08350 | 3/1995 |
| WO | WO 99/14226 | 3/1999 |
| WO | WO 00/56746 | 9/2000 |
| WO | WO 00/56748 | 9/2000 |
| WO | WO 00/66604 | 11/2000 |
| WO | WO 01/25248 A2 | 4/2001 |
| WO | WO 02/28875 A2 | 4/2002 |
| WO | WO 02/094250 A2 | 11/2002 |
| WO | WO 03/006475 A2 | 1/2003 |
| WO | WO 03/070969 A2 | 8/2003 |
| WO | WO 03/095467 | 11/2003 |
| WO | WO 2004 046160 A2 | 6/2004 |

OTHER PUBLICATIONS

Opalinska, J.B. et al., Nature Rev., vol. 1, pp. 503-514 (2002).*
Chirila, T.V. et al., Biomaterials, vol. 23, pp. 321-342 (2002).*
Peracchi, A., Rev. Med. Virol., vol. 14, pp. 47-64 (2004).*
Agrawal, S. et al., Molecular Med. Today, vol. 6, pp. 72-81 (2000).*
Branch, A.D., Trends in Biochem. Sci., vol. 23, pp. 45-50 (1998).*
Zangemeister-Wittke, Uwe et al., "Antisense to Apoptosis Inhibitors Facilitates Chemotherapy and TRAIL-Induced Death Signaling," Annals New York Academy of Sciences, 1002:90-94(2003). doi: 10.1196/annals.1281.019, XP008035613.
Zangemeister-Wittke, Uwe of al., "A Novel Bispecific Antisense Oligonucleotide Inhibiting Both bcl-2 and bcl-xL Expression Efficiently Induces Apoptosis in Tumor Cells," Clinical Cancer Research, vol. 6, 2547-2555, Jun. 2000, XP-002241562.
Mologni, Luca et al, "In Vitro Transcriptional and Translational Block of the bcl-2 Gene Operated by Peptide Nucleic Acid." Biochemical and Biophysical Research Communications, 264. 537-543(1999), Article ID bbrc. 1999.1548, 0006-291X/99.
Klasa, Richard J. et al., "Oblimersen Bcl-2 Antisense: Facilitating Apoptosis in Anticancer Treatment." Antisense & Nucleic Acid Drug Development, 12:193-213 (2002), Mary Ann Liebert, Inc.
Jepsen, Jan Stenvang, Ph.D. Thesis, "Locked Nucleic Acid (LNA) as cancer-therapeutic agent," Department of Tumor Endocrinology Institute of Cancer Biology Danish Cancer Society & University of Copenhagen, May 2003.

(Continued)

Primary Examiner—Jane Zara
(74) Attorney, Agent, or Firm—Fish & Richardson P.C.

(57) ABSTRACT

The present invention provides improved oligomeric compound, in particular oligonucleotide compounds, and methods for modulating the expression of the Bcl-2 gene in humans. In particular, this invention relates to oligomeric compounds of 10-30 nucleobases in length which comprise a target binding domain that is specifically hybridizable to a region ranging from base position No. 1459 (5') to No. 1476 (3') of the human Bcl-2 mRNA, said target binding domain having the formula: 5'-[(DNA/RNA)$_{0-1}$-(LNA/LNA*)$_{2-7}$-(DNA/RNA/LNA*)$_{4-14}$-(LNA/LNA*)$_{2-7}$-(DNA/RNA)$_{0-1}$]-3' and said target binding domain comprising at least two LNA nucleotides or LNA analogue nucleotides linked by a phosphorothioate group (—O—P(O,S)—O—). In particular the oligo is predominantly or fully thiolated. The invention also provides the use of such oligomers or conjugates or chimera for the treatment of various diseases associated with the expression of the Bcl-2 gene, such as cancer.

57 Claims, 20 Drawing Sheets

OTHER PUBLICATIONS

Frieden, Miriam et al., "Expanding the design horizon of antisense oligonucleotides with alpha-,-LNA," Nucleic Acids Research, vol. 31, No. 21, 6365-6372, 2003, Oxford University Press, DOI: 10.1093/nar/gkg820.

Fluiter, Kees et al., "In vivo tumor growth inhibition and biodistribution studies of locked nucleic acid (LNA) antisense oligonucleotides," Nucleic Acids Research. vol. 31. No. 3, 953-962, 2003, Oxford University Press, DOI: 10.1093/nar/gkg185.

Freier, Susan M. et al., "The ups and downs of nucleic acid duplex stability: structure-stability studies on chemically-modified DNA:RNA duplexes," Nucleic Acids Research, vol. 25, No. 22, 4429-4443,1997, Oxford University Press.

Uhlmann, Eugen, "Recent advances in the medicinal chemistry of antisense oligonucleotides," Current Opinion in Drug Discovery & Development, vol. 3. No. 2, 203-213, 2000, PharmaPress Ltd., ISSN 1367-6733.

Soutschek, Jürgen et al., "Therapeutic silencing of an endogenous gene by systemic administration of modified siRNAs," Nature, vol. 432, 173-178, Nov. 11, 2004, Nature Publishing Group.

Beaucage, Serge L. et al., "The Synthesis of Modified Oligonucleotides by the Phosphoramidite Approach and Their Applications," Tetrahedron Report No. 335, vol. 49. No. 28, 6123-6194, 1993. Great Britain. 0040-4020/93, Pergamon Press Ltd.

Beaucage, Serge L. et al., "Advances in the Synthesis of Oligonucleotides by the Phosphoramidite Approach," Tetrahedron Report No. 309, vol. 48. No. 12, 2223-2311, 1992, Great Britain, 0040-4020/92, Pergamon Press Ltd.

Wagner, Ernst et al., "Transferrin-polycation conjugates as carriers for DNA uptake into cells," Proc. Natl. Acad. Sci. USA, vol. 87, 3410-3414, May 1990, Biochemistry.

Leamon, Christopher P. et al., "Delivery of macromolecules into living cells: A method that exploits folate receptor endocytosis," Proc. Natl. Acad. Sci. USA, vol. 88, 5572-5576, Jul. 1991, Cell Biology.

Holton, Robert et al., "First Total Synthesis of Taxol. 1. Functionalization of the B Ring," J. Am. Chem. Soc. 1994, 116, 1597-1598, 002-7863/94/1516-1597, American Chemical Society.

Nicolaou, K. C. et al., "Total synthesis of taxol," Nature, Letters to Nature. vol. 367, Feb. 17, 1994, 630-634.

McGuire. William P., "Taxol: A Unique Antineoplastic Agent with Significant Activity in Advanced Ovarian Epithelial Neoplasms," Annals of Internal Medicine, vol. 111, No. 4, Aug. 15, 1989.

Holmes, Frankie Ann et al., "Phase II Trial of Taxol. an Active Drug in the Treatment of Metastatic Breast Cancer," Journal of the National Cancer Institute, Articles, vol. 83, No. 24, Dec. 18, 1991, 1797-1805.

Kohn, Elise C. et al., "Dose-Intense Taxol: High Response Rate in Patients with Platinum-Resistant Recurrent Ovarian Cancer," Journal of the National Cancer Institute, Articles, vol. 86. No. 1, Jan. 5, 1994, 18-24.

Dass, Crispin R., "Vehicles for oligonucleotide delivery to tumors," Journal of Pharmacy and Pharmacology, 2002, 54:3-27, Review Article, ISSN 0022-3573.

Pedersen, Daniel Sejer et al., "Preparation of LNA Phosphoramidites," Synthesis, 2002, No. 6, 29 04 2002, 802-808, Article Identifier: 1437-210X,E ;2002,0,06,0802,0808,ftx,en; C00402SS.pdf, Georg Thieme Verlag Stuttgart, New York, ISSN 0039-7881.

Sørensen, Mads D. et al., α-L-*ribo*-Configured Locked Nucleic Add (α-L-LNA): Synthesis and Properties, J. Am. Chem. Soc., vol. 124, No. 10, 2002, 2164-2176, 2002 American Chemical Society, 10.102/ja0168763.

Singh, Sanjay K. et al., "Synthesis of Novel Bicyclo[2.2.1] Ribonucleosides: 2'-Amino- and 2'-Thio-LNA Monomeric Nucleosides," The Journal of Organic Chemistry, vol. 63, No. 18, 6078-6079, 1998 American Chemical Society, S0022-3263(98)00665-3.

Rosenbolhm, Christoph et al., Synthesis of 2'-amino-LNA: a new strategy, Org. Biomol. Chem, 2003, 1, 655-663, The Royal Society of Chemistry 2003, DOI: 10.1039/b208864a.

Pedersen, Daniel Sejer et al., "Analogues of LNA (Locked Nucleic Acid): Synthesis of the 2'-Thio-LNA Ribothymidine and 5-Methylcytidine Phosphoramidites," SYNTHESIS, 2004, No. 4. pp. 0578-0582, DOI: 10.1055/s-2004-815959, Art ID: T10403SS, Georg Thieme Verlag Stuttgart. New York.

Pfundheller, Henrik M. et al., "Locked Nucleic Acid Synthesis," Methods in Molecular Biology, vol. 228, 127-145, Edited by: Herdewijn P., Oligonucleotide Synthesis Methods and Applications, Humana Press 2005.

Wahlestedt et al., "Potent and nontoxic antisense oligonucleotides containing locked nucleic acids" Proc. Nat'l. Acad. Sci. USA 97(10):5633-5638, 2000.

\* cited by examiner

SEQUENCE LISTING

<160> NUMBER OF SEQ ID NOS: 65

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: LNA modified nucleotide
<220> FEATURE:
<221> NAME/KEY: misc_feature
<222> LOCATION: (2)
<223> OTHER INFORMATION: 5-methyl cytosine
<220> FEATURE:
<221> NAME/KEY: misc_feature
<222> LOCATION: (16)
<223> OTHER INFORMATION: 5-methyl cytosine
<220> FEATURE:
<221> NAME/KEY: misc_feature
<222> LOCATION: (17)
<223> OTHER INFORMATION: LNA modified nucleotide
<220> FEATURE:
<221> NAME/KEY: misc_feature
<222> LOCATION: (1)..(18)
<223> OTHER INFORMATION: Phosphorothioate linkage

<400> SEQUENCE: 1
tctcccagcg tgcgccat                                                 18

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: LNA modified nucleotide
<220> FEATURE:
<221> NAME/KEY: misc_feature
<222> LOCATION: (2)
<223> OTHER INFORMATION: 5-methyl cytosine
<220> FEATURE:
<221> NAME/KEY: misc_feature
<222> LOCATION: (3)
<223> OTHER INFORMATION: LNA modified nucleotide
<220> FEATURE:
<221> NAME/KEY: misc_feature
<222> LOCATION: (15)..(16)
<223> OTHER INFORMATION: 5-methyl cytosine
<220> FEATURE:
<221> NAME/KEY: misc_feature
<222> LOCATION: (17)
<223> OTHER INFORMATION: LNA modified nucleotide
<220> FEATURE:
<221> NAME/KEY: misc_feature
<222> LOCATION: (1)..(18)
<223> OTHER INFORMATION: Phosphorothioate linkage

<400> SEQUENCE: 2
tctcccagcg tgcgccat                                                 18

<210> SEQ ID NO 3
<211> LENGTH: 18
<212> TYPE: DNA
<213> ORGANISM: Artificial Sequence -continued

```
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: LNA modified nucleotide
<220> FEATURE:
<221> NAME/KEY: misc_feature
<222> LOCATION: (2)
<223> OTHER INFORMATION: 5-methyl cytosine
<220> FEATURE:
<221> NAME/KEY: misc_feature
<222> LOCATION: (3)
<223> OTHER INFORMATION: LNA modified nucleotide
<220> FEATURE:
<221> NAME/KEY: misc_feature
<222> LOCATION: (4)
<223> OTHER INFORMATION: 5-methyl cytosine
<220> FEATURE:
<221> NAME/KEY: misc_feature
<222> LOCATION: (14)
<223> OTHER INFORMATION: LNA modified nucleotide
<220> FEATURE:
<221> NAME/KEY: misc_feature
<222> LOCATION: (15)..(16)
<223> OTHER INFORMATION: 5-methyl cytosine
<220> FEATURE:
<221> NAME/KEY: misc_feature
<222> LOCATION: (17)
<223> OTHER INFORMATION: LNA modified nucleotide
<220> FEATURE:
<221> NAME/KEY: misc_feature
<222> LOCATION: (1)..(18)
<223> OTHER INFORMATION: Phosphorothioate linkage

<400> SEQUENCE: 3
tctcccagcg tgcgccat                                                 18

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (2)
<223> OTHER INFORMATION: 5-methyl cytosine
<220> FEATURE:
<221> NAME/KEY: misc_feature
<222> LOCATION: (3)
<223> OTHER INFORMATION: LNA modified nucleotide
<220> FEATURE:
<221> NAME/KEY: misc_feature
<222> LOCATION: (4)
<223> OTHER INFORMATION: 5-methyl cytosine
<220> FEATURE:
<221> NAME/KEY: misc_feature
<222> LOCATION: (15)..(16)
<223> OTHER INFORMATION: 5-methyl cytosine
<220> FEATURE:
<221> NAME/KEY: misc_feature
<222> LOCATION: (17)
<223> OTHER INFORMATION: LNA modified nucleotide
<220> FEATURE:
<221> NAME/KEY: misc_feature
<222> LOCATION: (1)..(18)
<223> OTHER INFORMATION: Phosphorothioate linkage

<400> SEQUENCE: 4
tctcccagcg tgcgccat                                                 18

<210> SEQ ID NO 5
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: LNA modified nucleotide
<220> FEATURE:
<221> NAME/KEY: misc_feature
<222> LOCATION: (2)
<223> OTHER INFORMATION: 5-methyl cytosine
<220> FEATURE:
<221> NAME/KEY: misc_feature
<222> LOCATION: (3)
<223> OTHER INFORMATION: LNA modified nucleotide
<220> FEATURE:
<221> NAME/KEY: misc_feature
<222> LOCATION: (15)..(16)
<223> OTHER INFORMATION: 5-methyl cytosine
<220> FEATURE:
<221> NAME/KEY: misc_feature
<222> LOCATION: (17)..(18)
<223> OTHER INFORMATION: LNA modified nucleotide
<220> FEATURE:
<221> NAME/KEY: misc_feature
<222> LOCATION: (1)..(18)
<223> OTHER INFORMATION: Phosphorothioate linkage

<400> SEQUENCE: 5
tctcccagcg tgcgccat                                                    18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: modified alpha-L-LNA nucleotide
<220> FEATURE:
<221> NAME/KEY: misc_feature
<222> LOCATION: (2)
<223> OTHER INFORMATION: 5-methyl cytosine
<220> FEATURE:
<221> NAME/KEY: misc_feature
<222> LOCATION: (3)
<223> OTHER INFORMATION: modified alpha-L-LNA nucleotide
<220> FEATURE:
<221> NAME/KEY: misc_feature
<222> LOCATION: (15)..(16)
<223> OTHER INFORMATION: 5-methyl cytosine
<220> FEATURE:
<221> NAME/KEY: misc_feature
<222> LOCATION: (17)
<223> OTHER INFORMATION: modified alpha-L-LNA nucleotide
<220> FEATURE:
<221> NAME/KEY: misc_feature
<222> LOCATION: (1)..(18)
<223> OTHER INFORMATION: Phosphorothioate linkage

<400> SEQUENCE: 6
tctcccagcg tgcgccat                                                    18

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
```

-continued oligonucleotide
<220> FEATURE:
<221> NAME/KEY: misc_feature
<222> LOCATION: (2)
<223> OTHER INFORMATION: 5-methyl cytosine
<220> FEATURE:
<221> NAME/KEY: misc_feature
<222> LOCATION: (3)
<223> OTHER INFORMATION: modified alpha-L-LNA nucleotide
<220> FEATURE:
<221> NAME/KEY: misc_feature
<222> LOCATION: (4)
<223> OTHER INFORMATION: 5-methyl cytosine
<220> FEATURE:
<221> NAME/KEY: misc_feature
<222> LOCATION: (15)..(16)
<223> OTHER INFORMATION: 5-methyl cytosine
<220> FEATURE:
<221> NAME/KEY: misc_feature
<222> LOCATION: (17)
<223> OTHER INFORMATION: modified alpha-L-LNA nucleotide
<220> FEATURE:
<221> NAME/KEY: misc_feature
<222> LOCATION: (1)..(18)
<223> OTHER INFORMATION: Phosphorothioate linkage

<400> SEQUENCE: 7
tctcccagcg tgcgccat                                                18

<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: 5-methyl cytosine
<220> FEATURE:
<221> NAME/KEY: misc_feature
<222> LOCATION: (2)
<223> OTHER INFORMATION: modified LNA nucleotide
<220> FEATURE:
<221> NAME/KEY: misc_feature
<222> LOCATION: (14)..(15)
<223> OTHER INFORMATION: 5-methyl cytosine
<220> FEATURE:
<221> NAME/KEY: misc_feature
<222> LOCATION: (1)..(16)
<223> OTHER INFORMATION: Phosphorothioate linkage

<400> SEQUENCE: 8
ctcccagcgt gcgcca                                                  16

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: 5-methyl cytosine
<220> FEATURE:
<221> NAME/KEY: misc_feature
<222> LOCATION: (2)
<223> OTHER INFORMATION: modified alpha-L-LNA nucleotide
<220> FEATURE:
<221> NAME/KEY: misc_feature
<222> LOCATION: (14)..(15)
<223> OTHER INFORMATION: 5-methyl cytosine

```
<220> FEATURE:
<221> NAME/KEY: misc_feature
<222> LOCATION: (1)..(16)
<223> OTHER INFORMATION: Phosphorothioate linkage

<400> SEQUENCE: 9
ctcccagcgt gcgcca                                                     16

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: 5-methyl cytosine
<220> FEATURE:
<221> NAME/KEY: misc_feature
<222> LOCATION: (2)
<223> OTHER INFORMATION: modified LNA nucleotide
<220> FEATURE:
<221> NAME/KEY: misc_feature
<222> LOCATION: (14)..(15)
<223> OTHER INFORMATION: 5-methyl cytosine
<220> FEATURE:
<221> NAME/KEY: misc_feature
<222> LOCATION: (16)
<223> OTHER INFORMATION: modified LNA nucleotide
<220> FEATURE:
<221> NAME/KEY: misc_feature
<222> LOCATION: (1)..(16)
<223> OTHER INFORMATION: Phosphorothioate linkage

<400> SEQUENCE: 10
ctcccagcgt gcgcca                                                     16

<210> SEQ ID NO 11
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: 5-methyl cytosine
<220> FEATURE:
<221> NAME/KEY: misc_feature
<222> LOCATION: (2)
<223> OTHER INFORMATION: modified LNA nucleotide
<220> FEATURE:
<221> NAME/KEY: misc_feature
<222> LOCATION: (15)
<223> OTHER INFORMATION: 5-methyl cytosine
<220> FEATURE:
<221> NAME/KEY: misc_feature
<222> LOCATION: (16)
<223> OTHER INFORMATION: modified LNA nucleotide
<220> FEATURE:
<221> NAME/KEY: misc_feature
<222> LOCATION: (1)..(16)
<223> OTHER INFORMATION: Phosphorothioate linkage

<400> SEQUENCE: 11
ctcccagcgt gcgcca                                                     16

<210> SEQ ID NO 12
<211> LENGTH: 16
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: 5-methyl cytosine
<220> FEATURE:
<221> NAME/KEY: misc_feature
<222> LOCATION: (2)
<223> OTHER INFORMATION: modified LNA nucleotide
<220> FEATURE:
<221> NAME/KEY: misc_feature
<222> LOCATION: (3)
<223> OTHER INFORMATION: 5-methyl cytosine
<220> FEATURE:
<221> NAME/KEY: misc_feature
<222> LOCATION: (13)
<223> OTHER INFORMATION: modified LNA nucleotide
<220> FEATURE:
<221> NAME/KEY: misc_feature
<222> LOCATION: (14)..(15)
<223> OTHER INFORMATION: 5-methyl cytosine
<220> FEATURE:
<221> NAME/KEY: misc_feature
<222> LOCATION: (1)..(16)
<223> OTHER INFORMATION: Phosphorothioate linkage

<400> SEQUENCE: 12
ctcccagcgt gcgcca                                                        16

<210> SEQ ID NO 13
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: 5-methyl cytosine
<220> FEATURE:
<221> NAME/KEY: misc_feature
<222> LOCATION: (2)
<223> OTHER INFORMATION: modified LNA nucleotide
<220> FEATURE:
<221> NAME/KEY: misc_feature
<222> LOCATION: (3)..(4)
<223> OTHER INFORMATION: 5-methyl cytosine
<220> FEATURE:
<221> NAME/KEY: misc_feature
<222> LOCATION: (12)
<223> OTHER INFORMATION: 5-methyl cytosine
<220> FEATURE:
<221> NAME/KEY: misc_feature
<222> LOCATION: (13)
<223> OTHER INFORMATION: modified LNA nucleotide
<220> FEATURE:
<221> NAME/KEY: misc_feature
<222> LOCATION: (14)..(15)
<223> OTHER INFORMATION: 5-methyl cytosine
<220> FEATURE:
<221> NAME/KEY: misc_feature
<222> LOCATION: (1)..(16)
<223> OTHER INFORMATION: Phosphorothioate linkage

<400> SEQUENCE: 13
ctcccagcgt gcgcca                                                        16

<210> SEQ ID NO 14
<211> LENGTH: 16
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: 5-methyl cytosine
<220> FEATURE:
<221> NAME/KEY: misc_feature
<222> LOCATION: (2)
<223> OTHER INFORMATION: modified LNA nucleotide
<220> FEATURE:
<221> NAME/KEY: misc_feature
<222> LOCATION: (3)
<223> OTHER INFORMATION: 5-methyl cytosine
<220> FEATURE:
<221> NAME/KEY: misc_feature
<222> LOCATION: (13)
<223> OTHER INFORMATION: modified LNA nucleotide
<220> FEATURE:
<221> NAME/KEY: misc_feature
<222> LOCATION: (14)..(15)
<223> OTHER INFORMATION: 5-methyl cytosine
<220> FEATURE:
<221> NAME/KEY: misc_feature
<222> LOCATION: (16)
<223> OTHER INFORMATION: modified LNA nucleotide
<220> FEATURE:
<221> NAME/KEY: misc_feature
<222> LOCATION: (1)..(16)
<223> OTHER INFORMATION: Phosphorothioate linkage

<400> SEQUENCE: 14
ctcccagcgt gcgcca                                                    16

<210> SEQ ID NO 15
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: 5-methyl cytosine
<220> FEATURE:
<221> NAME/KEY: misc_feature
<222> LOCATION: (2)
<223> OTHER INFORMATION: modified LNA nucleotide
<220> FEATURE:
<221> NAME/KEY: misc_feature
<222> LOCATION: (14)..(15)
<223> OTHER INFORMATION: 5-methyl cytosine
<220> FEATURE:
<221> NAME/KEY: misc_feature
<222> LOCATION: (1)..(16)
<223> OTHER INFORMATION: Phosphorothioate linkage

<400> SEQUENCE: 15
ctcccaacgt gcgcca                                                    16

<210> SEQ ID NO 16
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: 5-methyl cytosine
<220> FEATURE:
<221> NAME/KEY: misc_feature
```

```
<222> LOCATION: (2)
<223> OTHER INFORMATION: modified alpha-L-LNA nucleotide
<220> FEATURE:
<221> NAME/KEY: misc_feature
<222> LOCATION: (14)..(15)
<223> OTHER INFORMATION: 5-methyl cytosine
<220> FEATURE:
<221> NAME/KEY: misc_feature
<222> LOCATION: (1)..(16)
<223> OTHER INFORMATION: Phosphorothioate linkage

<400> SEQUENCE: 16
ctcccaacgt gcgcca                                                       16

<210> SEQ ID NO 17
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: 5-methyl cytosine
<220> FEATURE:
<221> NAME/KEY: misc_feature
<222> LOCATION: (2)
<223> OTHER INFORMATION: modified LNA nucleotide
<220> FEATURE:
<221> NAME/KEY: misc_feature
<222> LOCATION: (3)
<223> OTHER INFORMATION: 5-methyl cytosine
<220> FEATURE:
<221> NAME/KEY: misc_feature
<222> LOCATION: (13)
<223> OTHER INFORMATION: modified LNA nucleotide
<220> FEATURE:
<221> NAME/KEY: misc_feature
<222> LOCATION: (14)..(15)
<223> OTHER INFORMATION: 5-methyl cytosine
<220> FEATURE:
<221> NAME/KEY: misc_feature
<222> LOCATION: (1)..(16)
<223> OTHER INFORMATION: Phosphorothioate linkage

<400> SEQUENCE: 17
ctcccaacgt gcgcca                                                       16

<210> SEQ ID NO 18
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: 5-methyl cytosine
<220> FEATURE:
<221> NAME/KEY: misc_feature
<222> LOCATION: (2)
<223> OTHER INFORMATION: modified LNA nucleotide
<220> FEATURE:
<221> NAME/KEY: misc_feature
<222> LOCATION: (3)
<223> OTHER INFORMATION: 5-methyl cytosine
<220> FEATURE:
<221> NAME/KEY: misc_feature
<222> LOCATION: (13)
<223> OTHER INFORMATION: modified LNA nucleotide
<220> FEATURE:
<221> NAME/KEY: misc_feature
<222> LOCATION: (14)..(15)
```

```
<223> OTHER INFORMATION: 5-methyl cytosine
<220> FEATURE:
<221> NAME/KEY: misc_feature
<222> LOCATION: (1)..(16)
<223> OTHER INFORMATION: Phosphorothioate linkage

<400> SEQUENCE: 18
ctcccatcgt gcgcca                                                    16

<210> SEQ ID NO 19
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: 5-methyl cytosine
<220> FEATURE:
<221> NAME/KEY: misc_feature
<222> LOCATION: (2)
<223> OTHER INFORMATION: modified LNA nucleotide
<220> FEATURE:
<221> NAME/KEY: misc_feature
<222> LOCATION: (3)..(4)
<223> OTHER INFORMATION: 5-methyl cytosine
<220> FEATURE:
<221> NAME/KEY: misc_feature
<222> LOCATION: (12)
<223> OTHER INFORMATION: 5-methyl cytosine
<220> FEATURE:
<221> NAME/KEY: misc_feature
<222> LOCATION: (13)
<223> OTHER INFORMATION: modified LNA nucleotide
<220> FEATURE:
<221> NAME/KEY: misc_feature
<222> LOCATION: (14)..(15)
<223> OTHER INFORMATION: 5-methyl cytosine
<220> FEATURE:
<221> NAME/KEY: misc_feature
<222> LOCATION: (1)..(16)
<223> OTHER INFORMATION: Phosphorothioate linkage

<400> SEQUENCE: 19
ctcccaacgt gcgcca                                                    16

<210> SEQ ID NO 20
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: 5-methyl cytosine
<220> FEATURE:
<221> NAME/KEY: misc_feature
<222> LOCATION: (2)
<223> OTHER INFORMATION: modified LNA nucleotide
<220> FEATURE:
<221> NAME/KEY: misc_feature
<222> LOCATION: (13)
<223> OTHER INFORMATION: modified LNA nucleotide
<220> FEATURE:
<221> NAME/KEY: misc_feature
<222> LOCATION: (14)..(15)
<223> OTHER INFORMATION: 5-methyl cytosine
<220> FEATURE:
<221> NAME/KEY: misc_feature
<222> LOCATION: (1)..(16)
<223> OTHER INFORMATION: Phosphorothioate linkage
```

```
<400> SEQUENCE: 20
ctcccaacgt gcgcca                                                      16

<210> SEQ ID NO 21
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: 5-methyl cytosine
<220> FEATURE:
<221> NAME/KEY: misc_feature
<222> LOCATION: (2)
<223> OTHER INFORMATION: modified LNA nucleotide
<220> FEATURE:
<221> NAME/KEY: misc_feature
<222> LOCATION: (14)..(15)
<223> OTHER INFORMATION: 5-methyl cytosine
<220> FEATURE:
<221> NAME/KEY: misc_feature
<222> LOCATION: (1)..(16)
<223> OTHER INFORMATION: Phosphorothioate linkage

<400> SEQUENCE: 21
ctcccagcgc gcgcca                                                      16

<210> SEQ ID NO 22
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: 5-methyl cytosine
<220> FEATURE:
<221> NAME/KEY: misc_feature
<222> LOCATION: (2)
<223> OTHER INFORMATION: modified LNA nucleotide
<220> FEATURE:
<221> NAME/KEY: misc_feature
<222> LOCATION: (3)
<223> OTHER INFORMATION: 5-methyl cytosine
<220> FEATURE:
<221> NAME/KEY: misc_feature
<222> LOCATION: (13)
<223> OTHER INFORMATION: modified LNA nucleotide
<220> FEATURE:
<221> NAME/KEY: misc_feature
<222> LOCATION: (14)..(15)
<223> OTHER INFORMATION: 5-methyl cytosine
<220> FEATURE:
<221> NAME/KEY: misc_feature
<222> LOCATION: (1)..(16)
<223> OTHER INFORMATION: Phosphorothioate linkage

<400> SEQUENCE: 22
ctcccagcgc gcgcca                                                      16

<210> SEQ ID NO 23
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: misc_feature
<222> LOCATION: (1)
<223> OTHER INFORMATION: 5-methyl cytosine
<220> FEATURE:
<221> NAME/KEY: misc_feature
<222> LOCATION: (2)
<223> OTHER INFORMATION: modified LNA nucleotide
<220> FEATURE:
<221> NAME/KEY: misc_feature
<222> LOCATION: (3)..(4)
<223> OTHER INFORMATION: 5-methyl cytosine
<220> FEATURE:
<221> NAME/KEY: misc_feature
<222> LOCATION: (12)
<223> OTHER INFORMATION: 5-methyl cytosine
<220> FEATURE:
<221> NAME/KEY: misc_feature
<222> LOCATION: (13)
<223> OTHER INFORMATION: modified LNA nucleotide
<220> FEATURE:
<221> NAME/KEY: misc_feature
<222> LOCATION: (14)..(15)
<223> OTHER INFORMATION: 5-methyl cytosine
<220> FEATURE:
<221> NAME/KEY: misc_feature
<222> LOCATION: (1)..(16)
<223> OTHER INFORMATION: Phosphorothioate linkage

<400> SEQUENCE: 23
ctcccagcgc gcgcca                                                    16

<210> SEQ ID NO 24
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: 5-methyl cytosine
<220> FEATURE:
<221> NAME/KEY: misc_feature
<222> LOCATION: (2)
<223> OTHER INFORMATION: modified LNA nucleotide
<220> FEATURE:
<221> NAME/KEY: misc_feature
<222> LOCATION: (14)..(15)
<223> OTHER INFORMATION: 5-methyl cytosine
<220> FEATURE:
<221> NAME/KEY: misc_feature
<222> LOCATION: (1)..(16)
<223> OTHER INFORMATION: Phosphorothioate linkage

<400> SEQUENCE: 24
ctcccagcga gcgcca                                                    16

<210> SEQ ID NO 25
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: 5-methyl cytosine
<220> FEATURE:
<221> NAME/KEY: misc_feature
<222> LOCATION: (2)
<223> OTHER INFORMATION: modified LNA nucleotide
<220> FEATURE:
```

```
<221> NAME/KEY: misc_feature
<222> LOCATION: (14)..(15)
<223> OTHER INFORMATION: 5-methyl cytosine
<220> FEATURE:
<221> NAME/KEY: misc_feature
<222> LOCATION: (1)..(16)
<223> OTHER INFORMATION: Phosphorothioate linkage

<400> SEQUENCE: 25
ctcccagcgg gcgcca                                                         16

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: modified LNA nucleotide
<220> FEATURE:
<221> NAME/KEY: misc_feature
<222> LOCATION: (2)
<223> OTHER INFORMATION: 5-methyl cytosine
<220> FEATURE:
<221> NAME/KEY: misc_feature
<222> LOCATION: (3)
<223> OTHER INFORMATION: modified LNA nucleotide
<220> FEATURE:
<221> NAME/KEY: misc_feature
<222> LOCATION: (15)..(16)
<223> OTHER INFORMATION: 5-methyl cytosine
<220> FEATURE:
<221> NAME/KEY: misc_feature
<222> LOCATION: (17)
<223> OTHER INFORMATION: modified LNA nucleotide
<220> FEATURE:
<221> NAME/KEY: misc_feature
<222> LOCATION: (2)..(18)
<223> OTHER INFORMATION: Phosphorothioate linkage

<400> SEQUENCE: 26
tctcccagag tgcgccat                                                       18

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: modified LNA nucleotide
<220> FEATURE:
<221> NAME/KEY: misc_feature
<222> LOCATION: (2)
<223> OTHER INFORMATION: 5-methyl cytosine
<220> FEATURE:
<221> NAME/KEY: misc_feature
<222> LOCATION: (3)
<223> OTHER INFORMATION: modified LNA nucleotide
<220> FEATURE:
<221> NAME/KEY: misc_feature
<222> LOCATION: (15)..(16)
<223> OTHER INFORMATION: 5-methyl cytosine
<220> FEATURE:
<221> NAME/KEY: misc_feature
<222> LOCATION: (17)
<223> OTHER INFORMATION: modified LNA nucleotide
<220> FEATURE:
<221> NAME/KEY: misc_feature
```

```
<222> LOCATION: (2)..(18)
<223> OTHER INFORMATION: Phosphorothioate linkage

<400> SEQUENCE: 27
tctcccagtg tgcgccat                                                 18

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: modified LNA nucleotide
<220> FEATURE:
<221> NAME/KEY: misc_feature
<222> LOCATION: (2)
<223> OTHER INFORMATION: 5-methyl cytosine
<220> FEATURE:
<221> NAME/KEY: misc_feature
<222> LOCATION: (3)
<223> OTHER INFORMATION: modified LNA nucleotide
<220> FEATURE:
<221> NAME/KEY: misc_feature
<222> LOCATION: (15)..(16)
<223> OTHER INFORMATION: 5-methyl cytosine
<220> FEATURE:
<221> NAME/KEY: misc_feature
<222> LOCATION: (17)
<223> OTHER INFORMATION: modified LNA nucleotide
<220> FEATURE:
<221> NAME/KEY: misc_feature
<222> LOCATION: (2)..(18)
<223> OTHER INFORMATION: Phosphorothioate linkage

<400> SEQUENCE: 28
tctcccaggg tgcgccat                                                 18

<210> SEQ ID NO 29
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: 5-methyl cytosine
<220> FEATURE:
<221> NAME/KEY: misc_feature
<222> LOCATION: (2)
<223> OTHER INFORMATION: modified LNA nucleotide
<220> FEATURE:
<221> NAME/KEY: misc_feature
<222> LOCATION: (14)..(15)
<223> OTHER INFORMATION: 5-methyl cytosine
<220> FEATURE:
<221> NAME/KEY: misc_feature
<222> LOCATION: (1)..(15)
<223> OTHER INFORMATION: Phosphorothioate linkage

<400> SEQUENCE: 29
ctcccaacgt gcgcc                                                    15

<210> SEQ ID NO 30
<211> LENGTH: 14
<212> TYPE: DNA
<213> ORGANISM: Artificial Sequence
<220> FEATURE:
```

<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: 5-methyl cytosine
<220> FEATURE:
<221> NAME/KEY: misc_feature
<222> LOCATION: (2)
<223> OTHER INFORMATION: modified LNA nucleotide
<220> FEATURE:
<221> NAME/KEY: misc_feature
<222> LOCATION: (14)
<223> OTHER INFORMATION: 5-methyl cytosine
<220> FEATURE:
<221> NAME/KEY: misc_feature
<222> LOCATION: (1)..(14)
<223> OTHER INFORMATION: Phosphorothioate linkage

<400> SEQUENCE: 30
ctcccaacgt gcgc                                                       14

<210> SEQ ID NO 31
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: 5-methyl cytosine
<220> FEATURE:
<221> NAME/KEY: misc_feature
<222> LOCATION: (2)
<223> OTHER INFORMATION: modified LNA nucleotide
<220> FEATURE:
<221> NAME/KEY: misc_feature
<222> LOCATION: (1)..(13)
<223> OTHER INFORMATION: Phosphorothioate linkage

<400> SEQUENCE: 31
ctcccaacgt gcg                                                        13

<210> SEQ ID NO 32
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: modified LNA nucleotide
<220> FEATURE:
<221> NAME/KEY: misc_feature
<222> LOCATION: (13)..(14)
<223> OTHER INFORMATION: 5-methyl cytosine
<220> FEATURE:
<221> NAME/KEY: misc_feature
<222> LOCATION: (1)..(15)
<223> OTHER INFORMATION: Phosphorothioate linkage

<400> SEQUENCE: 32
tcccaacgtg cgcca                                                      15

<210> SEQ ID NO 33
<211> LENGTH: 14
<212> TYPE: DNA
<213> ORGANISM: Artificial Sequence
<220> FEATURE:

<223> OTHER INFORMATION: Description of Artificial Sequence: Synthetic
      oligonucleotide
<220> FEATURE:
<221> NAME/KEY: misc_feature
<222> LOCATION: (12)..(13)
<223> OTHER INFORMATION: 5-methyl cytosine
<220> FEATURE:
<221> NAME/KEY: misc_feature
<222> LOCATION: (1)..(14)
<223> OTHER INFORMATION: Phosphorothioate linkage

<400> SEQUENCE: 33
cccaacgtgc gcca                                                         14

<210> SEQ ID NO 34
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (11)..(12)
<223> OTHER INFORMATION: 5-methyl cytosine
<220> FEATURE:
<221> NAME/KEY: misc_feature
<222> LOCATION: (1)..(13)
<223> OTHER INFORMATION: Phosphorothioate linkage

<400> SEQUENCE: 34
ccaacgtgcg cca                                                          13

<210> SEQ ID NO 35
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: 5-methyl cytosine
<220> FEATURE:
<221> NAME/KEY: misc_feature
<222> LOCATION: (2)
<223> OTHER INFORMATION: modified LNA nucleotide
<220> FEATURE:
<221> NAME/KEY: misc_feature
<222> LOCATION: (14)..(15)
<223> OTHER INFORMATION: 5-methyl cytosine
<220> FEATURE:
<221> NAME/KEY: misc_feature
<222> LOCATION: (1)..(15)
<223> OTHER INFORMATION: Phosphorothioate linkage

<400> SEQUENCE: 35
ctcccagcgt gcgcc                                                        15

<210> SEQ ID NO 36
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: 5-methyl cytosine
<220> FEATURE:
<221> NAME/KEY: misc_feature

```
<222> LOCATION: (2)
<223> OTHER INFORMATION: modified LNA nucleotide
<220> FEATURE:
<221> NAME/KEY: misc_feature
<222> LOCATION: (14)
<223> OTHER INFORMATION: 5-methyl cytosine
<220> FEATURE:
<221> NAME/KEY: misc_feature
<222> LOCATION: (1)..(14)
<223> OTHER INFORMATION: Phosphorothioate linkage

<400> SEQUENCE: 36
ctcccagcgt gcgc                                                    14

<210> SEQ ID NO 37
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: 5-methyl cytosine
<220> FEATURE:
<221> NAME/KEY: misc_feature
<222> LOCATION: (2)
<223> OTHER INFORMATION: modified LNA nucleotide
<220> FEATURE:
<221> NAME/KEY: misc_feature
<222> LOCATION: (1)..(13)
<223> OTHER INFORMATION: Phosphorothioate linkage

<400> SEQUENCE: 37
ctcccagcgt gcg                                                     13

<210> SEQ ID NO 38
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: modified LNA nucleotide
<220> FEATURE:
<221> NAME/KEY: misc_feature
<222> LOCATION: (13)..(14)
<223> OTHER INFORMATION: 5-methyl cytosine
<220> FEATURE:
<221> NAME/KEY: misc_feature
<222> LOCATION: (1)..(15)
<223> OTHER INFORMATION: Phosphorothioate linkage

<400> SEQUENCE: 38
tcccagcgtg cgcca                                                   15

<210> SEQ ID NO 39
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (12)..(13)
<223> OTHER INFORMATION: 5-methyl cytosine
<220> FEATURE:
<221> NAME/KEY: misc_feature
```

```
<222> LOCATION: (1)..(14)
<223> OTHER INFORMATION: Phosphorothioate linkage

<400> SEQUENCE: 39
cccagcgtgc gcca                                                      14

<210> SEQ ID NO 40
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (11)..(12)
<223> OTHER INFORMATION: 5-methyl cytosine
<220> FEATURE:
<221> NAME/KEY: misc_feature
<222> LOCATION: (1)..(13)
<223> OTHER INFORMATION: Phosphorothioate linkage

<400> SEQUENCE: 40
ccagcgtgcg cca                                                       13

<210> SEQ ID NO 41
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: 5-methyl cytosine
<220> FEATURE:
<221> NAME/KEY: misc_feature
<222> LOCATION: (2)
<223> OTHER INFORMATION: modified LNA nucleotide
<220> FEATURE:
<221> NAME/KEY: misc_feature
<222> LOCATION: (15)
<223> OTHER INFORMATION: 5-methyl cytosine
<220> FEATURE:
<221> NAME/KEY: misc_feature
<222> LOCATION: (16)
<223> OTHER INFORMATION: modified LNA nucleotide
<220> FEATURE:
<221> NAME/KEY: misc_feature
<222> LOCATION: (1)..(17)
<223> OTHER INFORMATION: Phosphorothioate linkage

<400> SEQUENCE: 41
ctcccagcgt gcgccat                                                   17

<210> SEQ ID NO 42
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: 5-methyl cytosine
<220> FEATURE:
<221> NAME/KEY: misc_feature
<222> LOCATION: (2)
<223> OTHER INFORMATION: modified LNA nucleotide
<220> FEATURE:
<221> NAME/KEY: misc_feature
```

```
<222> LOCATION: (3)
<223> OTHER INFORMATION: 5-methyl cytosine
<220> FEATURE:
<221> NAME/KEY: misc_feature
<222> LOCATION: (14)..(15)
<223> OTHER INFORMATION: 5-methyl cytosine
<220> FEATURE:
<221> NAME/KEY: misc_feature
<222> LOCATION: (16)
<223> OTHER INFORMATION: modified LNA nucleotide
<220> FEATURE:
<221> NAME/KEY: misc_feature
<222> LOCATION: (1)..(17)
<223> OTHER INFORMATION: Phosphorothioate linkage

<400> SEQUENCE: 42
ctcccagcgt gcgccat                                                    17

<210> SEQ ID NO 43
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: 5-methyl cytosine
<220> FEATURE:
<221> NAME/KEY: misc_feature
<222> LOCATION: (2)
<223> OTHER INFORMATION: modified LNA nucleotide
<220> FEATURE:
<221> NAME/KEY: misc_feature
<222> LOCATION: (3)..(4)
<223> OTHER INFORMATION: 5-methyl cytosine
<220> FEATURE:
<221> NAME/KEY: misc_feature
<222> LOCATION: (13)
<223> OTHER INFORMATION: modified LNA nucleotide
<220> FEATURE:
<221> NAME/KEY: misc_feature
<222> LOCATION: (14)..(15)
<223> OTHER INFORMATION: 5-methyl cytosine
<220> FEATURE:
<221> NAME/KEY: misc_feature
<222> LOCATION: (16)
<223> OTHER INFORMATION: modified LNA nucleotide
<220> FEATURE:
<221> NAME/KEY: misc_feature
<222> LOCATION: (1)..(17)
<223> OTHER INFORMATION: Phosphorothioate linkage

<400> SEQUENCE: 43
ctcccagcgt gcgccat                                                    17

<210> SEQ ID NO 44
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: modified LNA nucleotide
<220> FEATURE:
<221> NAME/KEY: misc_feature
<222> LOCATION: (2)
<223> OTHER INFORMATION: 5-methyl cytosine
<220> FEATURE:
<221> NAME/KEY: misc_feature
<222> LOCATION: (15)..(16)
```

```
<223> OTHER INFORMATION: 5-methyl cytosine
<220> FEATURE:
<221> NAME/KEY: misc_feature
<222> LOCATION: (1)..(17)
<223> OTHER INFORMATION: Phosphorothioate linkage

<400> SEQUENCE: 44
tctcccagcg tgcgcca                                                    17

<210> SEQ ID NO 45
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: modified LNA nucleotide
<220> FEATURE:
<221> NAME/KEY: misc_feature
<222> LOCATION: (2)
<223> OTHER INFORMATION: 5-methyl cytosine
<220> FEATURE:
<221> NAME/KEY: misc_feature
<222> LOCATION: (3)
<223> OTHER INFORMATION: modified LNA nucleotide
<220> FEATURE:
<221> NAME/KEY: misc_feature
<222> LOCATION: (14)
<223> OTHER INFORMATION: modified LNA nucleotide
<220> FEATURE:
<221> NAME/KEY: misc_feature
<222> LOCATION: (15)..(16)
<223> OTHER INFORMATION: 5-methyl cytosine
<220> FEATURE:
<221> NAME/KEY: misc_feature
<222> LOCATION: (1)..(17)
<223> OTHER INFORMATION: Phosphorothioate linkage

<400> SEQUENCE: 45
tctcccagcg tgcgcca                                                    17

<210> SEQ ID NO 46
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: modified LNA nucleotide
<220> FEATURE:
<221> NAME/KEY: misc_feature
<222> LOCATION: (2)
<223> OTHER INFORMATION: 5-methyl cytosine
<220> FEATURE:
<221> NAME/KEY: misc_feature
<222> LOCATION: (3)
<223> OTHER INFORMATION: modified LNA nucleotide
<220> FEATURE:
<221> NAME/KEY: misc_feature
<222> LOCATION: (4)
<223> OTHER INFORMATION: 5-methyl cytosine
<220> FEATURE:
<221> NAME/KEY: misc_feature
<222> LOCATION: (13)
<223> OTHER INFORMATION: 5-methyl cytosine
<220> FEATURE:
<221> NAME/KEY: misc_feature
<222> LOCATION: (14)
<223> OTHER INFORMATION: modified LNA nucleotide
```

```
<220> FEATURE:
<221> NAME/KEY: misc_feature
<222> LOCATION: (15)..(16)
<223> OTHER INFORMATION: 5-methyl cytosine
<220> FEATURE:
<221> NAME/KEY: misc_feature
<222> LOCATION: (1)..(17)
<223> OTHER INFORMATION: Phosphorothioate linkage

<400> SEQUENCE: 46
tctcccagcg tgcgcca                                                    17

<210> SEQ ID NO 47
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: modified LNA nucleotide
<220> FEATURE:
<221> NAME/KEY: misc_feature
<222> LOCATION: (2)
<223> OTHER INFORMATION: 5-methyl cytosine
<220> FEATURE:
<221> NAME/KEY: misc_feature
<222> LOCATION: (14)
<223> OTHER INFORMATION: modified LNA nucleotide
<220> FEATURE:
<221> NAME/KEY: misc_feature
<222> LOCATION: (15)
<223> OTHER INFORMATION: 5-methyl cytosine
<220> FEATURE:
<221> NAME/KEY: misc_feature
<222> LOCATION: (1)..(16)
<223> OTHER INFORMATION: Phosphorothioate linkage

<400> SEQUENCE: 47
tctcccagcg tgcgcc                                                     16

<210> SEQ ID NO 48
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: modified LNA nucleotide
<220> FEATURE:
<221> NAME/KEY: misc_feature
<222> LOCATION: (2)
<223> OTHER INFORMATION: 5-methyl cytosine
<220> FEATURE:
<221> NAME/KEY: misc_feature
<222> LOCATION: (3)
<223> OTHER INFORMATION: modified LNA nucleotide
<220> FEATURE:
<221> NAME/KEY: misc_feature
<222> LOCATION: (13)
<223> OTHER INFORMATION: 5-methyl cytosine
<220> FEATURE:
<221> NAME/KEY: misc_feature
<222> LOCATION: (14)
<223> OTHER INFORMATION: modified LNA nucleotide
<220> FEATURE:
<221> NAME/KEY: misc_feature
<222> LOCATION: (15)
<223> OTHER INFORMATION: 5-methyl cytosine
<220> FEATURE:
```

```
<221> NAME/KEY: misc_feature
<222> LOCATION: (1)..(16)
<223> OTHER INFORMATION: Phosphorothioate linkage

<400> SEQUENCE: 48
tctcccagcg tgcgcc                                                         16

<210> SEQ ID NO 49
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: modified LNA nucleotide
<220> FEATURE:
<221> NAME/KEY: misc_feature
<222> LOCATION: (2)
<223> OTHER INFORMATION: 5-methyl cytosine
<220> FEATURE:
<221> NAME/KEY: misc_feature
<222> LOCATION: (3)
<223> OTHER INFORMATION: modified LNA nucleotide
<220> FEATURE:
<221> NAME/KEY: misc_feature
<222> LOCATION: (4)
<223> OTHER INFORMATION: 5-methyl cytosine
<220> FEATURE:
<221> NAME/KEY: misc_feature
<222> LOCATION: (12)
<223> OTHER INFORMATION: modified LNA nucleotide
<220> FEATURE:
<221> NAME/KEY: misc_feature
<222> LOCATION: (13)
<223> OTHER INFORMATION: 5-methyl cytosine
<220> FEATURE:
<221> NAME/KEY: misc_feature
<222> LOCATION: (14)
<223> OTHER INFORMATION: modified LNA nucleotide
<220> FEATURE:
<221> NAME/KEY: misc_feature
<222> LOCATION: (15)
<223> OTHER INFORMATION: 5-methyl cytosine
<220> FEATURE:
<221> NAME/KEY: misc_feature
<222> LOCATION: (1)..(16)
<223> OTHER INFORMATION: Phosphorothioate linkage

<400> SEQUENCE: 49
tctcccagcg tgcgcc                                                         16

<210> SEQ ID NO 50
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: modified LNA nucleotide
<220> FEATURE:
<221> NAME/KEY: misc_feature
<222> LOCATION: (2)
<223> OTHER INFORMATION: 5-methyl cytosine
<220> FEATURE:
<221> NAME/KEY: misc_feature
<222> LOCATION: (14)
<223> OTHER INFORMATION: 5-methyl cytosine
<220> FEATURE:
<221> NAME/KEY: misc_feature
```

```
<222> LOCATION: (15)
<223> OTHER INFORMATION: modified LNA nucleotide
<220> FEATURE:
<221> NAME/KEY: misc_feature
<222> LOCATION: (1)..(16)
<223> OTHER INFORMATION: Phosphorothioate linkage

<400> SEQUENCE: 50
tcccagcgtg cgccat                                                    16

<210> SEQ ID NO 51
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: modified LNA nucleotide
<220> FEATURE:
<221> NAME/KEY: misc_feature
<222> LOCATION: (2)..(3)
<223> OTHER INFORMATION: 5-methyl cytosine
<220> FEATURE:
<221> NAME/KEY: misc_feature
<222> LOCATION: (13)..(14)
<223> OTHER INFORMATION: 5-methyl cytosine
<220> FEATURE:
<221> NAME/KEY: misc_feature
<222> LOCATION: (15)
<223> OTHER INFORMATION: modified LNA nucleotide
<220> FEATURE:
<221> NAME/KEY: misc_feature
<222> LOCATION: (1)..(16)
<223> OTHER INFORMATION: Phosphorothioate linkage

<400> SEQUENCE: 51
tcccagcgtg cgccat                                                    16

<210> SEQ ID NO 52
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: modified LNA nucleotide
<220> FEATURE:
<221> NAME/KEY: misc_feature
<222> LOCATION: (2)..(4)
<223> OTHER INFORMATION: 5-methyl cytosine
<220> FEATURE:
<221> NAME/KEY: misc_feature
<222> LOCATION: (12)
<223> OTHER INFORMATION: modified LNA nucleotide
<220> FEATURE:
<221> NAME/KEY: misc_feature
<222> LOCATION: (13)..(14)
<223> OTHER INFORMATION: 5-methyl cytosine
<220> FEATURE:
<221> NAME/KEY: misc_feature
<222> LOCATION: (15)
<223> OTHER INFORMATION: modified LNA nucleotide
<220> FEATURE:
<221> NAME/KEY: misc_feature
<222> LOCATION: (1)..(16)
<223> OTHER INFORMATION: Phosphorothioate linkage

<400> SEQUENCE: 52
```
tcccagcgtg cgccat                                                                                     16

<210> SEQ ID NO 53
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: modified LNA nucleotide
<220> FEATURE:
<221> NAME/KEY: misc_feature
<222> LOCATION: (2)
<223> OTHER INFORMATION: 5-methyl cytosine
<220> FEATURE:
<221> NAME/KEY: misc_feature
<222> LOCATION: (3)
<223> OTHER INFORMATION: modified LNA nucleotide
<220> FEATURE:
<221> NAME/KEY: misc_feature
<222> LOCATION: (15)..(16)
<223> OTHER INFORMATION: 5-methyl cytosine
<220> FEATURE:
<221> NAME/KEY: misc_feature
<222> LOCATION: (17)
<223> OTHER INFORMATION: modified LNA nucleotide
<220> FEATURE:
<221> NAME/KEY: misc_feature
<222> LOCATION: (2)..(18)
<223> OTHER INFORMATION: Phosphorothioate linkage

<400> SEQUENCE: 53
tctcccagca tgcgccat                                                                                   18

<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: modified LNA nucleotide
<220> FEATURE:
<221> NAME/KEY: misc_feature
<222> LOCATION: (2)
<223> OTHER INFORMATION: 5-methyl cytosine
<220> FEATURE:
<221> NAME/KEY: misc_feature
<222> LOCATION: (3)
<223> OTHER INFORMATION: modified LNA nucleotide
<220> FEATURE:
<221> NAME/KEY: misc_feature
<222> LOCATION: (15)..(16)
<223> OTHER INFORMATION: 5-methyl cytosine
<220> FEATURE:
<221> NAME/KEY: misc_feature
<222> LOCATION: (17)
<223> OTHER INFORMATION: modified LNA nucleotide
<220> FEATURE:
<221> NAME/KEY: misc_feature
<222> LOCATION: (2)..(18)
<223> OTHER INFORMATION: Phosphorothioate linkage

<400> SEQUENCE: 54
tctcccagct tgcgccat                                                                                   18

<210> SEQ ID NO 55
<211> LENGTH: 18

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: modified LNA nucleotide
<220> FEATURE:
<221> NAME/KEY: misc_feature
<222> LOCATION: (2)
<223> OTHER INFORMATION: 5-methyl cytosine
<220> FEATURE:
<221> NAME/KEY: misc_feature
<222> LOCATION: (3)
<223> OTHER INFORMATION: modified LNA nucleotide
<220> FEATURE:
<221> NAME/KEY: misc_feature
<222> LOCATION: (15)..(16)
<223> OTHER INFORMATION: 5-methyl cytosine
<220> FEATURE:
<221> NAME/KEY: misc_feature
<222> LOCATION: (17)
<223> OTHER INFORMATION: modified LNA nucleotide
<220> FEATURE:
<221> NAME/KEY: misc_feature
<222> LOCATION: (2)..(18)
<223> OTHER INFORMATION: Phosphorothioate linkage

<400> SEQUENCE: 55
tctcccagcc tgcgccat                                                  18

<210> SEQ ID NO 56
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(18)
<223> OTHER INFORMATION: Phosphorothioate linkage

<400> SEQUENCE: 56
tctcccagcg tgcgccat                                                  18

<210> SEQ ID NO 57
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: modified LNA nucleotide
<220> FEATURE:
<221> NAME/KEY: misc_feature
<222> LOCATION: (2)
<223> OTHER INFORMATION: 5-methyl cytosine
<220> FEATURE:
<221> NAME/KEY: misc_feature
<222> LOCATION: (3)
<223> OTHER INFORMATION: modified LNA nucleotide
<220> FEATURE:
<221> NAME/KEY: misc_feature
<222> LOCATION: (15)..(16)
<223> OTHER INFORMATION: 5-methyl cytosine
<220> FEATURE:
<221> NAME/KEY: misc_feature
<222> LOCATION: (17)
<223> OTHER INFORMATION: modified LNA nucleotide
```

```
<220> FEATURE:
<221> NAME/KEY: misc_feature
<222> LOCATION: (1)..(18)
<223> OTHER INFORMATION: Phosphorothioate linkage

<400> SEQUENCE: 57
tctcccagca tgtgccat                                                         18

<210> SEQ ID NO 58
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: modified LNA nucleotide
<220> FEATURE:
<221> NAME/KEY: misc_feature
<222> LOCATION: (2)
<223> OTHER INFORMATION: 5-methyl cytosine
<220> FEATURE:
<221> NAME/KEY: misc_feature
<222> LOCATION: (14)
<223> OTHER INFORMATION: 5-methyl cytosine
<220> FEATURE:
<221> NAME/KEY: misc_feature
<222> LOCATION: (15)
<223> OTHER INFORMATION: modified LNA nucleotide
<220> FEATURE:
<221> NAME/KEY: misc_feature
<222> LOCATION: (1)..(16)
<223> OTHER INFORMATION: Phosphorothioate linkage

<400> SEQUENCE: 58
accgcgtgcg accctc                                                           16

<210> SEQ ID NO 59
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (2)
<223> OTHER INFORMATION: 5-methyl cytosine
<220> FEATURE:
<221> NAME/KEY: misc_feature
<222> LOCATION: (4)..(6)
<223> OTHER INFORMATION: 5-methyl cytosine
<220> FEATURE:
<221> NAME/KEY: misc_feature
<222> LOCATION: (9)
<223> OTHER INFORMATION: 5-methyl cytosine
<220> FEATURE:
<221> NAME/KEY: misc_feature
<222> LOCATION: (13)
<223> OTHER INFORMATION: 5-methyl cytosine
<220> FEATURE:
<221> NAME/KEY: misc_feature
<222> LOCATION: (15)..(16)
<223> OTHER INFORMATION: 5-methyl cytosine
<220> FEATURE:
<221> NAME/KEY: misc_feature
<222> LOCATION: (1)..(18)
<223> OTHER INFORMATION: Phosphorothioate linkage

<400> SEQUENCE: 59
tctcccagcg tgcgccat                                                         18
```

```
<210> SEQ ID NO 60
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: 5-methyl cytosine
<220> FEATURE:
<221> NAME/KEY: misc_feature
<222> LOCATION: (2)
<223> OTHER INFORMATION: modified LNA nucleotide
<220> FEATURE:
<221> NAME/KEY: misc_feature
<222> LOCATION: (8)
<223> OTHER INFORMATION: 5-methyl cytosine
<220> FEATURE:
<221> NAME/KEY: misc_feature
<222> LOCATION: (12)
<223> OTHER INFORMATION: 5-methyl cytosine
<220> FEATURE:
<221> NAME/KEY: misc_feature
<222> LOCATION: (14)..(15)
<223> OTHER INFORMATION: 5-methyl cytosine
<220> FEATURE:
<221> NAME/KEY: misc_feature
<222> LOCATION: (1)..(16)
<223> OTHER INFORMATION: Phosphorothioate linkage

<400> SEQUENCE: 60
ctcccaacgt gcgcca                                                      16

<210> SEQ ID NO 61
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)
<223> OTHER INFORMATION: 5-methyl cytosine
<220> FEATURE:
<221> NAME/KEY: misc_feature
<222> LOCATION: (2)
<223> OTHER INFORMATION: modified LNA nucleotide
<220> FEATURE:
<221> NAME/KEY: misc_feature
<222> LOCATION: (3)..(5)
<223> OTHER INFORMATION: 5-methyl cytosine
<220> FEATURE:
<221> NAME/KEY: misc_feature
<222> LOCATION: (8)
<223> OTHER INFORMATION: 5-methyl cytosine
<220> FEATURE:
<221> NAME/KEY: misc_feature
<222> LOCATION: (12)
<223> OTHER INFORMATION: 5-methyl cytosine
<220> FEATURE:
<221> NAME/KEY: misc_feature
<222> LOCATION: (14)..(15)
<223> OTHER INFORMATION: 5-methyl cytosine
<220> FEATURE:
<221> NAME/KEY: misc_feature
<222> LOCATION: (1)..(16)
<223> OTHER INFORMATION: Phosphorothioate linkage

<400> SEQUENCE: 61
ctcccaacgt gcgcca                                                      16
```

```
<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
catgtgtgtg gagagcgtca a                                                21

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
gccggttcag gtactcagtc a                                                21

<210> SEQ ID NO 64
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
cctggtggac aacatcgccc tgt                                              23

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
tctcccagcg tgcgccat                                                    18
```

US 7,622,453 B2

OLIGOMERIC COMPOUNDS FOR THE MODULATION OF BCL-2

CROSS REFERENCE TO RELATED APPLICATIONS

The present application claims priority to U.S. provisional applications Ser. Nos. 60/532,844, filed Dec. 23, 2003; 60/558,392, filed Mar. 31, 2004; 60/586,340, filed Jul. 7, 2004; and 60/621,594, filed Oct. 22, 2004. The present application also claims priority to Danish Patent Application No. PA 2003 01929, filed Dec. 23, 2003; Danish Patent Application No PA 2004 00517, filed Mar. 31, 2004; Danish Patent Application No. PA 2004 01069, filed Jul. 7, 2004; and Danish Patent Application No. PA 2004 01629, filed Oct. 22, 2004. The disclosures of the 60/532,844; 60/558,392; 60/586,340; 60/621,594; PA 2003 01929; 2004 00517; PA 2004 01069; and PA 2004 01629 are each incorporated herein by reference.

FIELD OF THE INVENTION

The present invention provides improved oligomeric compound and methods for modulating the expression of the Bcl-2 gene in humans. In particular, this invention relates to oligomeric compounds of 10-30 nucleobases in length which comprise a target binding domain that is specifically hybridizable to a region ranging from base position No. 1459 (5') to No. 1476 (3') of the human Bcl-2 mRNA, said target binding domain comprising at least two LNA nucleotides or LNA analogue nucleotides linked by a phosphorothioate group (—O—P(O,S)—O—).

Thus, the present invention relates to antisense oligomeric compounds directed against human Bcl-2 mRNA, and being capable of modulating the biosynthesis of human Bcl-2 protein. The present invention further relates to a pharmaceutical composition comprising such oligomeric compounds, uses thereof and methods of treatment and diagnosis utilizing such oligomeric compounds.

BACKGROUND OF THE INVENTION

Human Bcl-2 is a protein, which is closely associated with the process of programmed cell death (apoptosis). Apoptosis is an active, tightly regulated physiological process involved in development, normal cell turnover, and hormone-induced tissue athropy. Lack of programmed cell death plays an important role in cancer and other hyperproliferative diseases like restenosis, fibrosis, psoriasis or certain types of allergic diseases, in particular in tumour progression and, importantly, might contribute to the clinical problem of resistance to anti-neoplastic regimens, in particular standard chemotherapeutic compounds. In contrast to most normal tissues, in malignant tumours, such as a small cell lung cancer (SCLC) and non-small lung cancer (NSCLC), Bcl-2 is often co-expressed.

WO 95/08350 discloses anticode oligomers and methods of using them for controlling the growth of cancer cells expressing the Bcl-2 gene.

Klasa et al., Antisense & Nucleic Acid Drug Development 12: 1993-213 (2002) (review), discuss the biological effects of compound oblimersen sodium (G3139) and its potential as an antisense drug. The compound has the structure 5'-d(P-thio)TCT-CCC-AGC-GTG-CGC-CAT-3' (SEQ ID NO: 65). Genta Incorporated submitted an NDA to the FDA for oblimersen sodium (G3139) plus dacarbazine (DTIC). It was based on an international, multi-center randomized, phase 3 study of oblimersen sodium (G3139) plus dacarbazine (DTIC) versus DTIC alone every three weeks as first-line chemotherapy for metastatic melanoma. In May 2004, it was reported that the study failed to show a survival benefit from the combination of G3139 plus DTIC. The combination arm was associated with increased toxicity and discontinuations due to adverse events (AEs) including 69 (18.6%) patients who discontinued therapy for adverse events on the G3139 arm versus 39 (10.8%) on the DTIC alone arm. The rate of serious adverse events, SAEs, was 40% on the G3139 arm versus 27% on DTIC alone. Since the dosing of DTIC was identical in the two arms; toxicity increases were likely due to the addition of G3139. Survival was not improved and toxicity was increased. The NDA was subsequently withdrawn. However, the sponsor's analysis of secondary endpoints did show a statistically significant benefit in progression-free survival from a median of 49 days on DTIC to 74 days on the combination, a difference of 25 days (p=0.0003, HR=0.73). Also, the sponsor reported a significant difference in response rate of 6.8% for DTIC alone versus 11.7% for the combination (p=0.019). The fact that oblimersen sodium fulfilled the secondary endpoint indicates that it could have been an effective compound for the treatment of metastatic melanoma. The increased toxicity, the selection of primary endpoint and the overall clinical trail design were all factors that contributed to the failure.

LNA containing oligonucleotides targeting the 6 first codons of the human Bcl-2 mRNA were studied in a Ph.D. thesis defended by Jan Stenvang Jepsen (May 2003, University of Copenhagen). Fully modified LNA phosphodiester (PO) sequences, phosphorodiester headmers (LNA/PO at the 5'-end and DNA/PS phosphorothioate at the 3'-end), fully phosphorodiester gapmers (gap sizes of 8, 10, 12, 14) and gapmers with exclusive thiolation in the gap (gap sizes of 8, 10, 12, 14) were assayed for in vitro uptake with different transfecting agents and for down-regulation of Bcl-2 protein. The uptake study was performed in MCF-7 cells and the results were analyzed by microscopy and flow-cytometry. Equally efficient delivery was obtained for all the different PO and PO/PS containing constructs. Although a variety of LNA-containing oligonucleotides and constructs were studied, Stenvang Jepsen did not disclose or anticipate LNA-containing oligonucleotide gapmers wherein a substantial number of the nucleotides links in the target binding domain, including the LNA flanks, were phosphorothioate groups (—O—P(O,S)—O—), probably because it was known that phosphorothiolation would cause a reduction of affinity and because no stability problems were identified.

Frieden et al., Nucleic Acid Research, 2003, Vol. 31, No. 21, 6365-6373, and WO 2004/046160 A2 disclose various considerations with respect to the design of antisense oligonucleotides based on in vitro experiments.

Fluiter et al., Nucleic Acid Research, 2003, Vol. 3, 953-962, discloses in vivo tumour growth inhibition and biodistribution studies of LNA antisense oligonucleotides.

BRIEF DESCRIPTION OF THE INVENTION

In view of the above, and in particular the potency problems related to the oblimersen sodium compound, there is still need for improved oligomeric compound for down-regulating Bcl-2. Such compound should preferably have a suitable in vivo profile with respect to distribution and down-regulation of Bcl-2 and thereby therapeutic relevance in connection with various Bcl-2 related conditions, in particular cancer.

This being said, the present inventors have now found that certain novel LNA oligomeric compounds of the gapmer type exhibit comparable or enhanced biological effects compared to oblimersen sodium, while no adverse events at pharmacological relevant doses were monitored.

More specifically, the present inventors have found that oligomeric compounds of 10-30 nucleobases in length which comprise a target binding domain that is specifically hybridizable to a region ranging from base position No. 1459 (5') to No. 1476 (3') of the human Bcl-2 mRNA, wherein said target binding domain has the formula:

5'-[(DNA/RNA)$_{0-1}$-(LNA/LNA*)$_{2-7}$-(DNA/RNA/LNA*)$_{4-14}$-(LNA/LNA*)$_{2-7}$-(DNA/RNA)$_{0-1}$]-3' wherein "LNA" designates an LNA nucleotide and "LNA*" designates an LNA analogue nucleotide; and which in the target binding domain comprises at least two LNA nucleotides or LNA analogue nucleotides linked by a phosphorothioate group, have interesting biological properties.

DESCRIPTION OF THE INVENTION

Figure 1:
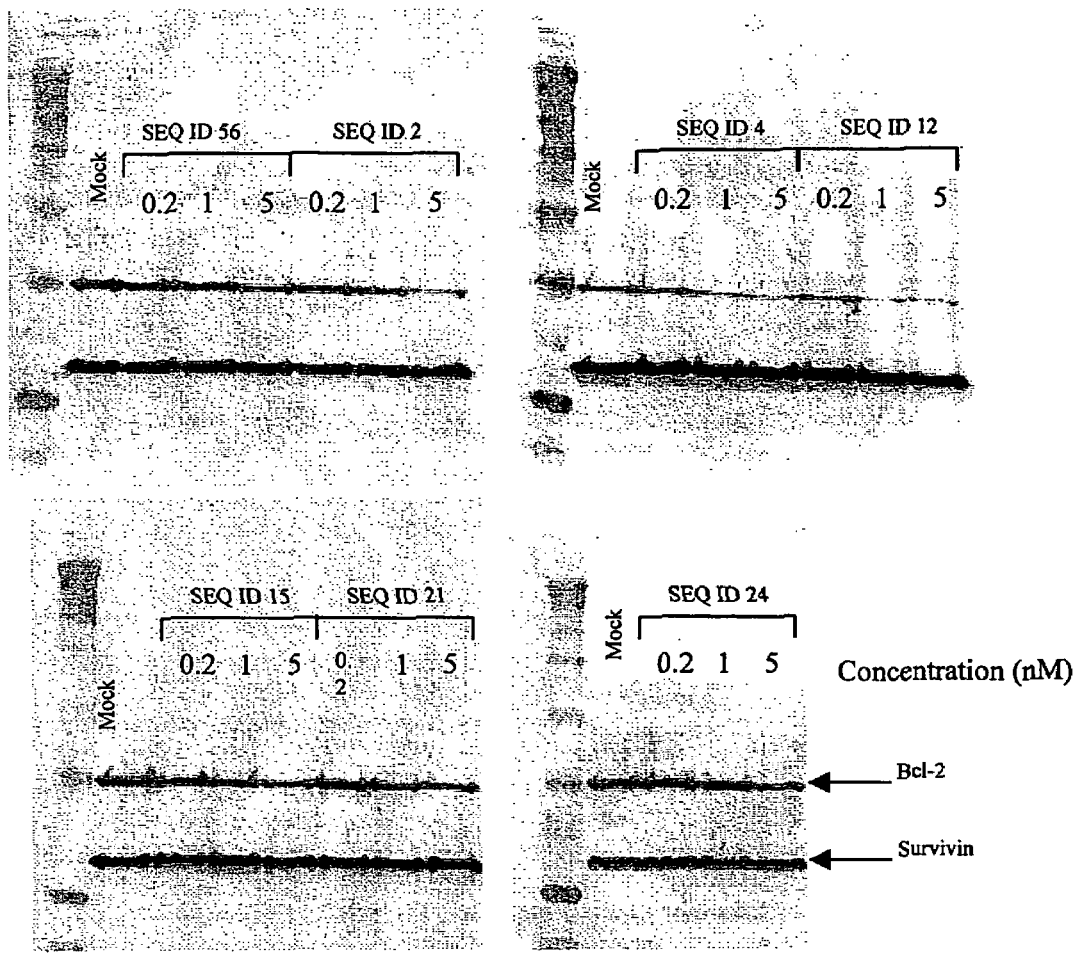
FIG. 1 shows down-regulation of Bcl-2 in 15PC3 cells transfected with LNA oligomeric compounds analyzed by western blotting. SEQ ID NOS: 2, 4, 15, 21 and 24 (see Table 1) were more potent inhibitors of Bcl-2 measured on protein levels compared to oblimersen sodium, i.e. SEQ ID NO: 56 (reference). The survivin protein served as a control.

As mentioned above, the present inventors have found that oligomeric compounds of 10-30 nucleobases in length which comprise a target binding domain that is specifically hybridizable to a region ranging from base position No. 1459 (5') to No. 1476 (3') of the human Bcl-2 mRNA, wherein said target binding domain has the formula:

5'-[(DNA/RNA)$_{0-1}$-(LNA/LNA*)$_{2-7}$-(DNA/RNA/LNA*)$_{4-14}$-(LNA/LNA)$_{2-7}$-(DNA/RNA)$_{0-1}$]-3' wherein "LNA" designates an LNA nucleotide and "LNA*" designates an LNA analogue nucleotide; and which in the target binding domain comprises at least two LNA nucleotides or LNA analogue nucleotides linked by a phosphorothioate group, have interesting biological properties.

Generally, the oligomeric compounds defined herein are believed to possess improved properties compared to the known oligomeric compounds. By the expression "improved properties" is understood one or more parameters by which the oligomeric compounds show better or eqeual overall performance compared to their phosphorothioate counterparts.

Examples of such improved parameters are longer shelf life of drug, higher binding constant to target (interim complement in oligomeric compound or mRNA target), good resistance to extra- and intracellular nucleases, higher potency in mode of action, better phenotypic response, longer lasting effects, better chemosensitization, and improved patient convenience. Examples of equal parameters are ease of production, ease to formulate pharmaceutically, tissue distribution, good safety profile.

In summary, the oligomeric compounds defined herein present $IC_{50}$ values in the very low nanomolar range (5 nM) with respect to downregulation of Bcl-2 mRNA, with respect to protein down-regulation (Bcl2/Bax ratio changed from 1 nM) and inhibition of cell proliferation. Far superior levels than the ones observed for oblimersen and for Jepsen's compounds (at 400 nM significant levels of down-regulation can be seen). Moreover, cell death correlates strongly with induction of apoptosis, and the levels of induction of apoptosis shown are far superior to oblimersen. Furthermore, the oligomeric compounds defined herein show a substantially increased stability in rat plasma, and a longer half-life in tissue as compared to oblimersen. Repeated antitumor response was observed in a prostate and a melanoma model; response even at 1 mg/Kg/day. In addition, antitumor response with less frequent dosing of the compound as compared to the usual dosage described in the literature for oblimersen was also observed. No adverse events at pharmacological relevant doses, such as elevation of ASAT, ALAT, were monitored. Our findings surpass Jepsen's constructs for which no functional response, stability, half-life in tissue, in vivo response, clinical chemistry or biodistribution was assayed.

The sequence of the human Bcl-2 mRNA as referred to herein is accessible in the GenBank Data Base as HUMBcl2A under accession number M13994. Within the context of the present application, the numbering of nucleic acids, in particular of mRNA or corresponding cDNA sequences, relates to the respective numbering of the human Bcl-2 mRNA as contained in said data base under said accession number. A corresponding cDNA sequence can be deduced from the mRNA sequence in particular by exchanging any base T of the cDNA sequence by a base U in the mRNA sequence, and vice versa.

The Oligomeric Compounds

The oligomeric compound is characterized in that it in the target binding domain comprises at least two LNA nucleotides or LNA analogue nucleotides linked by a phosphorothioate group.

When used herein, the expression "target binding domain" refers to a domain of an oligomeric compound (or even the oligomeric compound as such) which binds to specified target sequence, here a region ranging from base position No. 1459 (5') to No. 1476 (3') of the human Bcl-2 mRNA.

In one embodiment, the target binding domain comprises at least two LNA nucleotides linked by a phosphorothioate group (—O—P(O,S)—O—).

In another embodiment, the target binding domain comprises at least two LNA analogue nucleotides linked by a phosphorothioate group (—O—P(O,S)—O—).

As used herein, the term "oligomeric compounds" refers to LNA oligonucleotides, i.e. ribonucleic acid (RNA) or deoxyribonucleic acid (DNA) modified by substitution of one or more (or all) nucleotides therein with LNA nucleotides or LNA nucleotides, in particular at least two LNA nucleotides with the possible further substitution of nucleotides with LNA analogue nucleotides and nucleotide derivatives/analogues.

The term "oligonucleotide" includes oligonucleotides composed of naturally occurring nucleobases, sugars and internucleoside (backbone) linkages as well as oligonucleotides having non-naturally-occurring portions which function similarly or with specific improved functions.

The oligomeric compounds to be used in the context of the present invention are 10-30 nucleobases in length, e.g. 10-25, such as 10-20, e.g. 10-18, or 10-16, or 15-17 nucleobases in length.

The term "nucleobases in length" refers to the length in terms of number of nucleobases upon hybridization to a linear complementary nucleic acid molecule, i.e. the total number of nucleobases of the complementary nucleic acid in the region whereto the oligomeric compound is hybridized. Thus, the length of the oligomeric compound includes any intermediate nucleotides where a nucleobase is absent.

In one main embodiment, the oligomeric compounds (LNA oligonucleotides) of the invention comprise at least two LNA nucleotides.

In a further embodiment, the oligomeric compounds (LNA oligonucleotides) of the invention comprise at least two LNA analogue nucleotides, and possibly one or more LNA nucleotides.

The term "at least two" comprises the integers larger than or equal to 2, such as 2, 3, 4, 5, 6, 7, 8, 9, 10, 11, 12, 13, 14, 15, 16, 17 and so forth.

The term "at least one" comprises the integers larger than or equal to 1, such as 1, 2, 3, 4, 5, 6, 7, 8, 9, 10, 11, 12, 13, 14, 15, 16, 17 and so forth.

The term "a" as used about a nucleoside, a nucleoside analogue, a SEQ ID NO, etc. is intended to mean one or more. In particular, the expression "a component (such as a nucleoside, a nucleoside analogue, a SEQ ID NO: or the like) selected from the group consisting of . . . " is intended to mean that one or more of the cited components may be selected. Thus, expressions like "a component selected from the group consisting of A, B and C" is intended to include all combinations of A, B and C, i.e. A, B, C, A+B, A+C, B+C and A+B+C.

The term "LNA" (Locked Nucleic Acid) (or "LNA oligonucleotide") refers to an oligonucleotide containing one or more bicyclic nucleoside analogues also referred to as LNA nucleotides and LNA nucleotide analogues.

LNA oligonucleotides, LNA nucleotides and LNA analogue nucleotides are generally described in WO 99/14226 and subsequent applications, WO 00/56746, WO 00/56748, WO 00/66604, WO 00/125248, WO 02/28875, WO 2002/094250 and PCT/DK02/00488 all incorporated herein by reference.

In the context of the present application and claims, the inventors differentiate between "LNA nucleotides" and "LNA analogue nucleotides". An "LNA nucleotide" is a nucleotide of the Formula 1:

Formula 1

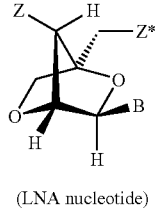

(LNA nucleotide)

Such LNA nucleotides are often referred to as "β-D-oxy-LNA".

B in Formula 1 constitutes a nucleobase. Nucleobases comprises naturally-occurring nucleobases as well as non-naturally occurring nucleobases. Illustrative examples of such nucleobase and selected among adenine, cytosine, 5-methylcytosine, isocytosine, pseudoisocytosine, guanine, thymine, uracil, 5-bromouracil, 5-propynyluracil, 5-propynyl-6-fluoroluracil, 5-methylthiazoleuracil, 6-aminopurine, 2-aminopurine, inosine, diaminopurine, 7-propyne-7-deazaadenine, 7-propyne-7-deazaguanine, and 2-chloro-6-aminopurine. Preferred examples of B are adenine, cytosine, 5-methylcytosine, isocytosine, pseudoisocytosine, guanine, thymine, uracil, 5-bromouracil, 5-propynyluracil, 6-aminopurine, 2-aminopurine, inosine, diaminopurine, and 2-chloro-6-aminopurine.

Z* in Formula 1 is selected from an internucleoside linkage and a terminal group, and Z in Formula 1 is selected from a bond to the internucleoside linkage of a preceding nucleotide/nucleoside and a terminal group, provided—of course—that only one of Z and Z* can be a terminal group.

The internucleoside linkage as a possible meaning of Z* means an internucleoside linkage to a succeeding nucleotide/nucleoside. Examples of internucleoside linkages are —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —S—P(O)$_2$—S—, —O—PO(R$^H$)—O—, —O—PO(OCH$_3$)—O—, —O—PO(NR$^H$)—O—, —O—PO(OCH$_2$CH$_2$S—R)—O—, —O—PO(BH$_3$)—O—, —O—PO(NHR$^H$)—O—, —O—P(O)$_2$—NR$^H$, —NR$^H$—P(O)$_2$—O—, —NR$^H$—CO—O—, —NR$^H$—CO—NR$^H$—, —O—CO—O—, —O—CO—NR$^H$—, —NR$^H$—CO—CH$_2$—, —O—CH$_2$—CO—NR$^H$—, —O—CH$_2$CH$_2$NR$^H$, —CO—NR$^H$—CH$_2$—, —CH$_2$NR$^H$—CO—, —O—CH$_2$—CH$_2$—S—, —S—CH$_2$—CH$_2$—O—, —S—CH$_2$—CH$_2$—S—, —CH$_2$—SO$_2$—CH$_2$—, —CH$_2$—CO—NR$^H$—, —O—CH$_2$—CH$_2$—NR$^H$—CO—, —CH$_2$—NCH$_3$—O—CH$_2$—, where R$^H$ is selected from hydrogen and C$_{1-4}$-alkyl. Preferred internucleoside linkages are —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, and —S—P(O)$_2$—S—. A particular feature of the present invention is that two LNA nucleotides are linked by a —O—P(O,S)—O— (phosphorothioate) group, i.e. the internucleoside linkage is preferably a phosphorothioate group.

In the present context, the term "C$_{1-4}$-alkyl" is intended to mean a linear or branched saturated hydrocarbon chain wherein the chain has from one to four carbon atoms, such as methyl, ethyl, n-propyl, isopropyl, n-butyl, isobutyl, sec-butyl and tert-butyl.

When the LNA nucleotide is the 5'-terminal nucleotide of the oligomeric compound, Z* is a terminal group; and if the LNA nucleotide is the 3'-terminal nucleotide of the oligomeric compound, Z is a terminal group. Such terminal groups are typically selected from hydrogen, azido, halogen, cyano, nitro, hydroxy, Prot-O—, Act-O—, mercapto, Prot-S—, Act-S—, C$_{1-6}$-alkylthio, amino, Prot-N(R$^H$)—, Act-N(R$^H$)—, mono- or di(C$_{1-6}$-alkyl)amino, optionally substituted C$_{1-6}$-alkoxy, optionally substituted C$_{1-6}$-alkyl, optionally substituted C$_{2-6}$-alkenyl, optionally substituted C$_{2-6}$-alkenyloxy, optionally substituted C$_{2-6}$-alkynyl, optionally substituted C$_{2-6}$-alkynyloxy, monophosphate, monothiophosphate, diphosphate, dithiophosphate triphosphate, trithiophosphate, DNA intercalators, photochemically active groups, thermochemically active groups, chelating groups, reporter groups, ligands, carboxy, sulphono, hydroxymethyl, Prot—O—CH$_2$—, Act—O—CH$_2$—, aminomethyl, Prot-N(R$^H$)—CH$_2$—, Act-N(R$^H$)—CH$_2$-, carboxymethyl, and sulphonomethyl, where Prot is a protection group for —OH, —SH, and —NH(R$^H$), respectively, Act is an activation group for —OH, —SH, and —NH(R$^H$), respectively, and R$^H$ is selected from hydrogen and C$_{1-6}$-alkyl. Preferred examples of terminal groups are hydrogen, azido, halogen, cyano, nitro, hydroxy, Prot-O—, Act-O—, mercapto, Prot-S—, Act-S—, C$_{1-6}$-alkylthio, amino, Prot-N(R$^H$)—, Act-N(R$^H$)—, mono- or di(C$_{1-6}$-alkyl)amino, optionally substituted C$_{1-6}$-alkoxy, optionally substituted C$_{1-6}$-alkyl, optionally substituted monophosphate, monothiophosphate, diphosphate, dithiophosphate triphosphate, and trithiophosphate, where Prot is a protection group for —OH, —SH, and —NH(R$^H$), respectively, Act is an activation group for —OH, —SH, and —NH (R$^H$), respectively, and R$^H$ is selected from hydrogen and C$_{1-6}$-alkyl.

Protection groups (Prot) of hydroxy (and sulphur) substituents comprises substituted trityl, such as 4,4'-dimethoxytrityloxy (DMT), 4-monomethoxytrityloxy (MMT), and trityloxy, optionally substituted 9-(9-phenyl)xanthenyloxy (pixyl), optionally substituted methoxytetra-hydropyranyloxy (mthp), silyloxy such as trimethylsilyloxy (TMS), triisopropylsilyloxy (TIPS), tert-butyldimethylsilyloxy (TBDMS), triethylsilyloxy, and phenyldimethylsilyloxy, tert-butylethers, acetals (including two hydroxy groups), acyloxy such as acetyl or halogen substituted acetyls, e.g. chloroacetyloxy or fluoroacetyloxy, isobutyryloxy, pivaloyloxy, benzoyloxy and substituted benzoyls, methoxymethyloxy (MOM), and benzyl ethers or substituted benzyl ethers such as 2,6-dichlorobenzyloxy (2,6-Cl$_2$Bzl). Preferred protection groups of hydroxy (and sulphur) substituents comprises substituted trityl, such as 4,4'-dimethoxytrityloxy (DMT), 4-monomethoxytrityloxy (MMT), optionally substituted 9-(9-phenyl)xanthenyloxy (pixyl), optionally substituted methoxytetrahydropyranyloxy (mthp), silyloxy such as trimethylsilyloxy (TMS), triisopropylsilyloxy (TIPS), tert-butyldimethylsilyloxy (TBDMS), triethylsilyloxy, and phenyldimethylsilyloxy, tert-butylethers, acetals (including two hydroxy groups), and acyloxy such as acetyl.

Illustrative examples of protecting groups of amino and amido groups are fluorenylmethoxy-carbonylamino (Fmoc), tert-butyloxycarbonylamino (BOC), trifluoroacetylamino, allyloxycarbonylamino (alloc, AOC), Z benzyloxycarbonylamino (Cbz), substituted benzyloxycarbonylaminos such as 2-chloro benzyloxycarbonylamino (2-ClZ), monomethoxytritylamino (MMT), dimethoxytritylamino (DMT), phthaloylamino, and 9-(9-phenyl)xanthenylamino (pixyl). Preferred examples are fluorenylmethoxycarbonylamino (Fmoc), tert-butyloxycarbonylamino (BOC), trifluoroacetylamino, allyloxycarbonylamino (alloc, AOC), monomethoxytritylamino (MMT), dimethoxytritylamino (DMT), phthaloylamino.

The group "Act" designates an activation group for —OH, —SH, and —NH(R$^H$), respectively, for coupling to further nucleotides, solid phases, proteins, etc. In the embodiment above, Act designates an activation group. Such activation groups are, e.g., selected from optionally substituted O-phosphoramidite, optionally substituted O-phosphotriester, optionally substituted O-phosphodiester, optionally substituted H-phosphonate, and optionally substituted O-phosphonate. In the present context, the term "phosphoramidite" means a group of the formula —P(OR$^x$)—N(R$^y$)$_2$, wherein R$^x$ designates an optionally substituted alkyl group, e.g. methyl, 2-cyanoethyl, or benzyl, and each of R$^y$ designate optionally substituted alkyl groups, e.g. ethyl or isopropyl, or the group —N(R$^y$)$_2$ forms a morpholino group (—N(CH$_2$CH$_2$)$_2$O). R$^x$ preferably designates 2-cyanoethyl and the two R$^y$ are preferably identical and designate isopropyl. Thus, an especially relevant phosphoramidite is N,N-diisopropyl-O-(2-cyanoethyl)phosphoramidite.

As mentioned above, the oligomeric compounds comprise LNA nucleotides, possibly in combination with nucleotides that are not LNA nucleotides. Such nucleotides include deoxyribonucleotides (DNA nucleotides), ribonucleotides (RNA nucleotides), nucleotide derivatives, LNA analogue nucleotides, nucleotide analogues (other than LNA), and PNA units, etc.

Nucleotide analogues and nucleotide derivatives are described in e.g. Freier & Altmann (Nucl. Acid Res., 1997, 25, 4429-4443) and Uhlmann (Curr. Opinion in Drug & Development (2000, 3(2): 293-213). Scheme 1 Illustrates selected examples hereof:

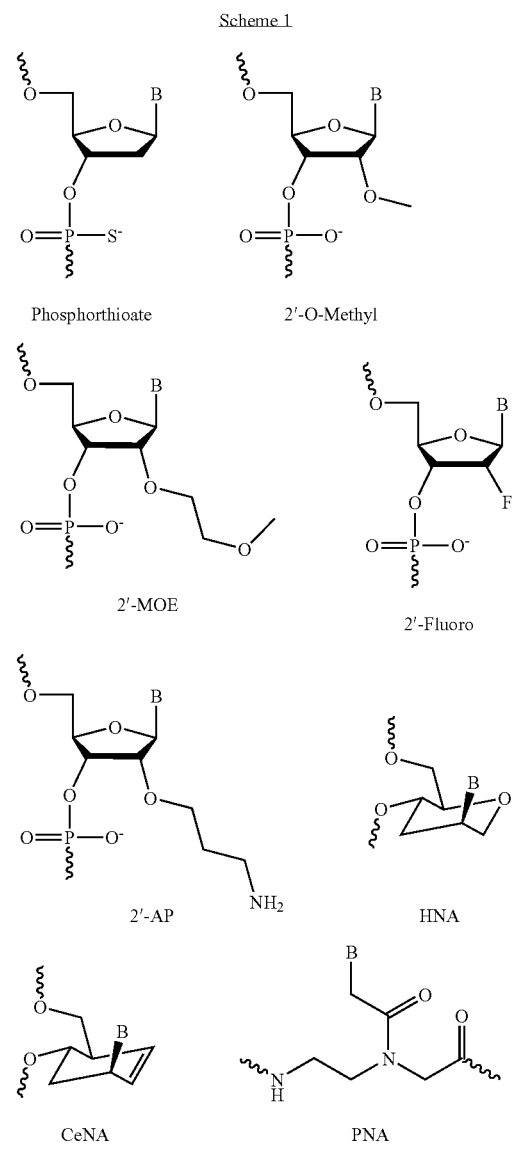

Scheme 1

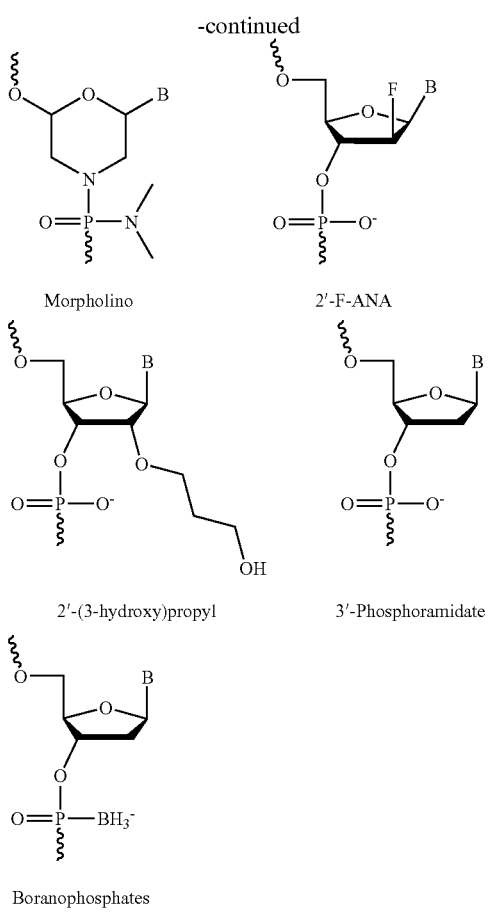

Morpholino

2'-F-ANA

2'-(3-hydroxy)propyl

3'-Phosphoramidate

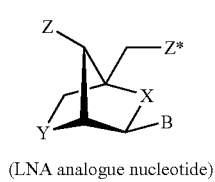

Boranophosphates

The term "LNA analogue nucleotide" refers to bicyclic nucleotide analogues as those generally described in WO 99/14226 and subsequent applications, WO 00/56746, WO 00/56748, WO 00/66604, WO 00/125248, WO 02/28875, WO 2002/094250 and WO 2003/006475 (PCT/DK02/00488) (cf. the above), excluding, however, the already described "LNA nucleotides".

Examples of a particular group of preferred LNA analogue nucleotides are exemplified with Formula 2:

Formula 2

(LNA analogue nucleotide)

In Formula 2, X and Y are independently selected from —O—, —S—, —N(H)—, —N(R)—, —CH$_2$— or —CH— (if part of a double bond), —CH$_2$—O—, —CH$_2$—S—, —CH$_2$—N(H)—, —CH$_2$—N(R)—, —CH$_2$—CH$_2$— or —CH$_2$—CH— (if part of a double bond), —CH═CH—, where R is selected from hydrogen and C$_{1-4}$-alkyl. The asymmetric groups may be found In either orientation. In preferred embodiments, X is oxygen and Y is selected from —O—, —S—, —N(H)—, and —N(R)—, noting that "LNA nucleotides" (X═O and Y═O) are not Included.

The oligomeric compound of the invention may further carry Z and Z* groups as those defined for the LNA nucleotides.

In Formula 2, the four chiral centers are shown in a fixed configuration. However, also comprised in this invention are compounds of the general Formula 2 in which the chiral centers are found in different configurations. Thus, each chiral center in Formula 2 can exist in either R or S configuration. The definition of R (rectus) and S (sinister) are described in the IUPAC 1974 Recommendations, Section E, Fundamental Stereochemistry: The rules can be found in Pure Appl. Chem. 45, 13-30, (1976) and in "Nomenclature of organic Chemistry" Pergamon, N.Y., 1979.

Particular examples of "LNA analogue nucleotides" are illustrated in by formulae I, II, III, IV, V, and VI:

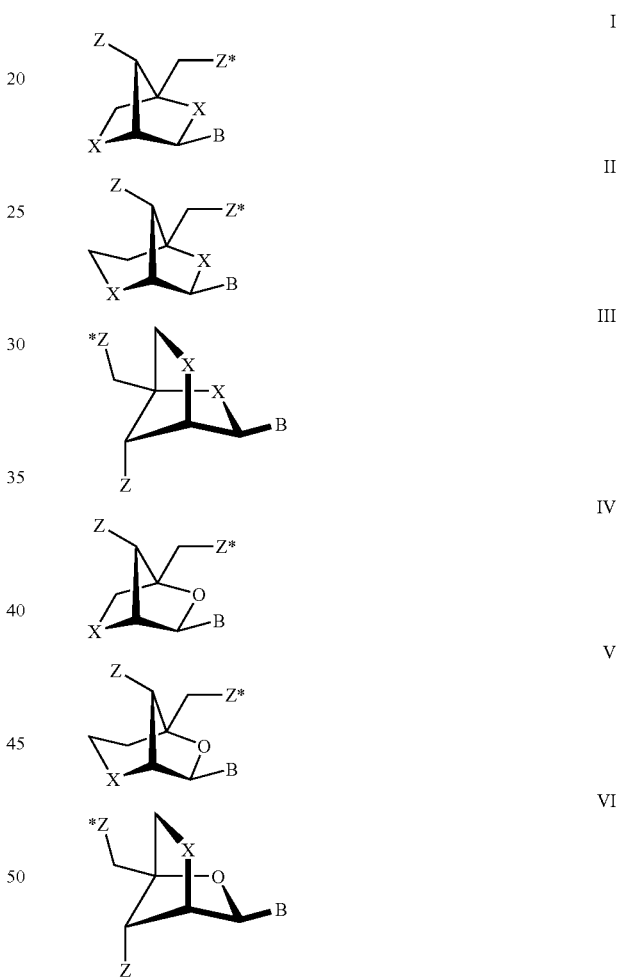

One example is the "thio-LNA" nucleotide, i.e. an LNA analogue nucleotide in which at least one of X in Formulae I, III, IV or VI is selected from —S— or —CH$_2$—S—. Such thio-LNA can be in both beta-D-configuration (I and IV) and alpha-L-configuration (III and VI), respectively.

Another example is the "amino-LNA" nucleotide, i.e. an LNA analogue nucleotide in which at least one of X in Formulae I, III, IV or VI is selected from —N(H)—, —N(R)—, —CH$_2$—N(H)—, —CH$_2$—N(R)—, where R is selected from hydrogen and C$_{1-4}$-alkyl. Such amino-LNA can be In both beta-D-configuration (I and IV) and alpha-L-configuration (III and VI), respectively.

A further example is the "ena-LNA" nucleotide, i.e. an LNA analogue nucleotide in which at least one of X in Formulae II or V is —CH$_2$—O—.

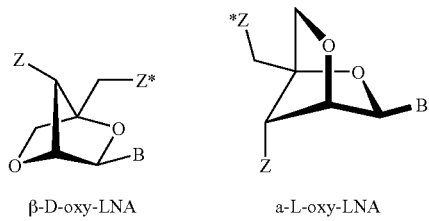

β-D-oxy-LNA     α-L-oxy-LNA

In a still further embodiment, the oligomeric compound comprises an "alpha-L-LNA" (i.e. "β-L-LNA") nucleotide, i.e. an LNA nucleotide as shown in Formulae III and VI.

This being said, the LNA nucleotide analogues, if present, are preferably selected from β-D-amino-LNA, β-D-thio-LNA and α-L-oxy-LNA, in particular all LNA nucleotide analogues, if present, are α-L-oxy-LNA.

As mentioned above, the present invention in particular relates to an oligomeric compound of 10-30 nucleobases in length which comprises a target binding domain that is specifically hybridizable to a region ranging from base position No. 1459 (5') to No. 1476 (3') of the human Bcl-2 mRNA, said target binding domain having the formula:

5'-[(DNA/RNA)$_{0-1}$-(LNA/LNA*)$_{2-7}$-(DNA/RNA/ LNA)$_{4-14}$-(LNA/LNA*)$_{2-7}$-(DNA/RNA)$_{0-1}$]-3' wherein "LNA" designates an LNA nucleotide and "LNA*" designates an LNA analogue nucleotide; and said target binding domain comprising at least two LNA nucleotides or LNA analogue nucleotides linked by a phosphorothioate group (—O—P(O,S)—O—).

Thus, the oligomeric compounds are 10-30 nucleobases in length, e.g. 10-25, such as 10-20, e.g. 10-18, or 10-16, nucleobases in length. The target binding domain thereof has a length of up to 18 nucleobases/nucleotides, because the target binding domain cannot be longer than the region to which it should be "specifically hybridizable". It will, however, be understood from the following, that the target binding domain does not need to be 18 nucleobases long, even not when the oligomeric compound is 18 nucleobases long or longer. As an example, the oligomeric compound may be 20 nucleobases long, and the target binding domain may then be 18, or 17, or 16, etc. nucleobases long. (It should then be understood that any nucleotides of the oligomeric compound, which are not part of the target binding domain, may bind to any nucleobases neighboring the specified region of the target mRNA.) It is, however, desirable that the target-binding domain represents a major portion of the oligomeric compound. Most preferably, the target binding domain constitutes 90%-100% of the length of the oligomeric compound that does not exceed 18 nucleotides, i.e. if the oligomeric compound has a length of up to 18 nucleotides, the target binding domain constitutes 90%-100% thereof, and if the oligomeric compound has a length of 19 or more nucleotides, the target binding domain has a length of 16-18 nucleotides (90%-100% of 18 nucleotides). More preferred, the target-binding domain constitutes the whole oligomeric compound.

As used herein, "hybridisation" means hydrogen bonding, which may be Watson-Crick, Hoogsteen, reversed Hoogsteen hydrogen bonding, etc. between complementary nucleoside or nucleotide bases. Watson and Crick showed approximately fifty years ago that deoxyribo nucleic acid (DNA) is composed of two strands which are held together in a helical configuration by hydrogen bonds formed between opposing complementary nucleobases In the two strands. The four nucleobases, commonly found In DNA are guanine (G), adenine (A), thymine (T) and cytosine (C) of which the G nucleobase pairs with C, and the A nucleobase pairs with T. In RNA, the nucleobase thymine is replaced by the nucleobase uracil (U), which similarly to the T nucleobase pairs with A. The chemical groups in the nucleobases that participate in standard duplex formation constitute the Watson-Crick face. Hoogsteen showed a couple of years later that the purine nucleobases (G and A) in addition to their Watson-Crick face have a Hoogsteen face that can be recognised from the outside of a duplex, and used to bind pyrimidine oligonucleotides via hydrogen bonding, thereby forming a triple helix structure.

The term "specifically hybridisable" means that the oligomeric compound in question is capable of binding sufficiently strong and specific to the target mRNA to provide the desired interference with the normal function of the target mRNA whilst leaving the function of non-target mRNAs unaffected. The relevant hybridisation and thereby interference with the function normally takes place at physiological conditions, i.e. at about 37° C. This does, however, not exclude that one or two mismatches can be present in the target binding domain. Preferably, the target binding domain includes no mismatches or at the most one mismatch (see further below).

As used herein, the terms "target mRNA" means the human Bcl-2 mRNA encoding human Bcl-2 protein.

As used herein, the term "modulation" means a decrease (e.g. inhibition) in the expression of the human Bcl-2 gene via binding of an oligomeric compound to the human Bcl-2 mRNA encoding blc-2 protein.

The "specific hybridisation" is obtained by binding of the target binding domain to the specified region of the target mRNA. It should be understood that the target binding domain does not need to bind to the full 18 nucleotide region of the target mRNA, in particular not if the oligomeric compound and thereby also the target binding domain has a length of less than 18 nucleobases. Preferably, however, the target binding domain binds to a stretch of at least 10 nucleobases, such as a stretch of in the range of 10-18, or 10-17, or 10-16, or 10-15, or 10-14, nucleobases of the specified region of the target mRNA.

It is generally preferred that a substantial number of the nucleotides links (more accurately links between nucleosides, i.e. internucleoside linkages) in the target binding domain are phosphorothioate groups (—O—P(O,S)—O—). More preferably, at least 70%, such as at least 80%, or at least 87%, or at least 93%, of the nucleotide links are phosphorothioate groups (—O—P(O,S)—O—). In a particular embodiment, all nucleotide links are phosphorothioate groups. In particular, all nucleotide links in the oligomeric compound are phosphorothioate groups.

In many embodiments, at least 3, such as at least 4, at least 5 or even at least 6, at least 7 or at least 8, of the nucleobases in the target binding domain are nucleobases of LNA nucleotides.

In further embodiments, at least 3, such as at least 4, at least 5 or even at least 6, at least 7 or at least 8, of the nucleobases in the target binding domain are nucleobases of LNA analogue nucleotides.

In preferred embodiments with reference to many of the specified sequences in Table 1, 10-50% of the nucleobases in the target binding domain are nucleobases of LNA nucleotides.

In some preferred designs, the two 5'-terminal nucleobases of said target binding domain are nucleobases of LNA nucleotides.

In other preferred designs, the two 5'-terminal nucleobases of said target binding domain are a nucleobase of a DNA or RNA nucleotide followed by a nucleobase of an LNA nucleotide, in particular a DNA or RNA nucleotide followed by two nucleobases of an LNA nucleotide.

In further preferred designs, the 3'-terminal nucleobase of said target binding domain is a nucleobase of a DNA or RNA nucleotide.

In a variant hereof, the two 3'-terminal nucleobases of said target binding domain are a nucleobase of a DNA or RNA nucleotide followed by a nucleobase of an LNA nucleotide.

In still further preferred designs, the two 3'-terminal nucleobases of said target binding domain are nucleobases of LNA nucleotides.

The oligomeric compounds have a target binding domain having a gapmer design, e.g. an LNA/(non-LNA)/LNA gapmer design. Particular variants of the gapmer construct defined above are target binding domains having a formula selected from:

5'-[(LNA/LNA*)$_{2-7}$-(DNA/RNA/LNA*)$_{4-14}$-LNA/LNA*$_{2-7}$]-3';

5'-[(LNA/LNA*)$_{2-7}$-(DNA/RNA/LNA*)$_{4-14}$-LNA/LNA*$_{2-7}$-(DNA/RNA)]-3';

5'-[(DNA/RNA)-(LNA/LNA*)$_{2-7}$-(DNA/RNA/LNA*)$_{4-14}$-LNA/LNA*$_{2-7}$]-3'; and

5'-[(DNA/RNA)-(LNA/LNA*)$_{2-7}$-(DNA/RNA/LNA*)$_{4-14}$-LNA/LNA*$_{2-7}$-(DNA/RNA)]-3'.

It is believed that the four types of gapmers mentioned above will lead to the same type of active species, namely a gapmer of the type 5'-[(LNA/LNA*)$_{2-7}$-(DNA/RNA/LNA*)$_{4-14}$-LNA/LNA*$_{2-7}$]-3', after cleavage of the 5'- or 3'-DNA moiety by exonucleases, cf. Example 15. Hence, as SEQ ID NO: 15 is a particularly preferred gapmer (and discrete compound) It follows that SEQ ID NO: 29 is believed to be equally interesting. Similarly, SEQ ID NO: 8 is a particularly preferred gapmer (and discrete compound) it follows that SEQ ID NO: 35 is believed to be equally interesting.

A particular design is the one where the target binding domain has the formula 5'-[(LNA/LNA*)$_{2-7}$-(DNA/RNA/LNA*)$_{4-14}$-LNA/LNA*$_{2-7}$-(DNA/RNA)]-3', such as 5'-[(LNA/LNA*)$_{2-5}$-(DNA/RNA/LNA*)$_{7-12}$-LNA/LNA*$_{2-5}$-(DNA/RNA)]-3', in particular 5'-[(LNA/LNA*)$_{2-4}$-(DNA/RNA/LNA*)$_{10-12}$-LNA/LNA*$_{2-4}$-(DNA/RNA)]-3'.

The expression "(LNA/LNA*)" means that the segment in question (i.e. a segment comprising 2-7 nucleotides) may include LNA nucleotides, LNA analogue nucleotides, or both. By analogy, the segment "(DNA/RNA/LNA*)" may include deoxyribonucleotides (DNA nucleotides), ribonucleotides (RNA nucleotides) and LNA analogue nucleotides, and combinations thereof. The segment "(DNA/RNA)" may include deoxyribonucleotides (DNA nucleotides) and ribonucleotides (RNA nucleotides), or both.

It is believed that the -(DNA/RNA/LNA*)$_{4-14}$-subsegment should be able to recruit RNaseH, for what reason this subsegment preferably consists of DNA nucleotides or LNA analogue nucleotides In the form of α-L-LNA nucleotides, In particular of DNA nucleotides. Although defined as a subsegment of a length of from 4 to 14 nucleotides, it is believed that a length of in the range from 7 to 12 nucleobases, such as from 10 to 12 nucleobases, In particular 11 nucleobases, leads to particularly useful gapmers, cf. Table 1.

Thus, a more particular design is the one where the target binding domain has the formula 5'-[(LNA/LNA*)$_{2-7}$-(DNA/α-L-LNA)$_{5-14}$-LNA/LNA*$_{2-7}$-(DNA/RNA)]-3', such as 5'-[(LNA/LNA*)$_{2-5}$-(DNA/α-L-LNA)$_{7-12}$-LNA/LNA*$_{2-5}$-(DNA/RNA)]-3', in particular 5'-[(LNA/LNA*)$_{2-4}$-(DNA/α-L-LNA)$_{10-12}$-LNA/LNA*$_{2-4}$-(DNA/RNA)]-3'.

A further particularly interesting design is the one where the target binding domain has the formula 5'-[LNA$_{2-7}$-(DNA)$_{4-14}$-LNA$_{2-7}$-(DNA/RNA)]-3', such as 5'-[LNA$_{2-5}$-(DNA)$_{7-12}$-LNA$_{2-5}$-(DNA/RNA)]-3', in particular 5'-[LNA$_{2-4}$-(DNA)$_{10-12}$-LNA$_{2-4}$-(DNA/RNA)]-3'. A still further particularly interesting design is the one where the target binding domain has the formula 5'-[LNA$_{2-7}$-(DNA)$_{5-14}$-LNA$_{2-7}$-(RNA)]-3' or 5'-[LNA$_{2-7}$-(DNA)$_{5-14}$-LNA$_{2-7}$-(DNA)]-3' or 5'-[LNA$_{2-7}$-(DNA/α-L-LNA)$_{5-14}$-LNA$_{2-7}$-(RNA)]-3' or 5'-[LNA$_{2-7}$-(DNA/α-L-LNA)$_{5-14}$-LNA$_{2-7}$-(DNA)]-3', such as 5'-[LNA$_{2-5}$-(DNA)$_{7-12}$-LNA$_{2-5}$-(RNA)]-3' or 5'-[LNA$_{2-5}$-(DNA)$_{7-12}$-LNA$_{2-5}$-(DNA)]-3' or 5'-[LNA$_{2-5}$-(DNA/α-L-LNA)$_{7-12}$-LNA$_{2-5}$-(RNA)]-3' or 5'-[LNA$_{2-5}$-(DNA/α-L-LNA)$_{7-12}$-LNA$_{2-5}$-(DNA)]-3', in particular 5'-[LNA$_{2-4}$-(DNA)$_{10-12}$-LNA$_{2-4}$-(RNA)]-3' or 5'-[LNA$_{2-4}$-(DNA)$_{10-12}$-LNA$_{2-4}$-(DNA)]-3' or 5'-[LNA$_{2-4}$-(DNA/α-L-LNA)$_{10-12}$-LNA$_{2-4}$-(RNA)]-3' or 5'-[LNA$_{2-4}$-(DNA/α-L-LNA)$_{10-12}$-LNA$_{2-4}$-(DNA)]-3'.

In another embodiment, the target binding domain has the formula 5'-[(DNA/RNA)-(LNA/LNA*)$_{2-7}$-(DNA/RNA/LNA*)$_{4-14}$-LNA/LNA*$_{2-7}$-(DNA/RNA)]-3', in particular the formula 5'-[(DNA/RNA)-LNA$_{2-7}$-(DNA)$_{4-14}$-LNA$_{2-7}$-(DNA/RNA)]-3', e.g. 5'-[(DNA/RNA)-(LNA/LNA*)$_{2-5}$-(DNA/RNA/LNA*)$_{7-12}$-LNA/LNA*$_{2-5}$-(DNA/RNA)]-3', In particular the formula 5'-[(DNA/RNA)-LNA$_{2-5}$-(DNA)$_{7-12}$-LNA$_{2-5}$-(DNA/RNA)]-3', or 5'-[(DNA/RNA)-(LNA/LNA*)$_{2-4}$-(DNA/RNA/LNA*)$_{10-12}$-LNA/LNA*$_{2-4}$-(DNA/RNA)]-3', in particular the formula 5'-[(DNA/RNA)-LNA$_{2-4}$-(DNA)$_{10-12}$-LNA$_{2-4}$-(DNA/RNA)]-3'. A still further particularly interesting design is the one where the target binding domain has the formula 5'-[(DNA)-LNA$_{2-7}$-(DNA)$_{5-14}$-LNA$_{2-7}$-(RNA)]-3' or 5'-[(DNA)-LNA$_{2-7}$-(DNA)$_{5-14}$-LNA$_{2-7}$-(DNA)]-3' or 5'-[(DNA)-LNA$_{2-7}$-(DNA/α-L-LNA)$_{5-14}$-LNA$_{2-7}$-(RNA)]-3' or 5'-[(DNA)-LNA$_{2-7}$-(DNA/α-L-LNA)$_{5-14}$-LNA$_{2-7}$-(DNA)]-3' or 5'-[(RNA)-LNA$_{2-7}$-(DNA)$_{5-14}$-LNA$_{2-7}$-(RNA)]-3' or 5'-[(RNA)-LNA$_{2-7}$-(DNA)$_{5-14}$-LNA$_{2-7}$-(DNA)]-3' or 5'-[(RNA)-LNA$_{2-7}$-(DNA/α-L-LNA)$_{5-14}$-LNA$_{2-7}$-(RNA)]-3' or 5'-[(RNA)-LNA$_{2-7}$-(DNA/α-L-LNA)$_{5-14}$-LNA$_{2-7}$-(DNA)]-3', such as 5'-[(DNA)-LNA$_{2-5}$-(DNA)$_{7-12}$-LNA$_{2-5}$-(RNA)]-3' or 5'-[(DNA)-LNA$_{2-5}$-(DNA)$_{7-12}$-LNA$_{2-5}$-(DNA)]-3' or 5'-[(DNA)-LNA$_{2-5}$-(DNA/α-L-LNA)$_{7-12}$-LNA$_{2-5}$-(RNA)]-3' or 5'-[(DNA)-LNA$_{2-5}$-(DNA/α-L-LNA)$_{7-12}$-LNA$_{2-5}$-(DNA)]-3' or 5'-[(RNA)-LNA$_{2-5}$-(DNA)$_{7-12}$-LNA$_{2-5}$-(RNA)]-3' or 5'-[(RNA)-LNA$_{2-5}$-(DNA)$_{7-12}$-LNA$_{2-5}$-(DNA)]-3' or 5'-[(RNA)-LNA$_{2-5}$-(DNA/α-L-LNA)$_{7-12}$-LNA$_{2-5}$-(RNA)]-3' or 5'-[(RNA)-LNA$_{2-5}$-(DNA/α-L-LNA)$_{7-12}$-LNA$_{2-5}$-(DNA)]-3', in particular 5'-[(DNA)-LNA$_{2-4}$-(DNA)$_{10-12}$-LNA$_{2-4}$-(RNA)]-3' or 5'-[(DNA)-LNA$_{2-4}$-(DNA)$_{10-12}$-LNA$_{2-4}$-(DNA)]-3' or 5'-[(DNA)-LNA$_{2-4}$-(DNA/α-L-LNA)$_{10-12}$-LNA$_{2-4}$-(RNA)]-3' or 5'-[(DNA)-LNA$_{2-4}$-(DNA/α-L-LNA)$_{10-12}$-LNA$_{2-4}$-(DNA)]-3' or 5'-[(RNA)-LNA$_{2-4}$-(DNA)$_{10-12}$-LNA$_{2-4}$-(RNA)]-3' or 5'-[(RNA)-LNA$_{2-4}$-(DNA)$_{10-12}$-LNA$_{2-4}$-(DNA)]-3' or 5'-[(RNA)-LNA$_{2-4}$-(DNA/α-L-LNA)$_{10-12}$-LNA$_{2-4}$-(RNA)]-3' or 5'-[(RNA)-LNA$_{2-4}$-(DNA/α-L-LNA)$_{10-12}$-LNA$_{2-4}$-(DNA)]-3'.

In a further embodiment, the target binding domain has the formula 5'-[(DNA/RNA)-(LNA/LNA*)$_{2-7}$-(DNA/RNA/LNA*)$_{4-14}$-LNA/LNA*$_{2-7}$]-3', in particular the formula 5'-[(DNA/RNA)-LNA$_{2-7}$-(DNA)$_{4-14}$-LNA$_{2-7}$]-3', such as 5'-

[(DNA/RNA)-(LNA/LNA*)$_{2-5}$-(DNA/RNA/LNA*)$_{7-12}$-LNA/LNA*$_{2-5}$]-3', in particular the formula 5'-[(DNA/RNA)-LNA$_{2-5}$-(DNA)$_{7-12}$-LNA$_{2-5}$]-3', or 5'-[(DNA/RNA)-(LNA/LNA*)$_{2-4}$-(DNA/RNA/LNA*)$_{10-12}$-LNA/LNA*$_{2-4}$]-3', in particular the formula 5'-[(DNA/RNA)-LNA$_{2-4}$-(DNA)$_{10-12}$-LNA$_{2-4}$]-3'. A still further particularly interesting design is the one where the target binding domain has the formula 5'-[(DNA)-LNA$_{2-7}$-(DNA)$_{5-14}$-LNA$_{2-7}$]-3' or 5'-[(DNA)-LNA$_{2-7}$-(DNA/α-L-LNA)$_{5-14}$-LNA$_{2-7}$]-3' or 5'-[(RNA)-LNA$_{2-7}$-(DNA)$_{5-14}$-LNA$_{2-7}$]-3' or 5'-[(RNA)-LNA$_{2-7}$-(DNA/α-L-LNA)$_{5-14}$-LNA$_{2-7}$]-3', such as 5'-[(DNA)-LNA$_{2-5}$-(DNA)$_{7-12}$-LNA$_{2-5}$]-3' or 5'-[(DNA)-LNA$_{2-5}$-(DNA/α-L-LNA)$_{7-12}$-LNA$_{2-5}$]-3' or 5'-[(RNA)-LNA$_{2-5}$-(DNA)$_{7-12}$-LNA$_{2-5}$]-3' or 5'-[(RNA)-LNA$_{2-5}$-(DNA/α-L-LNA)$_{7-12}$-LNA$_{2-5}$]-3', in particular 5'-[(DNA)-LNA$_{2-4}$-(DNA)$_{10-12}$-LNA$_{2-4}$]-3' or 5'-[(DNA)-LNA$_{2-4}$-(DNA/α-L-LNA)$_{10-12}$-LNA$_{2-4}$]-3' or 5'-[(RNA)-LNA$_{2-4}$-(DNA)$_{10-12}$-LNA$_{2-4}$]-3' or 5'-[(RNA)-LNA$_{2-4}$-(DNA/α-L-LNA)$_{10-12}$-LNA$_{2-4}$]-3'.

In a still further embodiment, the target binding domain has the formula 5'-[(LNA/LNA*)$_{2-7}$-(DNA/RNA/LNA*)$_{4-14}$-LNA/LNA*$_{2-7}$]-3', in particular the formula 5'-[LNA$_{2-7}$-(DNA)$_{4-14}$-LNA$_{2-7}$]-3', such as 5'-[(LNA/LNA*)$_{2-5}$-(DNA/RNA/LNA*)$_{7-12}$-LNA/LNA*$_{2-5}$]-3' in particular the formula 5'-[LNA$_{2-5}$-(DNA)$_{7-12}$-LNA$_{2-5}$]-3', or 5'-[(LNA/LNA*)$_{2-4}$-(DNA/RNA/LNA*)$_{10-12}$-LNA/LNA*$_{2-4}$]-3', in particular the formula 5'-[LNA$_{2-4}$-(DNA)$_{10-12}$-LNA$_{2-4}$]-3'. A still further particularly interesting design is the one where the target binding domain has the formula 5'-[LNA$_{2-7}$-(DNA)$_{5-14}$-LNA$_{2-7}$]-3' or 5'-[LNA$_{2-7}$-(DNA/α-L-LNA)$_{5-14}$-LNA$_{2-7}$]-3', such as 5'-[LNA$_{2-5}$-(DNA)$_{7-12}$-LNA$_{2-5}$]-3' or 5'-[LNA$_{2-5}$-(DNA/α-L-LNA)$_{7-12}$-LNA$_{2-5}$]-3', in particular 5'-[LNA$_{2-4}$-(DNA)$_{10-12}$-LNA$_{2-4}$]-3' or 5'-[LNA$_{2-4}$-(DNA/α-L-LNA)$_{10-12}$-LNA$_{2-4}$]-3'.

In some embodiment, the oligomeric compounds also comprise LNA analogues nucleotides (designated herein as "LNA*"). In particular 10-100% or 0-90%, e.g. 10-50%, of the nucleobases in the target binding domain are nucleobases of LNA analogue nucleotides (LNA*).

In a variant hereof, the target binding domain has the formula 5'-[(LNA*)$_{2-7}$-(DNA/RNA/LNA*)$_{4-14}$-LNA*$_{2-7}$-(DNA/RNA)]-340 , in particular 5'-[LNA*$_{2-7}$-(DNA)$_{4-14}$-LNA*$_{2-7}$-(DNA/RNA)]-3', such as 5'-[(LNA*)$_{2-5}$-(DNA/RNA/LNA*)$_{7-12}$-LNA*$_{2-5}$(DNA/RNA)]-3' in particular 5'-[LNA*$_{2-5}$-(DNA)$_{7-12}$-LNA*$_{2-5}$-(DNA/RNA)]-3', or 5'-[(LNA*)$_{2-4}$-(DNA/RNA/LNA*)$_{10-12}$LNA*$_{2-4}$(DNA/RNA)]-3', in particular 5'-[LNA*$_{2-4}$-(DNA)$_{10-12}$-LNA*$_{2-4}$-(DNA/RNA)]-3'.

As mentioned above, the oligomeric compound should be specifically hybridisable to the specified region of the target mRNA. More particularly, the target binding domain is complementary to the part of the region ranging from base position No. 1459 (5') to No. 1476 (3') of the human Bcl-2 mRNA to which it specifically hybridizes, with the possible exception of up to 2 non-complementary nucleobases.

In the context of the present invention, the term "complementary" refers to the capacity for precise pairing between nucleotides of the relevant region of the target mRNA and the nucleotides of the target binding domains. For example, if a nucleotide at a certain position of the target mRNA is capable of hydrogen bonding with a nucleotide of the target binding domain, then the target mRNA and the target binding domain are considered to be complementary to each other at that position. (It should again be understood from the above, the target binding domain is one that corresponds to the specified region of human Bcl-2 mRNA, or a shorter fragment thereof.) The term "non-complementary nucleobases" of course refers to the situation where the nucleobase of a particular nucleotide is not "complementary".

In one embodiment, the target binding domain is complementary to the part of the region ranging from base position No. 1459 (5') to No. 1476 (3') of the human Bcl-2 mRNA to which it specifically hybridizes.

Examples of preferred compounds within this embodiment are those that comprise a target binding domain selected from the group consisting of SEQ ID NOS: 1, 2, 3, 4, 5, 6, 7, 8 (and 35), 12, 13, 14, 41, 42, 43, 44, 45, 46, 47, 48, 49, 50, 51, and 52, in particular SEQ ID NO: 8 (and 35). In one variant, the target binding domain is SEQ ID NO: 8. In another variant, the target binding domain is SEQ ID NO: 35.

More preferred are those where the compound is selected from the group consisting of SEQ ID NOS: 1, 2, 3, 4, 5, 6, 7, 8 (and 35), 12, 13, 14, 41, 42, 43, 44, 45, 46, 47, 48, 49, 50, 51, and 52, in particular SEQ ID NO: 8 (and 35). In one variant, the compound is SEQ ID NO: 8. In another variant, the compound is SEQ ID NO: 35.

In another embodiment, the target binding domain is complementary to the part of the region ranging from base position No. 1459 (5') to No. 1476 (3') of the human Bcl-2 mRNA to which it specifically hybridizes, with the exception of 1-2 non-complementary nucleobases, in particular with the exception of 1 non-complementary nucleobase. Thus, up to two mismatches (non-complementary nucleobases) are tolerated, however, most often only one mismatch is Introduced. Such mismatches most often exist in a DNA/RNA/LNA* segments of an oligomeric compound, e.g. in the DNA/RNA/LNA* segment of a compound having a target binding domain comprising a segment of the formula 5'-[(LNA/LNA*)$_{2-7}$-(DNA/RNA/LNA*)$_{4-14}$-LNA/LNA*$_{2-7}$-(DNA/RNA)]-3'.

In one variant hereof, the target binding domain comprises a GCGXGCGC subsequence, wherein X is not T (thymine). In particular X is C (cytosine), or X is A (adenine), or X is G (guanine).

In another variant hereof, the target binding domain comprises a CCCAXCGT subsequence, wherein X is not G (guanine). In particular X is A (adenine), or X is T (thymine), or X is C (cytosine).

In still another variant hereof, the target binding domain comprises a CAGXGTG subsequence, wherein X is not C (cytosine). In particular X is A (adenine), or X is T (thymine), or X Is G (guanine).

In still another variant hereof, the target binding domain comprises a AGCXTGC subsequence, wherein X is not G (guanine). In particular X is A (adenine), or X is T (thymine), or X is C (cytosine).

Examples of preferred compounds within this embodiment are those that comprise a target binding domain selected from the group consisting of SEQ ID NO: 15 (and 29), 17, 18, 19, 21, 22, 23, 24, 25, 26, 27, 28, 53, 54 and 55, in particular SEQ ID NO: 15 (and 29). In one variant, the target binding domain is SEQ ID NO: 15. In another variant, the target binding domain is SEQ ID NO: 29.

More preferred are those where the compound is selected from the group consisting of SEQ ID NOS: 15 (and 29), 17, 18, 19, 21, 22, 23, 24, 25, 26, 27, 28, 53, 54 and 55, in particular SEQ ID NO: 15 (and 29). In one variant, the compound is SEQ ID NO: 15. In another variant, the compound is SEQ ID NO: 29.

This being said, it is currently believed that the oligomeric compound SEQ ID NO: 8 (and also 35) and the oligomeric compound SEQ ID NO: 15 (and also 29) each provide significant advantages over the oblimersen sodium compound (SEQ ID NO: 56; reference) with respect to the desirable biological effects, cf. the examples.

Figure 11:
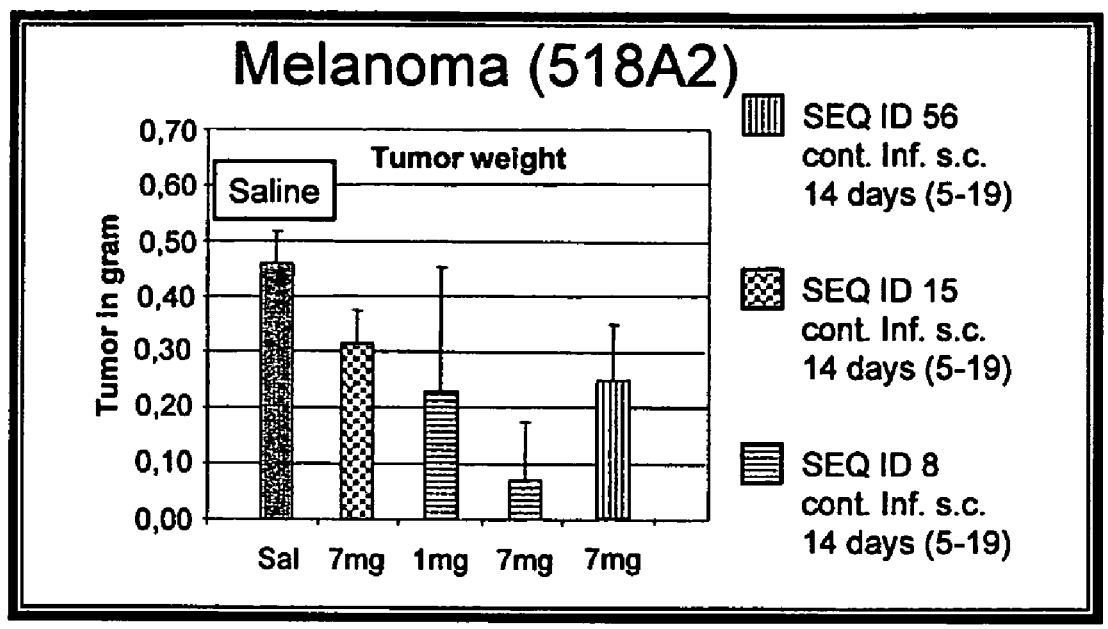
FIG. 11 shows an improved in viva reduction of tumour weight in a melanoma 518A2 scid mice xenograft model when administering 7 mg/kg of the SEQ ID NO: 8 i.p. for 14 days and compared to the same dosage of SEQ ID NO: 56 (reference). SEQ ID NO: 8 shows equal anti-tumour activity when administered at a 7-fold lower dose than SEQ ID NO: 56 (reference).

The present inventors have i.a. shown an improved in vivo reduction of tumour weight in a melanoma 518A2 scid mice xenograft model when administering 7 mg/kg of the SEQ ID NO: 8 i.p. for 14 days and compared to the same dosage of SEQ ID NO: 56 (reference), cf. FIG. 11. SEQ ID NO: 8 shows equal anti-tumour activity when administered at a 7-fold lower dose than SEQ ID NO: 56 (reference).

Figure 13:
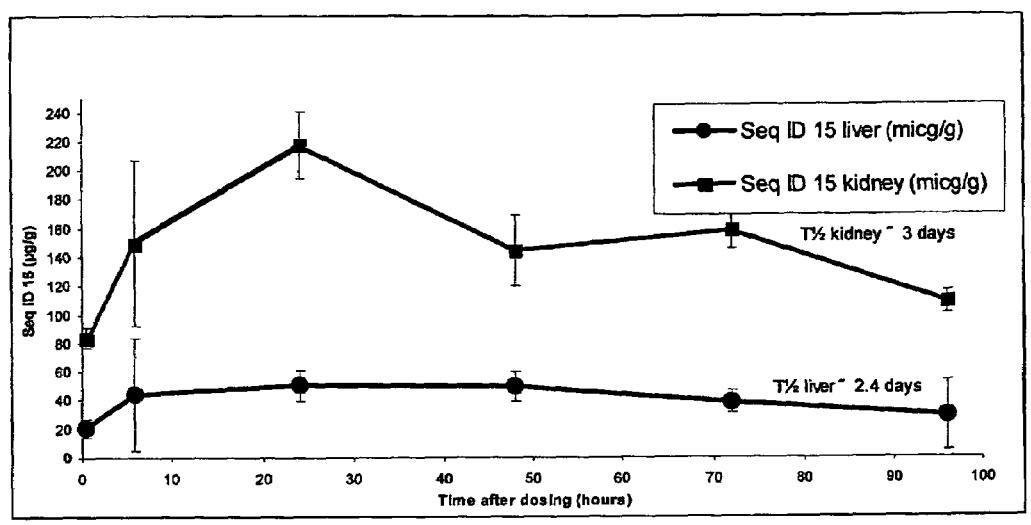
FIG. 13 shows levels of SEQ ID NO: 15 in liver and kidney from NMRI mice after single dose i.v. adm. (25 mg/kg). The half-life ($T_{1/2}$) of the active compound SEQ ID NO: 15 is found to be approximately 3 days in both liver and kidney. This Implies that dosage regimes of optimal biological doses of SEQ ID NO: 15 could be less frequent than continuous infusion and daily dosing.

In FIG. 13, the levels of SEQ ID NO: 15 in liver and kidney from NMRI mice after single dose i.v. adm. (25 mg/kg) is shown. The half-life ($T_{1/2}$) of the active compound SEQ ID NO: 15 is found to be approximately 3 days in both liver and kidney. This implies that dosage regimes of optimal biological doses of SEQ ID NO: 15 could be less frequent than continuous infusion and dally dosing.

Figure 7A:
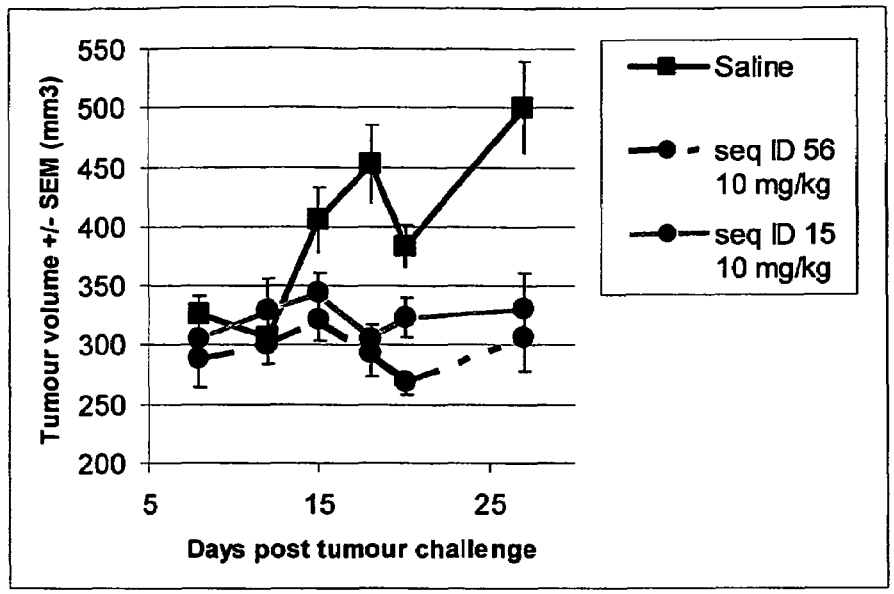
FIG. 7A shows an effective in vivo reduction of tumour volume using SEQ ID NO: 15 compared to SEQ ID NO: 56 (reference) in a prostate PC3 atymic nude mice xenograft model. The compounds were administered i.p. at 10 mg/kg for 14 days. Mytomycin C at 2 mg/kg dosed i.p. for 14 days was used as a positive control. Tumour growth was monitored for additional 8 days post treatment.
Figure 7B:
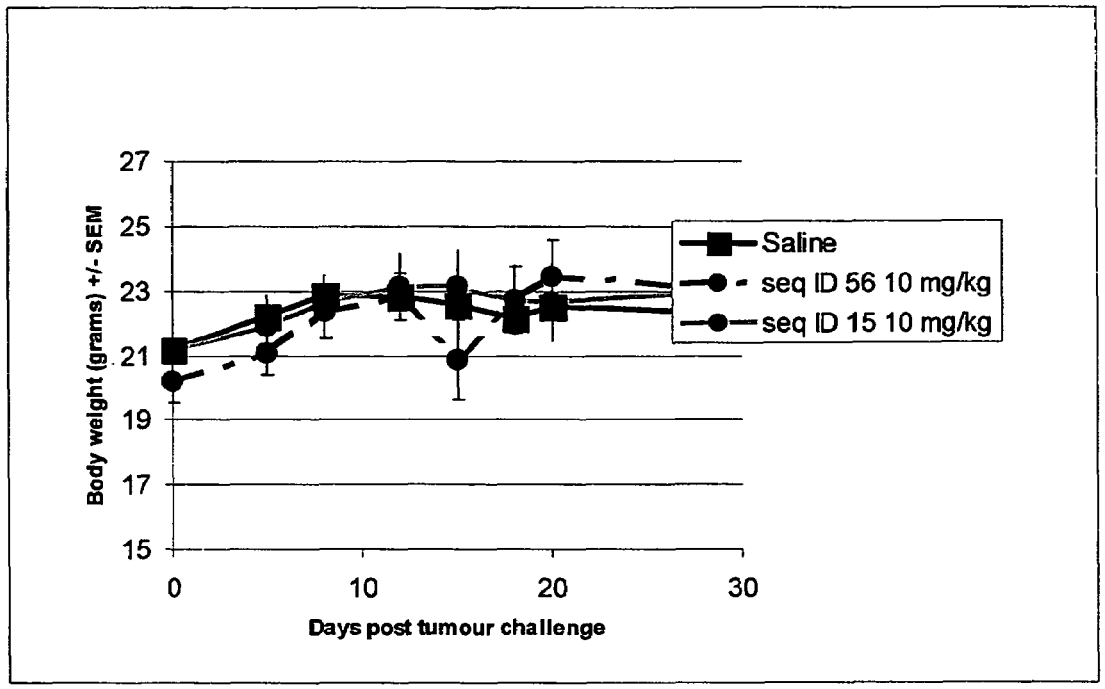
FIG. 7B shows that there was no significant loss in body weight when administering SEQ ID NO: 15 in a prostate PC3 atymic nude mice xenograft model. SEQ ID NO: 56 (reference) at 10 mg/kg and the positive control Mytomycin C at 2 mg/kg showed a similar pattern.
Figure 7C:
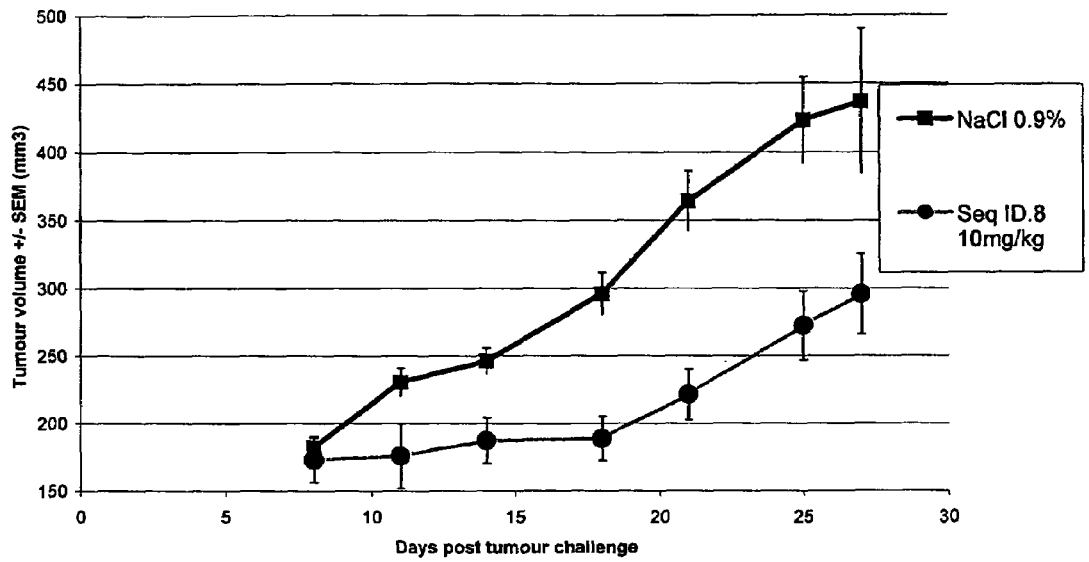
FIG. 7C: shows an effective in vivo reduction of tumour volume using SEQ ID NO: 8 compared to the saline control in a prostate PC3 atymic nude mice xenograft model. The compounds were administered i.p. at 10 mg/kg for 14 days (Day 5-19).
Figure 7D:
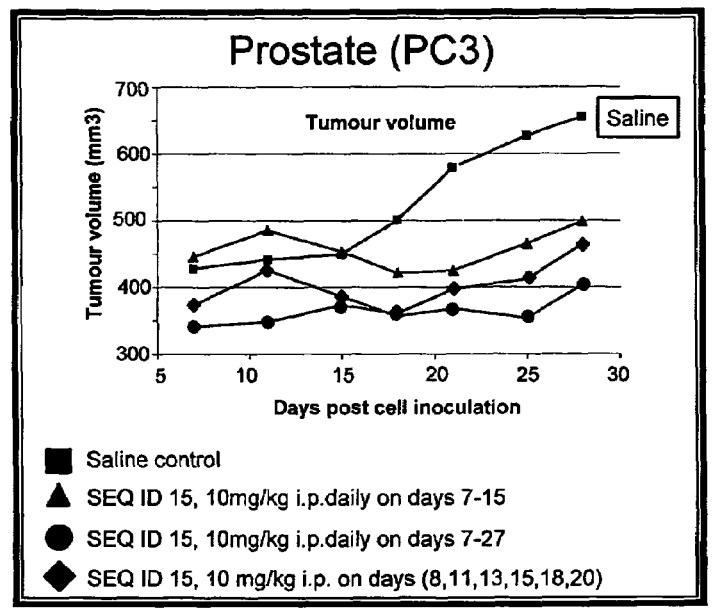
FIG. 7D shows an effective in vivo reduction of tumour volume using SEQ ID NO: 15 administered daily on days 7-15 or on days 8, 11, 13, 15, 18, 20 compared to the saline control in a prostate PC3 atymic nude mice xenograft model. The compounds were administered i.p. at 10 mg/kg for 14 days. Tumour growth was monitored for additional 8 days post treatment.
Figure 8A:
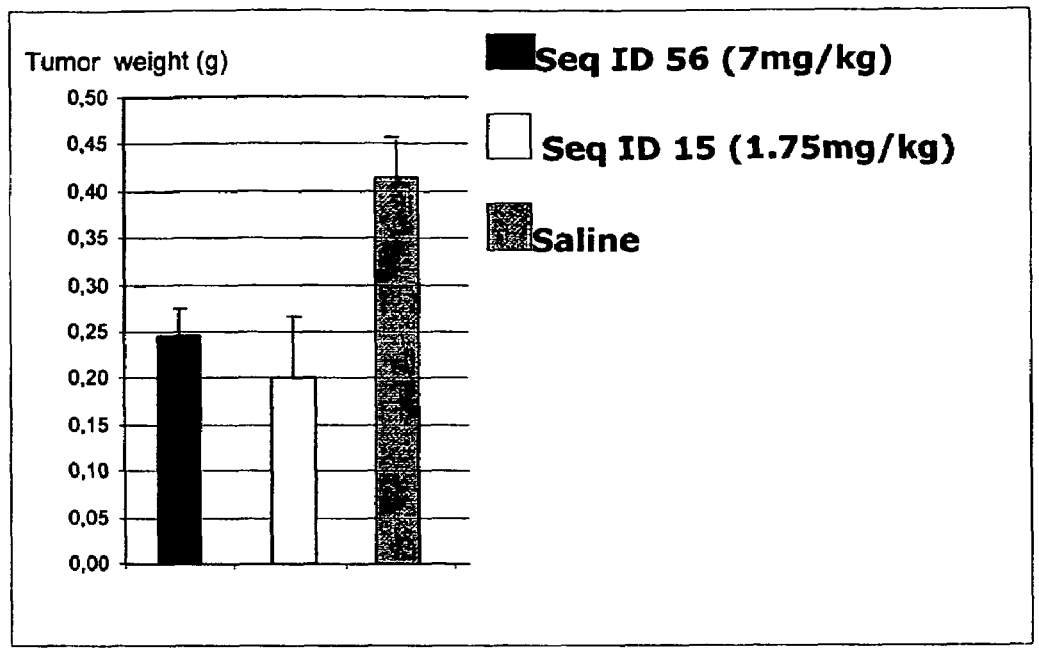
FIG. 8A shows comparable in vivo reduction of tumour weight (grams) administering 1.75 mg/kg for 14 days i.p. in a melanoma 518A2 scid mice xenograft model of SEQ ID NO: 15 compared to a 4 times higher dosage of SEQ ID NO: 56 (reference).
Figure 8B:
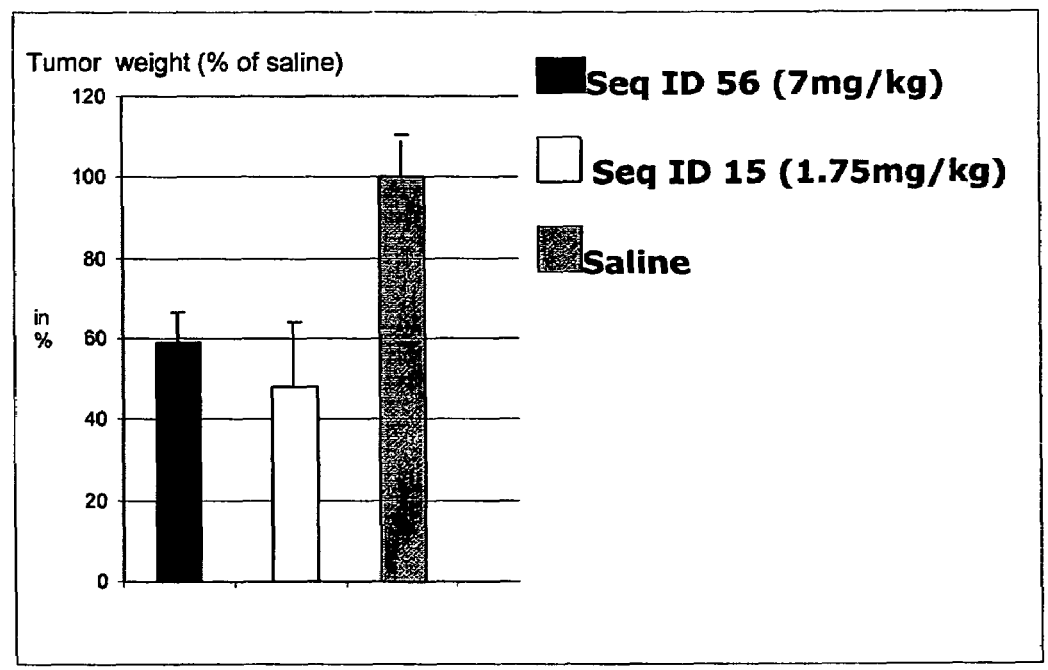
FIG. 8B shows results from the same experiment as in FIG. 8A, but the results are presented in % tumour reduction and not in gram.
Figure 9:
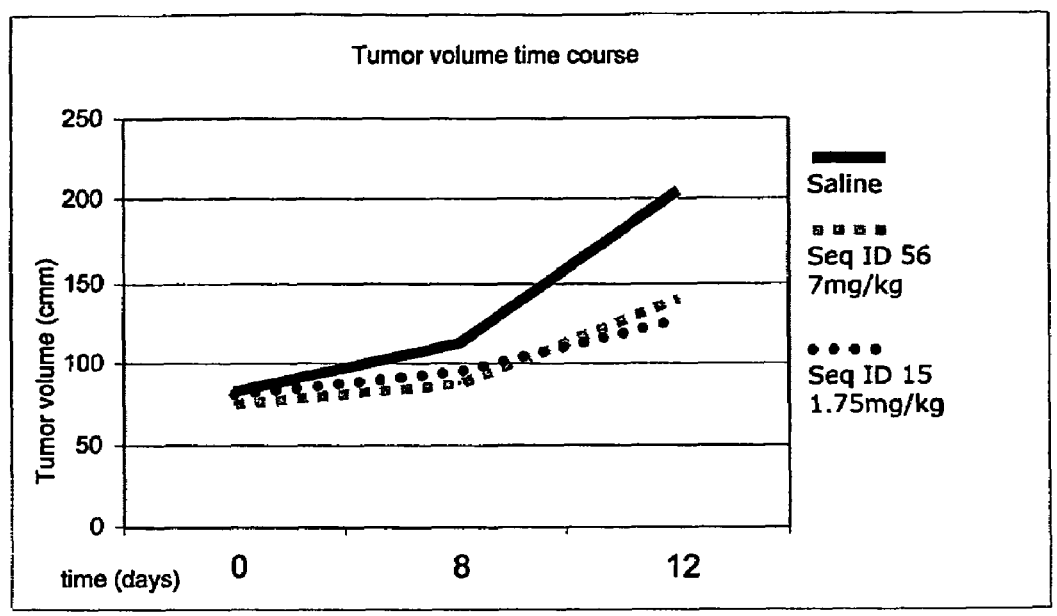
FIG. 9 shows a comparable in vivo reduction of tumour volume when administering 1.75 mg/kg of the SEQ ID NO: 15 i.p. for 14 days in a melanoma 518A2 scid mice xenograft model compared a 4 times higher dosage of SEQ ID NO: 56 (reference).
Figure 10A:
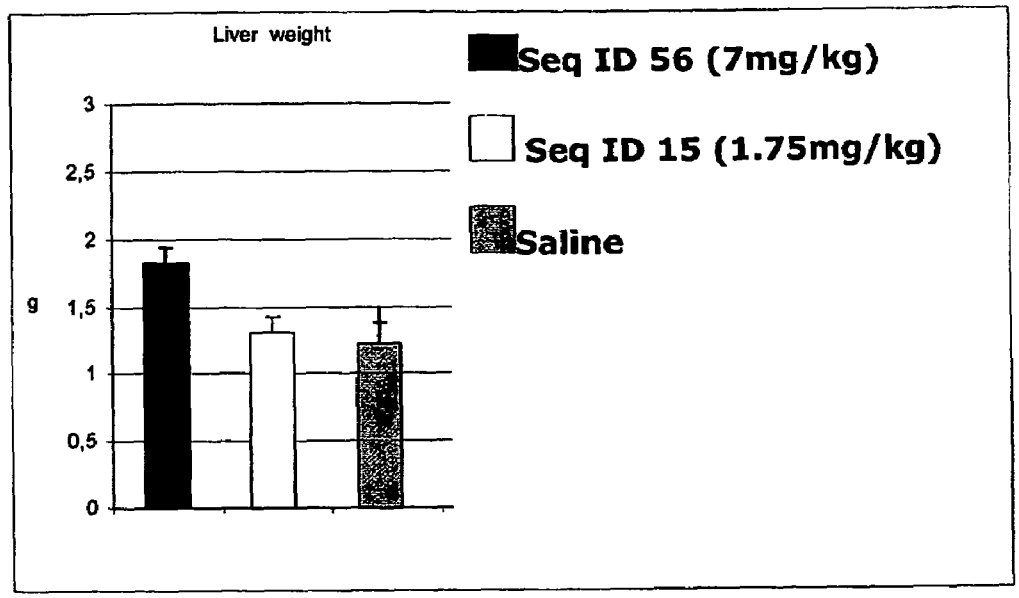
FIG. 10A shows no increase in liver size when administering 1.75 mg/kg SEQ ID NO: 15 i.p. for 14 days in a melanoma 518A2 scid mice xenograft compared to the saline control. SEQ ID NO: 56 (reference) at 7 mg/kg gave an increase in liver size.
Figure 10B:
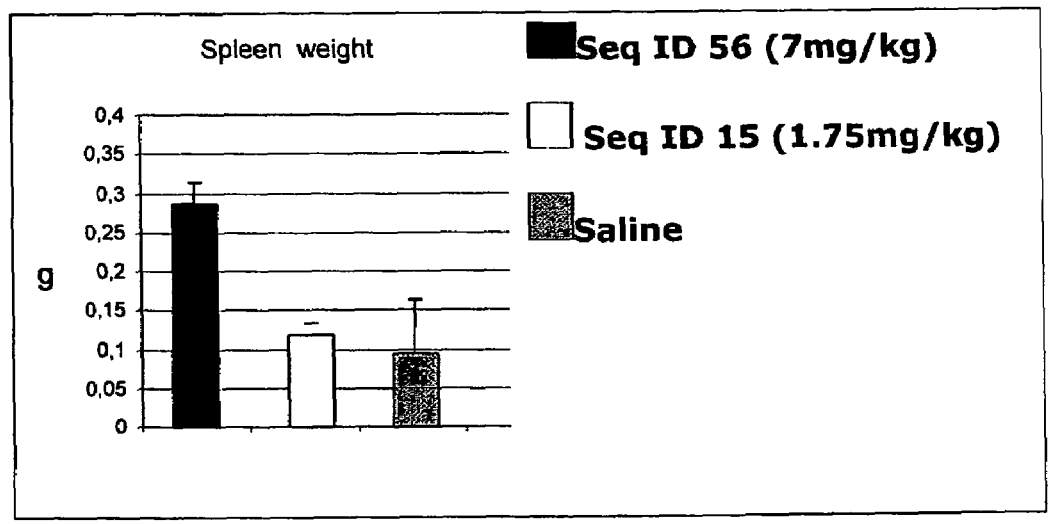
FIG. 10B shows no increase in spleen size when administering 1.75 mg/kg SEQ ID NO: 15 i.p. for 14 days in a melanoma 518A2 scid mice xenograft compared to the saline control. SEQ ID NO: 56 (reference) at 7 mg/kg presented an increase in spleen size. This indicates that SEQ ID NO: 15 has a lower toxicity level at active dose compared to SEQ ID NO: 56 (reference).
Figure 10C:
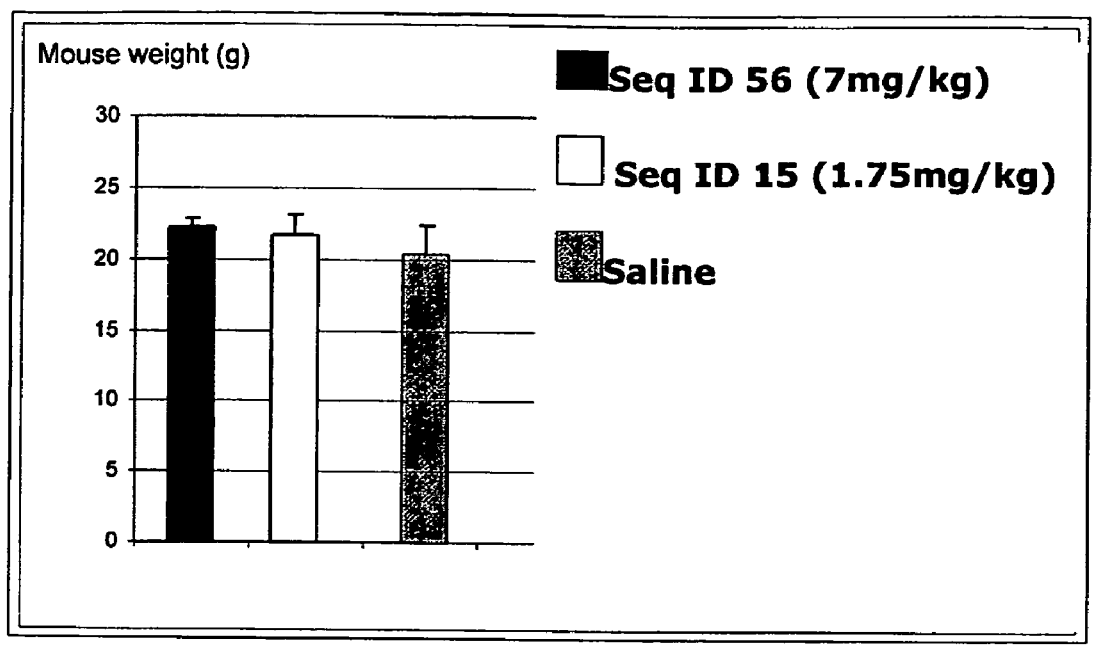
FIG. 10C shows that the treatment did not lead to a loss of mice body weight when administering 1.75 mg/kg SEQ ID NO: 15 i.p. for 14 days in a melanoma 518A2 scid mice xenograft compared to the saline control and SEQ ID NO: 56 (reference) at 7 mg/kg. This indicates that SEQ ID NO: 15 has a lower toxicity level at active dose compare to SEQ ID NO: 56 (reference).

The present inventors have also demonstrated an effective in vivo reduction of tumour volume using SEQ ID NO: 15 administered daily on days 7-15 or on days 8, 11, 13, 15, 18, 20 compared to the saline control in a prostate PC3 atymic nude mice xenograft model, cf. FIG. 7D. The compounds were administered i.p. at 10 mg/kg for 14 days. Tumour growth was monitored for additional 8 days post treatment.

This being said, the oligomeric compounds of the invention have a suitable in vivo profile with respect to distribution and down-regulation of Bcl-2 and thereby therapeutic relevance in connection with various Bcl-2 related conditions, in particular cancer.

Preparation of Oligomeric Compounds

The oligomeric compounds of the inventions can be prepared as described in Examples 1 and 2 and in WO 99/14226, WO 00/56746, WO 00/56748, WO 00/66604, WO 00/125248, WO 02/28875, WO 2002/094250, PCT/DK02/00488 and Herdewijn, P., Oligonucleotide Synthesis, Methods and Applications, pp 127-145, Humana Press, Totowa, N.J., 2005. Thus, the oligomeric compounds of the invention may be produced using the polymerisation techniques of nucleic acid chemistry well-known to a person of ordinary skill in the art of organic chemistry. Generally, standard oligomerisation cycles of the phosphoramidite approach (S. L. Beaucage and R. P. Iyer, *Tetrahedron*, 1993, 49, 6123; S. L. Beaucage and R. P. Iyer, *Tetrahedron*, 1992, 48, 2223) are used, but e.g. H-phosphonate chemistry, phosphotriester chemistry can also be used.

For some monomers of the invention longer coupling time, and/or repeated couplings with fresh reagents, and/or use of more concentrated coupling reagents were used.

The phosphoramidites employed coupled with satisfactory >95% step-wise coupling yields. Thiolation of the phosphate is performed by exchanging the normal, e.g. iodine/pyridine/$H_2O$, oxidation used for synthesis of phosphorodiester oligomers with an oxidation using the ADTT reagent (xanthane hydride (0.01 M in acetonitrile:pyridine 9:1; v/v)) other thiolation reagents are also comprised, such as Beaucage. The phosphorothioate LNA oligomers were efficiently synthesized with stepwise coupling yields >=98%.

The β-D-amino-LNA, β-D-thio-LNA oligonucleotides, α-L-LNA and β-D-methylamino-LNA oligonucleotides were also efficiently synthesized with step-wise coupling yields ≧98% using the phosphoramidite procedures.

Purification of LNA oligomeric compounds was done using disposable reversed phase purification cartridges and/or reversed phase HPLC and/or precipitation from ethanol or butanol. Capillary gel electrophoresis, reversed phase HPLC, MALDI-MS, and ESI-MS were used to verify the purity of the synthesized oligonucleotides. Furthermore, solid support materials having immobilized thereto an optionally nucleobase protected and optionally 5'-OH protected LNA are especially interesting as material for the synthesis of LNA containing oligomeric compounds where an LNA nucleotide is included in at the 3' end. In this instance, the solid support material is preferable CPG, e.g. a readily (commercially) available CPG material or polystyrene onto which a 3'-functionalised, optionally nucleobase protected and optionally 5'-OH protected LNA is linked using the conditions stated by the supplier for that particular material.

Salts

The oligomeric compound of the invention can be employed in a variety of pharmaceutically acceptable salts. As used herein, the term refers to salts that retain the desired biological activity of the herein identified compounds and exhibit minimal undesired toxicological effects. Non-limiting examples of such salts can be formed with organic amino acid and base addition salts formed with metal cations such as zinc, calcium, bismuth, barium, magnesium, aluminum, copper, cobalt, nickel, cadmium, sodium, potassium, and the like, or with a cation formed from ammonia, N,N-dibenzylethylene-diamine, D-glucosamine, tetraethylammonium, or ethylenediamine; or (c) combinations of (a) and (b); e.g., a zinc tannate salt or the like.

Such salts are formed, for example, from the compounds according to the invention which possess an acidic group, for example a carboxyl group, a phosphodiester group or a phosphorothioate group, and are, for example, salts with suitable bases. These salts include, for example, nontoxic metal salts which are derived from metals of groups Ia, Ib, IIa and IIb of the Periodic System of the elements, in particular suitable alkali metal salts, for example lithium, sodium or potassium salts, or alkaline earth metal salts, for example magnesium or calcium salts. They furthermore include zinc and ammonium salts and also salts which are formed with suitable organic amines, such as unsubstituted or hydroxyl-substituted mono-, di- or tri-alkylamines, in particular mono-, di- or tri-alkylamines, or with quaternary ammonium compounds, for example with N-methyl-N-ethylamine, diethylamine, triethyl-amine, mono-, bis- or tris-(2-hydroxy-lower alkyl) amines, such as mono-, bis- or tris-(2-hydroxyethyl)amine, 2-hydroxy-tert-butylamine or tris(hydroxymethyl)methylamine, N,N-di-lower alkyl-N-(hydroxy-lower alkyl)amines, such as N,N-dimethyl-N-(2-hydroxyethyl)amine or tri-(2-hydroxyethyl)amine, or N-methyl-D-glucamine, or quaternary ammonium compounds such as tetrabutylammonium salts. Lithium salts, sodium salts, magnesium salts, zinc salts or potassium salts are preferred, with sodium salts being particularly preferred.

Compounds according to the invention which possess a basic group, for example an amino group or imino group, can form acid addition salts, for example with inorganic acids, for example with a hydrohalic acid, such as hydrochloric acid, sulfuric acid or phosphoric acid, or with organic carboxylic acids, sulfonic acids, sulfo acids or phospho acids or N-substituted sulfamic acid, for example acetic add, proplonic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotonic acid or isonicotonic acid, and, in addition, with amino acids, for example with a-amino acids, and also with methanesulfonic acid, ethanesulfonic acid, 2-hydroxymethane-sulfonic acid, ethane-1,2-disulfonic acid, benzenedisulfonic acid, 4-methylbenzenesulfonic acid, naphthalene sulfonic acid, 2- or 3-phosphoglycerate, glucose phosphate or N-cyclo-hexylsulfamic acid (with formation of the cyclamates) or with other acidic organic compounds, such as ascorbic acid.

Compounds according to the invention which possess both acidic and basic groups can also form internal salts. Pharmaceutically unsuitable salts, for example picrates or perchlorates, can be used for isolation and purification.

It is only the pharmaceutically tolerated salts, which are non-toxic when used correctly, which are employed for therapeutic purposes and which are therefore preferred.

Conjugates

A further aspect of the invention relates to a conjugate comprising the compound as defined herein at least one non-nucleotide or non-polynucleotide moiety covalently attached to said compound.

In the present context, the term conjugate is intended to indicate a heterogenous molecule formed by the covalent attachment of an oligomeric compound as described herein (i.e. a compound comprising a sequence of nucleosides or nucleoside analogues) to one or more non-nucleotide or non-polynucleotide moieties.

Thus, the oligomeric compounds may, e.g., be conjugated or form chimera with non-nucleotide or non-polynucleotide moieties including Peptide Nucleic Acids (PNA), proteins (e.g. antibodies for a target protein), macromolecules, low molecular weight drug substances, fatty acid chains, sugar residues, glycoproteins, polymers (e.g. polyethylene glycol), micelle-forming groups, antibodies, carbohydrates, receptor-binding groups, steroids such as cholesterol, polypeptides, intercalating agents such as an acridine derivative, a long-chain alcohol, a dendrimer, a phospholipid and other lipophilic groups or combinations thereof, etc., just as the oligomeric compounds may be arranged in dimeric or dendritic structures. The compounds or conjugates of the invention may also be conjugated or further conjugated to active drug substances, for example, aspirin, ibuprofen, a sulfa drug, an antidiabetic, an antibacterial agent, a chemotherapeutic compound or an antibiotic.

Conjugating in this way confers advantageous properties with regard to the pharmacokinetic characteristics on the oligomeric compounds according to the invention. In particular, conjugating in this way achieves increased cellular uptake.

In one embodiment, the oligomeric compound of the invention is linked to ligands so as to form a conjugate, said ligands intended to increase the cellular uptake of the conjugate relative to the antisense oligonucleotides. This conjugation can take place at the terminal positions 5'/3'-OH but the ligands may also take place at the sugars and/or the bases. Examples of conjugates/lingands are cholesterol moieties Soutschek et al., Nature, 432, 173-178 (2004), duplex intercalators such as acridine, poly-L-lysine, "end-capping" with one or more nuclease-resistant linkage groups such as phosphoromonothioate, transferrin complexes (Wagner et al., Proc. Natl. Acad. Sci. USA 87, 3410-3414 (1990)), folate derivatives (Low et al., U.S. Pat. No. 5,108,921. Also see, Leamon et al., Proc. Natl. Acad. Sci. 88, 5572 (1991) and the like.

Prodrugs

In some embodiments of the invention, the oligomeric compound may be in the form of a pro-drug. Oligonucleotides are by virtue negatively charged ions. Due to the lipophilic nature of cell membranes, the cellular uptake of oligonucleotides is reduced compared to neutral or lipophilic equivalents. This polarity "hindrance" can be avoided by using the pro-drug approach (see e.g. Crooke, R. M. (1998) in Crooke, S. T., Antisense Research and Application. Springer-Verlag, Berlin, Germany, vol. 131, pp. 103-140). In this approach, the oligomeric compounds are prepared in a protected manner so that the oligomeric compounds are neutral when it is administered. These protection groups are designed in such a way that they can be removed then the oligomeric compound Is taken up be the cells. Examples of such protection groups are S-acetylthioethyl (SATE) or S-pivaloylthioethyl (t-butyl-SATE). These protection groups are nuclease resistant and are selectively removed intracellulary.

Therapeutic Principle

A person skilled in the art will appreciate the fact that the LNA oligomeric compounds of the Invention can be used to combat Bcl-2 linked diseases by many different principles, which thus falls within the spirit of the present invention.

For instance, the LNA oligomeric compounds may be designed as antisense Inhibitors, which are single stranded nucleic acids that prevent the production of a disease causing protein, by intervention at the mRNA level. Also, they may be designed as immunomodulator oligonucleotides (IMOs), ribozymes or oligozymes which are antisense oligonucleotides which In addition to the target binding domain(s) comprise a catalytic activity that degrades the target mRNA (ribozymes) or comprise an external guide sequence (EGS) that recruit an endogenous enzyme (RNase P) which degrades the target mRNA (oligozymes).

Equally well, the LNA oligomeric compounds may be designed as siRNAs which are small double stranded RNA molecules that are used by cells to silence specific endogenous or exogenous genes by an as yet poorly understood "antisense-like" mechanism.

The oligomeric compounds may also be designed as Aptamers (and a variation thereof, termed splegelmers) which are nucleic acids that through intra-molecular hydrogen bonding adopt three-dimensional structures that enable them to bind to and block their biological targets with high affinity and specificity. Also, LNA oligomeric compounds may be designed as Decoys, which are small double-stranded nucleic acids that prevent cellular transcription factors from transactivating their target genes by selectively blocking their DNA binding site.

Furthermore, LNA oligomeric compounds may be designed as Chimeraplasts, which are small single stranded nucleic acids that are able to specifically pair with and alter a target gene sequence. LNA containing oligomeric compounds exploiting this principle therefore may be particularly useful for treating Bcl-2 linked diseases that are caused by a mutation in the Bcl-2 gene.

Finally, LNA oligomeric compounds may be designed as TFOs (triplex forming oligonucleotides), which are nucleic acids that bind to double stranded DNA and prevent the production of a disease causing protein, by intervention at the RNA transcription level.

Referring to the above principles by which an LNA oligomeric compound can elicit its therapeutic action, the target of the present invention is the Bcl-2 mRNA.

The LNA oligomeric compound hybridizes to a portion of the human Bcl-2 mRNA that comprises the translation-initiation site, i.e. the region ranging from base position No. 1459 (5') to No. 1476 (3') of the human Bcl-2 mRNA encoding human Bcl-2 protein.

The skilled person will appreciate that the preferred LNA oligomeric compounds are those that hybridize to a portion of the Bcl-2 mRNA whose sequence does not commonly occur in transcripts from unrelated genes so as to maintain treatment specificity.

The oligomeric compounds of the invention are designed to be sufficiently complementary to the target to provide the desired clinical response e.g. the oligomeric compound must bind with sufficient strength and specificity to its target to give the desired effect. In one embodiment, said LNA oligomeric compound is designed so as to also modulate other specific nucleic acids which do not encode human Bcl-2 protein.

It is preferred that the oligomeric compounds according to the invention are designed so that intra- and intermolecular oligonucleotide hybridisation is avoided.

Antisense Drugs

In one embodiment of the invention, the LNA oligomeric compounds are presented as suitable antisense drugs. The design of a potent and safe antisense drug requires the fine-tuning of diverse parameters such as potency/efficacy, affinity/specificity, stability in biological fluids, cellular uptake, mode of action, pharmacokinetic properties and toxicity.

Affinity & Specificity: LNA with an oxymethylene 2'-O, 4'-C linkage (β-D-oxy-LNA), exhibits unprecedented binding properties towards DNA and RNA target sequences. Likewise LNA derivatives, such as amino-, thio- and α-L-oxy-LNA display unprecedented affinities towards complementary RNA and DNA, and in the case of thio-LNA, the affinity towards RNA Is even higher than with the β-D-oxy-LNA.

In addition to these remarkable hybridization properties, LNA nucleotides can be mixed and act cooperatively with DNA and RNA nucleotides, and with other nucleic acid analogues, such as 2'-O-alkyl modified RNA monomers. As such, the oligonucleotides of the present invention can be composed entirely of β-D-oxy-LNA nucleotides or it may be composed of β-D-oxy-LNA in any combination with DNA, RNA nucleotides or contemporary nucleic acid analogues which include LNA derivatives such as for instance amino-LNA, thio-LNA and α-L-oxy-LNA. The unprecedented binding affinity of LNA towards DNA or RNA target sequences and its ability to mix freely with DNA, RNA and a range of contemporary nucleic acid analogues has a range of important consequences according to the invention for the development of effective and safe antisense compounds. Moreover, oligonucleotides containing LNA present an excellent aqueous solubility.

Firstly, in one embodiment of the invention, it enables a considerable shortening of the usual length of an antisense oligonucleotide (from 20-25 mers to, e.g., 12-16 mers) without compromising the affinity required for pharmacological activity. As the intrinsic specificity of an oligonucleotide is inversely correlated to its length, such a shortening will significantly increase the specificity of the antisense compound towards its RNA target. One embodiment of the invention is to, due to the sequence of the human genome being available and the annotation of its genes rapidly progressing, identify the shortest possible, unique sequences in the target mRNA.

In another embodiment, the use of LNA to reduce the size of the antisense oligonucleotides significantly shortens the process and cost of manufacture, thus, providing the basis for antisense therapy to become a commercially competitive treatment offer for a variety of diseases.

In another embodiment, the unprecedented affinity of LNA can be used to substantially enhance the ability of the oligomeric compound to hybridize to its target mRNA in-vivo, thus, significantly reducing the time and effort required for identifying an active compound as compared to the situation with other chemistries.

In another embodiment, the unprecedented affinity of LNA is used to enhance the potency of antisense oligonucleotides, thus enabling the development of compounds with more favorable therapeutic windows than those currently in clinical trials.

When designed as an antisense inhibitor, the oligonucleotides of the invention bind specifically and selectively to the target nucleic acid and modulate the expression of its cognate protein. Preferably, such modulation produces an inhibition of expression of at least 10% or 20% compared to the normal expression level, more preferably at least a 30%, 40%, 50%, 60%, 70%, 80%, or 90% inhibition compared to the normal expression level.

Stability in Biological Fluids: One embodiment of the invention includes the incorporation of LNA nucleotides into a standard DNA or RNA oligonucleotide to increase the stability of the resulting oligomeric compound In biological fluids e.g. through the increase of resistance towards nucleases (endonucleases and exonudeases). The extent of stability will depend on the number of LNA nucleotides used, their position in the oligonucleotide and the type of LNA nucleotides used. Compared to DNA and phosphorothioates, the following order of ability to stabilize an oligonucleotide against nucleolytic degradation can be established: DNA<<phosphorothioates~oxy-LNA<α-L-LNA<amino-LNA<thio-LNA.

Given the fact that LNA is compatible with standard DNA synthesis and mixes freely with many contemporary nucleic acid analogues nuclease resistance of LNA- oligomeric compounds can be further enhanced according to the Invention by either incorporating other analogues that display increased nuclease stability or by exploiting nuclease-resistant internucleoside linkages e.g. phosphoromonothioate, phosphorodithioate, and methylphosphonate linkages, etc.

Mode of Action: Antisense compounds according to the invention may elicit their therapeutic action via a variety of mechanisms and may be able to combine several of these in the same compound. In one scenario, binding of the oligonucleotide to its target (pre-mRNA or mRNA) acts to prevent binding of other factors (proteins, other nucleic acids, etc.) needed for the proper function of the target i.e. operates by steric hindrance. For instance, the antisense oligonucleotide may bind to sequence motifs in either the pre-mRNA or mRNA that are important for recognition and binding of transacting factors involved in splicing, poly-adenylation, cellular transport, post-transcriptional modifications of nucleosides in the RNA, capping of the 5'-end, translation, etc. In the case of pre-mRNA splicing, the outcome of the interaction between the oligonucleotide and its target may be either suppression of expression of an undesired protein, generation of alternative spliced mRNA encoding a desired protein or both.

In another embodiment, binding of the oligonucleotide to its target disables the translation process by creating a physical block to the ribosomal machinery, i.e. tranlational arrest.

In yet another embodiment, binding of the oligonucleotide to its target interferes with the RNAs ability to adopt secondary and higher order structures that are important for its proper function, i.e. structural interference. For instance, the oligonucleotide may interfere with the formation of stem-loop structures that play crucial roles In different functions, such as providing additional stability to the RNA or adopting essential recognition motifs for different proteins.

In still another embodiment, binding of the oligonucleotide inactivates the target toward further cellular metabolic processes by recruiting cellular enzymes that degrade the mRNA. For instance, the oligonucleotide may comprise a segment of nucleosides that have the ability to recruit ribonuclease H (RNaseH) that degrades the RNA part of a DNA/RNA duplex. Likewise, the oligonucleotide may comprise a segment which recruits double stranded RNAses, such as for instance RNAseIII or it may comprise an external guide sequence (EGS) that recruits an endogenous enzyme (RNase P) which degrades the target mRNA. Also, the oligonucleotide may comprise a sequence motif which exhibits RNAse catalytic activity or moieties may be attached to the oligonucleotides which when brought Into proximity with the target by the hybridization event disable the target from further metabolic activities.

This being said, it is defined that the gap size of the gapmers, i.e. the subsegment, has a length of from 4 to 14 nucleobases, but it is believed that a length of in the range from 8 to 13 nucleobases, such as from 10 to 12 nucleobases, in particular 11 nucleobases, leads to particularly useful gapmers, cf. Table 1.

Pharmacokinetic Properties

The clinical effectiveness of antisense oligonucleotides depends on their pharmacokinetics e.g. absorption, distribution, cellular uptake, metabolism and excretion. In turn, these parameters are guided significantly by the underlying chemistry and the size and three-dimensional structure of the oligonucleotide.

As mentioned earlier, LNA according to the invention is not a single, but several related chemistries, which although molecularly different all exhibit stunning affinity towards complementary DNA and RNA. Thus, the LNA family of chemistries is uniquely suited of development oligos according to the Invention with tailored pharmacokinetic properties exploiting either the high affinity of LNA to modulate the size of the active compounds or exploiting different LNA chemistries to modulate the exact molecular composition of the active compounds. In the latter case, the use of for instance amino-LNA rather than oxy-LNA will change the overall charge of the oligomeric compound and affect uptake and distribution behavior. Likewise the use of thio-LNA instead of oxy-LNA will increase the lipophilicity of the oligonucleotide, and, thus, influence its ability to pass through lipophilic barriers such as for instance the cell membrane.

Modulating the pharmacokinetic properties of an LNA oligonucleotide according to the invention may further be achieved through attachment of a variety of different moieties. For instance, the ability of oligonucleotides to pass the cell membrane may be enhanced by attaching for instance lipid moieties such as a cholesterol moiety, a thioether, an aliphatic chain, a phospholipid or a polyamine to the oligonucleotide. Likewise, uptake of LNA oligonucleotides into cells may be enhanced by conjugating moieties to the oligonucleotide that interacts with molecules in the membrane, which mediates transport into the cytoplasm.

Pharmacodynamic Properties

The pharmacodynamic properties can according to the invention be enhanced with groups that improve oligomer uptake, enhance biostability such as enhance oligomer resistance to degradation, and/or Increase the specificity and affinity of oligonucleotides hybridisation characteristics with target sequence e.g. a mRNA sequence.

Toxicology

There are basically two types of toxicity associated with antisense oligomers: sequence-dependant toxicity, involving the target binding domain, and sequence-independent, class-related toxicity. With the exception of the issues related to immunostimulation by native CpG sequence motifs, the toxicities that have been the most prominent in the development of antisense oligonucleotides are independent of the sequence, e.g. related to the chemistry of the oligonucleotide and dose, mode, frequency and duration of administration. The phosphorothioates class of oligonucleotides have been particularly well characterized and found to elicit a number of adverse effects such as complement activation, prolonged PTT (partial thromboplastin time), thrombocytopenia, hepatotoxicity (elevation of liver enzymes), splenomegaly and hyperplasia of reticuloendothelial cells.

As mentioned earlier, the LNA family of chemistries provides unprecedented affinity, very high bio-stablity and the ability to modulate the exact molecular composition of the oligonucleotide. In one embodiment of the invention, LNA containing compounds enables the development of oligonucleotides which combine high potency with little- if any- phosphorothioate linkages and which are therefore likely to display better efficacy and safety than contemporary antisense compounds.

Pharmaceutical Composition

Following the above, it should be understood that the invention also relates to a pharmaceutical composition comprising an oligomeric compound or a conjugate as defined herein, and a pharmaceutically acceptable carrier.

Directions for the preparation of pharmaceutical compositions can be found In "Remington: The Science and Practice of Pharmacy" by Alfonso R. Gennaro, and in the following.

Pharmaceutically acceptable carriers, such as binding agents and adjuvants, are part of the pharmaceutical composition. Capsules, tablets and pills etc. may contain for example the following compounds: microcrystalline cellulose, gum or gelatin as binders; starch or lactose as excipients; stearates as lubricants; various sweetening or flavouring agents. For capsules, the dosage unit may contain a liquid carrier like fatty oils. Likewise coatings of sugar or enteric agents may be part of the dosage unit. The pharmaceutical composition may also be emulsions of the active pharmaceutical ingredients (including the oligomeric compound) and a lipid forming a micellular emulsion.

An oligomeric compound of the invention may be mixed with any material that do not impair the desired action, or with material that supplement the desired action. These could include other drugs including other nucleoside compounds.

For intravenous, subcutaneous, or topical administration, the formulation may include a sterile diluent, buffers, regulators of tonicity and antibacterials. The active compound may be prepared with carriers that protect against degradation or immediate elimination from the body, including implants or microcapsules with controlled release properties. For intravenous administration, the preferred carriers are physiological saline or phosphate buffered saline.

Preferably, an oligomeric compound is included in a unit formulation such as in a pharmaceutically acceptable carrier or diluent in an amount sufficient to deliver to a patient a therapeutically effective amount without causing serious side effects in the treated patient.

In preferred embodiments of the pharmaceutical compositions, the oligomeric compound is formulated in an aqueous carrier, in particular an aqueous carrier comprising a buffer for keeping the pH in the range of 4.0-8.5, and having an ionic strength of 20-2000 mM.

The term "aqueous carrier" means that the pharmaceutical composition in question is In liquid form, and that the liquid carrier predominantly is composed of water, i.e. that at least 80% (w/w), or at least 90% (w/w), or even at least 95% (w/w), of the carrier consists of water. Other liquid ingredients may also be used, e.g. ethanol, DMSO, ethylene glycol, etc.

The aqueous carrier preferably comprises a buffer for keeping the pH in the range of 4.0-8.5. Preferably, the buffer will keep the pH in the range of 5.0-8.0, such as in the range of 6.0-7.5.

The ionic strength/tonicity of the pharmaceutical composition is also of importance. Thus, typically, the liquid pharmaceutical composition has an ionic strength of in the range of 20-2000 mM, such as in the range of 50-1500 mM, or in the range of 100-1000 mM.

In one embodiment, the liquid pharmaceutical composition comprises an oligomeric compound as defined herein in an aqueous carrier; and said aqueous carrier comprising a buffer for keeping the pH in the range of 4.0-8.5, and having an ionic strength of 20-2000 mM.

In another embodiment, the liquid pharmaceutical composition comprising a conjugate in an aqueous carrier, said conjugate consisting of an oligomeric compound as defined herein and at least one non-nucleotide/non-polynucleotide moiety covalently attached to said oligomeric compound; and said aqueous carrier comprising a buffer for keeping the pH In the range of 4.0-8.5, and having an ionic strength of 20-2000 mM.

Within the two embodiments, the target binding domain of the oligomeric compound is preferably one selected from the group consisting of SEQ ID NOS: 1, 2, 3, 4, 5, 6, 7, 8 (and 35), 12, 13, 14, 41, 42, 43, 44, 45, 46, 47, 48, 49, 50, 51, and 52, in particular the target binding domain is SEQ ID NO: 8 (and 35), or the target binding domain of the oligomeric compound is preferably one selected from the group consisting of SEQ ID NOS: 15 (and 29), 17, 18, 19, 21, 22, 23, 24, 25, 26, 27, 28, 53, 54 and 55, in particular the target binding domain is SEQ ID NO: 15 (and 29).

As above, it is particularly preferred if the compound is selected from the group consisting of SEQ ID NOS: 1, 2, 3, 4, 5, 6, 7, 8 (and 35), 12, 13, 14, 41, 42, 43, 44, 45, 46, 47, 48, 49, 50, 51 and 52, in particular SEQ ID NO: 8 (and 35), or if the compound is selected from the group consisting of SEQ ID NOS: 15 (and 29), 17, 18, 19, 21, 22, 23, 24, 25, 26, 27, 28, 53, 54 and 55, in particular SEQ ID NO: 15 (and 29).

In a further embodiment, the pharmaceutical composition also comprises a further agent selected from the groups consisting of chemotherapeutic compounds, anti-inflammatory compounds, antiviral compounds, cytostatic compounds, anti-anglogenetic compounds, anti-proliferative compounds, pro-apoptotic compounds, signal transduction modulators, and kinase inhibitors.

In a particularly interesting variant, the further agent is at least one chemotherapeutic compound. Suitable examples of such chemotherapeutic compound are those selected from the group consisting of adrenocorticosteroids, such as prednisone, dexamethasone or decadron; altretamine (hexalen, hexamethylmelamine (HMM)); amifostine (ethyol); aminoglutethimide (cytadren); amsacrine (M-AMSA); anastrozole (arimidex); androgens, such as testosterone; asparaginase (elspar); bacillus calmette-gurin; bicalutamide (casodex); bleomycin (blenoxane); busulfan (myleran); carboplatin (paraplatin); carmustine (BCNU, BiCNU); chlorambucil (leukeran); chlorodeoxyadenosine (2-CDA, cladribine, leustatin); cisplatin (platinol); cytosine arabinoside (cytarabine); dacarbazine (DTIC); dactinomycin (actinomycin-D, cosmegen); daunorubicin (cerubidine); docetaxel (taxotere); doxorubicin (adriomycin); epirubicin; estramustine (emcyt); estrogens, such as diethylstilbestrol (DES); etopside (VP-16, VePesid, etopophos); fludarabine (fludara); flutamide (eulexin); 5-FUDR (floxuridine); 5-fluorouracil (5-FU); gemdtabine (gemzar); goserelin (zodalex); herceptin (trastuzumab); hydroxyurea (hydrea); idarubicin (idamycin); ifosfamide; IL-2 (proleukin, aldesleukin); interferon alpha (intron A, roferon A); irinotecan (camptosar); leuprolide (lupron); levamisole (ergamisole); lomustine (CCNU); mechlorathamine (mustargen, nitrogen mustard); melphalan (alkeran); mercaptopurine (purinethol, 6-MP); methotrexate (mexate); mitomycin-C (mutamucin); mitoxantrone (novantrone); octreotide (sandostatin); pentostatin (2-deoxycoformycin, nipent); plicamycin (mithramycin, mithracin); proroca rbazine (matulane); streptozocin; tamoxifin (nolvadex); taxol (paditaxel); teniposide (vumon, VM-26); thiotepa; topotecan (hycamtin); tretinoin (vesanold, all-trans retinoic acid); vinblastine (valban); vincristine (oncovin) and vinorelbine (navelbine). In one embodiment, the chemotherapeutic compound is selected from fludarabine and taxanes such as Taxol, Paclitaxel and Docetaxel, in particular fludarabine.

In one variant, the present invention provides pharmaceutical compositions containing (a) one or more oligomeric compounds and (b) one or more other chemotherapeutic compounds which function by a non-antisense mechanism. When used with the compounds of the invention, such chemotherapeutic compounds may be used individually (e.g. mithramycin and oligonucleotide), sequentially (e.g. mithramycin and oligonucleotide for a period of time followed by another agent and oligonucleotide), or in combination with one or more other such chemotherapeutic compounds or in combination with radiotherapy. All chemotherapeutic compounds known to a person skilled in the art including those explicitly mentioned above are here incorporated as combination treatments with compound according to the invention.

In one variant, the present invention provides pharmaceutical compositions containing (a) one or more oligomeric compounds and (b) one or more antibody compounds. One and more chemotherapeutic compounds may also be added to this combination.

In one preferred embodiment, the pharmaceutical composition is administered in combination with a compound selected from fludarabine and taxane compounds.

The term "taxane compound" is intended to encompass paclitaxel (Taxol®), paclitaxel derivatives, docetaxel, taxotere, modified taxanes, and taxoid analogues. Paclitaxel (Taxol®) is a diterpene isolated from the bark of the Western (Pacific) yew, *Taxus brevifolia* and is representative of a class of therapeutic agents having a taxane ring system. Pacilitaxel and its analogs have been produced by partial synthesis from 10-deacetylbaccatin III, a precursor obtained from yew needles and twigs, and by total synthesis. See Holton, et al., J. Am. Chem. Soc. 116:1597-1601 (1994) and Nicoiaou, et al., Nature 367:630 (1994). Paclitaxel has demonstrated efficacy in several human tumours in clinical trials. See McGuire, et al., Ann. Int. Med. 111:237-279 (1989); Holmes, et al., J. Natl. Cancer Inst. 83:1797-1805 (1991); Kohn et al., J. Natl. Cancer Inst. 86:18-24 (1994); and Kohn, et al., American Society for Clinical Oncology 12 (1993). The modified taxane or taxoid analogs are those compounds having a taxane ring bearing modified side chains. A number of these analogs have improved properties, such as greater water solubility and stability than that of naturally occurring paclitaxel. These analogs are known to those skilled in the art and are disclosed, for example, In U.S. Pat. Nos. 5,278,324; 5,272,171; 5,254,580; 5,250,683; 5,248,796; and 5,227,400, the disclosures of which are incorporated herein by reference. Paclitaxel and taxotere can be prepared by the methods in WO 93/18210, EP 0 253 739, EP 0 253 739, and WO 92/09589, the disclosures of which are incorporated herein by reference. In particular embodiments, the taxane compound is paclitaxel or taxotere.

The weight ratio between the chemotherapeutic compound(s) (e.g. fludarabine and/or taxane compound(s)) and the oligomeric compound in said composition is typically in the range of 50:1 to 1:25, such as in the range of 25:1 to 1:25, or in the range of 10:1 to 1:25, or in the range of 1:1 to 1:25, or in the range of 50:1 to 1:10, or in the range of 1:1 to 1:50, or in the range of 25:1 to 1:10.

In one embodiment, the pharmaceutical composition comprises at least one chemotherapeutic compound (e.g. fludarabine and/or taxane compound(s)) and an oligomeric compound as defined herein in a pharmaceutically acceptable carrier; wherein the weight ratio between the chemotherapeutic compound(s) and the oligomeric compound in said composition is in the range of 50:1 to 1:25.

In another embodiment, the pharmaceutical composition comprises at least one chemotherapeutic compound (e.g. fludarabine and/or taxane compound(s)) and a conjugate in a pharmaceutically acceptable carrier, said conjugate consisting of an oligomeric compound as defined herein and at least one non-nucleotide/non-polynucleotide moiety covalently attached to said oligomeric compound; and wherein the weight ratio between the chemotherapeutic compound(s) and the oligomeric compound part of the conjugate in said composition is in the range of 50:1 to 1:25. In a variant within this embodiment, the at least one non-nucleotide/non-polynucleotide moiety comprises a chemotherapeutic compound (e.g. fludarabine or a taxane compound).

Within the two embodiments, the target binding domain of the oligomeric compound is preferably one selected from the group consisting of SEQ ID NOS: 1, 2, 3, 4, 5, 6, 7, 8 (and 35), 12, 13, 14, 41, 42, 43, 44, 45, 46, 47, 48, 49, 50, 51, and 52, in particular the target binding domain is SEQ ID NO: 8 (and 35), or the target binding domain of the oligomeric compound is preferably one selected from the group consisting of SEQ ID NOS: 15 (and 29), 17, 18, 19, 21, 22, 23, 24, 25, 26, 27, 28, 53, 54 and 55, in particular the target binding domain is SEQ ID NO: 15 (and 29).

As above, it is particularly preferred if the compound is selected from the group consisting of SEQ ID NOS: 1, 2, 3, 4, 5, 6, 7, 8 (and 35), 12, 13, 14, 41, 42, 43, 44, 45, 46, 47, 48, 49, 50, 51 and 52, in particular SEQ ID NO: 8 (and 35), Qr If the compound is selected from the group consisting of SEQ ID NOS: 15 (and 29), 17, 18, 19, 21, 22, 23, 24, 25, 26, 27, 28, 53, 54 and 55, in particular SEQ ID NO: 15 (and 29).

The oligomeric compounds of the invention may also be conjugated to active drug substances, for example, aspirin, ibuprofen, a sulfa drug, an antidiabetic, an antibacterial or an antibiotic.

Anti-inflammatory drugs, including but not limited to non-steroidal anti-inflammatory drugs and corticosterolds, antiviral drugs, and immuno-modulating drugs may also be combined in compositions of the invention. Two or more combined compounds may be used together or sequentially.

In a further embodiment, pharmaceutical compositions of the invention may contain one or more oligomeric compounds targeted to Bcl-2 and one or more additional antisense compounds targeted to a second nucleic acid target. Two or more combined compounds may be used together or sequentially.

Furthermore, the medicaments comprising the oligomeric compounds may be used in combination with radiotherapy, etc.

Preferred Pharmaceutical Compositions

In one embodiment, the pharmaceutical composition of the invention is a liquid pharmaceutical composition comprising an oligomeric compound of 10-30 nucleobases in length in an aqueous carrier, said oligomeric compound comprising a target binding domain that is specifically hybridizable to a region ranging from base position No. 1459 (5') to No. 1476 (3') of the human Bcl-2 mRNA, said target binding domain having the formula:

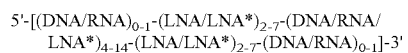

wherein "LNA" designates an LNA nucleotide and "LNA*" designates an LNA analogue nucleotide; and
said target binding domain comprising at least two LNA nucleotides or LNA analogue nucleotides linked by a phosphorothioate group (—O—P(O,S)—O—); and
said aqueous carrier comprising a buffer for keeping the pH in the range of 4.0-8.5, and having an ionic strength of 20-2000 mM.

In another embodiment, the pharmaceutical composition of the invention is a liquid pharmaceutical composition comprising a conjugate in an aqueous carrier, said conjugate consisting of an oligomeric compound of 10-30 nucleobases in length and at least one non-nucleotide/non-polynucleotide moiety covalently attached to said compound, said oligomeric compound comprising a target binding domain that is specifically hybridizable to a region ranging from base position No. 1459 (5') to No. 1476 (3') of the human Bcl-2 mRNA, said target binding domain having the formula:

wherein "LNA" designates an LNA nucleotide and "LNA*" designates an LNA analogue nucleotide; and
said target binding domain comprising at least two LNA nucleotides or LNA analogue nucleotides linked by a phosphorothioate group (—O—P(O,S)—O—); and
said aqueous carrier comprising a buffer for keeping the pH in the range of 4.0-8.5, and having an ionic strength of 20-2000 mM.

Such composition preferably further comprises at least one chemotherapeutic compound (e.g. fludarabine and/or taxane compound(s)). As mentioned above, the weight ratio between the chemotherapeutic compound(s) and the LNA oligonucleotide part of the conjugate in said composition is typically in the range of 50:1 to 1:25.

In a further embodiment, the pharmaceutical composition of the invention is a pharmaceutical composition comprising at least one chemotherapeutic compound (e.g. fludarabine and/or taxane compound(s)) and an oligomeric compound of 10-30 nucleobases in length in an aqueous carrier, said oligomeric compound comprising a target binding domain that is specifically hybridizable to a region ranging from base position No. 1459 (5') to No. 1476 (3') of the human Bcl-2 mRNA, said target binding domain having the formula:

wherein "LNA" designates an LNA nucleotide and "LNA*" designates an LNA analogue nucleotide; and
said target binding domain comprising at least two LNA nucleotides or LNA analogue nucleotides linked by a phosphorothioate group (—O—P(O,S)—O—); and
wherein the weight ratio between the chemotherapeutic compound(s) and the LNA oligonucleotide in said composition is in the range of 50:1 to 1:25.

In a still further embodiment, the pharmaceutical composition of the invention is a pharmaceutical composition comprising at least one chemotherapeutic compound (e.g. fludarabine and/or taxane compound(s)) and a conjugate in a pharmaceutically acceptable carrier, said conjugate consisting of an oligomeric compound of 10-30 nucleobases in length and at least one non-nucleotide/non-polynucleotide moiety covalently attached to said compound, said oligomeric compound comprising a target binding domain that is specifically hybridizable to a region ranging from base position No. 1459 (5') to No. 1476 (3') of the human Bcl-2 mRNA, said target binding domain having the formula:

wherein "LNA" designates an LNA nucleotide and "LNA*" designates an LNA analogue nucleotide; and
said target binding domain comprising at least two LNA nucleotides or LNA analogue nucleotides linked by a phosphorothioate group (—O—P(O,S)—O—); and
wherein the weight ratio between the chemotherapeutic compound(s) and the LNA oligonucleotide part of the conjugate in said composition is in the range of 50:1 to 1:25.

Indications

Bcl-2 is involved in a number of basic biological mechanisms including red blood cell proliferation, cellular proliferation, ion metabolism, glucose and energy metabolism, pH regulation and matrix metabolism. The methods of the invention are preferably employed for treatment, maintenance treatment or prophylaxis against diseases caused by cancer, particularly for treatment of cancer associated with expression of Bcl-2 such as breast, colon, prostate, pancreas, lung, liver, thyroid, kidney, brain, testes, stomach, intestine, bowel, spinal cord, sinuses, bladder, urinary tract, ovaries, head and neck, hematologic, skin, gastric, or bone cancer.

The invention described herein encompasses a method of preventing, maintenance treatment or treating cancer comprising a therapeutically effective amount of a Bcl-2 modulating oligomeric compound, to a human. The invention further encompasses the use of a short period of administration of a Bcl-2 modulating oligomeric compound. Normal, non-cancerous cells divide at a frequency characteristic for the particular cell type. When a cell has been transformed into a cancerous state, uncontrolled cell proliferation and reduced cell death results, and therefore, promiscuous cell division or cell growth is a hallmark of a cancerous cell type. Examples of types of cancer, include, but are not limited to lymphomas and leukemias (e.g. non-Hodgkin's lymphoma, Hodgkin's lymphoma, acute leukemia such as acute lymphocytic leukemia, acute myelocytic leukemia, chronic myeloid leukemia, chronic lymphocytic leukemia, multiple myeloma), colon carcinoma, rectal carcinoma, pancreatic cancer, breast cancer, ovarian cancer, prostate cancer, renal cell carcinoma, hepatoma, bile duct carcinoma, choriocarcinoma, cervical cancer, testicular cancer, lung carcinoma, bladder carcinoma, melanoma, head and neck cancer, brain cancer, cancers of unknown primary site, neoplasms, cancers of the peripheral nervous system, cancers of the central nervous system, different kind of tumours (e.g., fibrosarcoma, myxosarcoma, liposarcoma, chondrosarcoma, osteogenic sarcoma, chordoma, angisarcoma, endotheliosarcoma, lymphangiosarcoma, lymphangioendotheliosarcoma, synovioma, mesothelioma, Ewing's tumour, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, seminoma, embryonal carcinoma, Wilms' tumour, small cell lung carcinoma, epithelial carcinoma, glioma, astrocytoma, medulloblastoma, craniopharyngioma, ependymoma, pinealoma, hemangioblastoma, acoustic neuroma, oligodendroglioma, meningioma, neuroblastoma, and retinoblastoma), heavy chain disease, metastases, or any disease or disorder characterized by uncontrolled or abnormal cell growth.

The Non-Hodgkin's lymphomas of the invention comprise but are not limited to Precursor cell lymphoma such as lymphoblastic lymphoma (T cell and B cell); Peripheral B-cell neoplasms such as B-chronic lymphocytic leukaemia and small lymphocytic lymphoma, B-prolymphocytic leukaemia, Lymphoplasmacytic lymphoma, Mantel Cell lymphoma, Follicular lymphoma, Extranodal marginal zone B-cell lymphoma of MALT type, Nodal marginal zone B-cell lymphoma, Splenic marginal zone B-cell lymphoma, Hairy cell leukaemia, Diffuse large B-cell lymphoma, Burkitt lymphoma including Burkitt-like lymphoma, Plasmacytoma and plasma cell myeloma; Peripheral T and NK cell neoplasms such as T-prolymphocytic leukaemia, T-cell granular lymphocytic leukaemia, aggressive NK cell leukaemia, Mycosis fungoides and Sezary syndrome, Peripheral T-cell lymphoma, Angioimmunoblastic T-cell lymphoma, Extranodal NK/T cell lymphoma (nasal and nasal-type), Enteropathy-type T-cell lymphoma, Hepatosplenic γδ T-cell lymphoma, Subcutaneous panniculitis-like T-cell lymphoma, Anaplastic large cell lymphoma (T/null cell and primary systemic type), Anaplastic large cell lymphoma (T/null cell, primary cutaneous type) and Adult T-cell lymphoma and leukaemia (HTLV1+).

It is presently believed that the cancer types for which particularly good clinical results can be achieved are Acute Myelold Leukemia, Chronic Lymphocytic Leukemia and Non-Hodgkin's Lymphomas particularly Follicular lymphoma and Diffuse large B-cell lymphoma.

The term "carcinoma" is intended to indicate a malignant tumour of epithelial origin. Epithelial tissue covers or lines the body surfaces inside and outside the body. Examples of epithelial tissue are the skin and the mucosa and serosa that line the body cavities and internal organs, such as intestines, urinary bladder, uterus, etc. Epithelial tissue may also extend into deeper tissue layers to form glands, such as mucus-secreting glands.

The term "sarcoma" is intended to indicate a malignant tumour growing from connective tissue, such as cartilage, fat, muscles, tendons and bones.

The term "glioma", when used herein, is intended to cover a malignant tumour originating from glial cells.

Uses

The oligomeric compounds of the present invention can be utilized for as therapeutics, maintenance treatment and prophylaxis. In research, the antisense oligomeric compounds may be used to specifically inhibit the synthesis of Bcl-2 protein in cells and experimental animals thereby facilitating functional analysis of the target or an appraisal of its usefulness as a target for therapeutic intervention. For therapeutics, an animal or a human (in particular a human), suspected of having a disease or disorder, which can be treated by modulating the expression of Bcl-2 is treated by administering antisense compounds In accordance with this invention. Further provided are methods of treating an animal, in particular mouse and rat, and treating a human, suspected of having or being prone to a disease or condition, associated with expression of Bcl-2 by administering a therapeutically or prophylactically effective amount of one or more of the antisense compounds or compositions of the invention.

The invention further provides a method of modulating the expression of Bcl-2 in cells or tissue, the method comprising contacting said cells or tissue with an oligomeric compound or a conjugate as defined herein, in particular a pharmaceutical composition as defined herein, so that expression of Bcl-2 is modulated.

Still further, the invention provides a method of modulating expression of a gene involved in a cancer disease comprising contacting the gene or RNA from the gene with an oligomeric compound or a conjugate as defined herein, in particular a pharmaceutical composition as defined herein, whereby gene expression is modulated. The gene is preferably the human Bcl-2 gene.

A further aspect of the present invention relates to a method of inducing cell apoptosis comprising contacting the cell or RNA from the cell with an oligomeric compound or a conjugate as defined herein, in particular a pharmaceutical composition as defined herein, whereby cell apoptosis is induced. The induction of apoptosis may be in vitro or in vivo. The induction may be provoked in a cellular assay or within a tissue sample or within the living mammal.

A further aspect of the present invention relates to a method of preventing or reducing cellular proliferation comprising contacting the cell or RNA from the cell with an oligomeric compound or a conjugate as defined herein, in particular a pharmaceutical composition as defined herein, whereby cellular proliferation is prevented or reduced. The prevention or reduction of proliferation may be in vitro or in vivo. The prevention may be done on a cellular assay or within a tissue sample or within the living mammal.

Still further, the invention provides a method of treating a mammal suffering from or susceptible to a cancer disease, the method comprising administering to the mammal a therapeutically effective amount of an oligomeric compound or a conjugate as defined herein, in particular a pharmaceutical composition as defined herein.

In one embodiment, the treatment is combined with the administration of a further agent selected from the group consisting of chemotherapeutic compounds, anti-inflammatory compounds, antiviral compounds, cytostatic compounds, anti-angiogenetic compounds, anti-proliferative compounds, pro-apoptotic compounds, signal transduction modulators, antibody and kinase inhibitors. In a particular variant, the further agent is at least one chemotherapeutic agent, in particular one or more of the specific chemotherapeutic agents mentioned above.

The present invention also provides a method of treating a mammal suffering from or susceptible to a disease caused by angiogenesis, the method comprising administering to the mammal a therapeutically effective amount of an oligomeric compound or a conjugate as defined herein, in particular a pharmaceutical composition as defined herein.

Still further, the invention provides the oligomeric compounds as defined herein for use as a medicament. More particularly, the invention provides the use of an oligomeric compound as defined herein for the preparation of a medicament for the treatment of a cancer disease. The medicament is preferably in the form of a pharmaceutical composition as defined above.

Thus, one further aspect of the present invention relates to the use of an oligomeric compound as defined herein for the preparation of a pharmaceutical composition for the treatment a mammal, in particular a human, suffering from or susceptible to a cancer disease.

A still further aspect of the present invention relates to a method of treating a mammal, in particular a human, suffering from or susceptible to a cancer disease, the method comprising the step of administering to the mammal one or more therapeutically effective doses of a first pharmaceutical composition comprising an oligomeric compound as defined herein.

A still further aspect of the present invention relates to a method of treating a mammal, in particular a human, suffering from or susceptible to a cancer disease, the method comprising the step of administering to the mammal one or more therapeutically effective doses of a first pharmaceutical composition comprising a conjugate, said conjugate consisting of an oligomeric compound as defined herein and at least one non-nucleotide/non-polynucleotide moiety covalently attached to said oligomeric compound.

A variant of the latter two aspects, is the one wherein one or more chemotherapeutic compound(s) (e.g. fludarabine and/or taxane compound(s)) are administered In combination with the LNA oligonucleotide, in particular wherein the chemotherapeutic compound(s) is/are present In the first pharmaceutical composition comprising the LNA oligonucleotide.

Another variant of the latter two aspects, is the one wherein the one or more chemotherapeutic compound(s) (e.g. fludarabine and/or taxane compound(s)) is/are present in a second pharmaceutical composition not comprising the LNA oligonucleotide. In this instance, the first pharmaceutical composition and the second pharmaceutical composition may be administered concomitantly, or may be administered sequentially.

More generally, the medicament may further comprise a further agent selected from the group consisting of chemotherapeutic compounds, anti-inflammatory compounds, antiviral compounds, cytostatic compounds, anti-angiogenetic compounds, anti-proliferative compounds, pro-apoptotic compounds, signal transduction modulators, and kinase inhibitors. In a particular variant, the further agent is at least one chemotherapeutic compound, in particular one or more of the specific chemotherapeutic compounds mentioned above.

The cancer diseases referred to above are in particular a lung, breast, colon, prostate, pancreas, lung, liver, thyroid, kidney, brain, testes, stomach, Intestine, bowel, spinal cord, sinuses, bladder, urinary tract, ovaries, head and neck, hematologic, or skin cancer, as described in further detail above.

Furthermore, the present invention provides a complex comprising a compound hybridized to a ribonucleic acid encoding human Bcl-2 protein, said compound being an oligomeric compound or a conjugate as defined herein. Such complexes may be the result of treatment of a target, i.e. a ribonucleic acid encoding human Bcl-2 protein, with an oligomeric compound or conjugate as defined herein.

Administration

The pharmaceutical compositions of the present invention may be administered in a number of ways depending upon whether local or systemic treatment is desired and upon the area to be treated. Administration may be (a) oral (b) pulmonary, e.g., by Inhalation or insufflation of powders or aerosols, including by nebulizer; intratracheal, intranasal, (c) topical including epidermal, transdermal, ophthalmic and to mucous membranes includingvaginal and rectal delivery; or (d) parenteral including intravenous, intraarterial, subcutaneous, intraperitoneal or intramuscular injection or infusion; or intracranial, e.g., intrathecal or intraventricular, administration. In one embodiment, the oligomeric compound is administered IV, IP, orally, topically or as a bolus injection or administered directly in to the target organ.

Pharmaceutical compositions and formulations for topical administration may Include transdermal patches, ointments, lotions, creams, gels, drops, sprays, suppositories, liquids and powders. Conventional pharmaceutical carriers, aqueous, powder or oily bases, thickeners and the like may be necessary or desirable. Coated condoms, gloves and the like may also be useful. Preferred topical formulations include those in which the oligonucleotides of the invention are in admixture with a topical delivery agent such as lipids, liposomes, fatty acids, fatty acid esters, steroids, chelating agents and surfactants. Compositions and formulations for oral administration include but is not restricted to powders or granules, microparticulates, nanoparticulates, suspensions or solutions in water or non-aqueous media, capsules, gel capsules, sachets, tablets or minitablets. Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Delivery

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids. Delivery of drug to tumour tissue may be enhanced by carrier-mediated delivery including, but not limited to, cationic liposomes, cyclodextrins, porphyrin derivatives, branched chain dendrimers, polyethylenimine polymers, nanoparticles and microspheres (Dass CR. J Pharm Pharmacol 2002; 54(1):3-27).

The pharmaceutical formulations of the present invention, which may conveniently be presented in unit dosage form, may be prepared according to conventional techniques well-known in the pharmaceutical industry. Such techniques include the step of bringing the active ingredients into association with the pharmaceutical carrier(s) or excipient(s). In general the formulations are prepared by uniformly and intimately bringing the active ingredients into association with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels and suppositories. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Dosage

Dosing is dependent on severity and responsiveness of the disease state to be treated, and the course of treatment lasting from several days to several months, or until a cure is effected or a diminution of the disease state is achieved. Optimal dosing schedules will e.g. depend on the choice of combination treatment, disease and disease state and the results from the initial clinical trails.

Optimum dosages may vary depending on the relative potency of individual oligonucleotides. Generally it can be estimated based on EC50s found to be effective in in vitro and in vivo animal models. In general, dosage is from 0.01 μg to 1 g per kg of body weight, and may be given once or more daily, weekly, monthly or yearly, or even once every 2 to 10 years or by continuous infusion for hours up to several months. The repetition rates for dosing can be estimated based on measured residence times and concentrations of the drug in bodily fluids or tissues. Following successful treatment, it may be desirable to have the patient undergo maintenance therapy to prevent the recurrence of the disease state.

Without being bound to any particular theory, it is envisaged that the combined effect (and potentially synergistic effect) of a chemotherapeutic compound and an oligomeric compound according to the invention will render it possible to reduce the dosage of the chemotherapeutic compound or the oligomeric compound, or both.

A Kit

A still further aspect of the present invention relates to a kit comprising
(a) a first component containing one or more injectable solution doses of an oligomeric compound as defined herein, and
(b) a second component containing one or more injectable solutions of one or more chemotherapeutic compound (e.g. fludarabine and/or taxane compound(s)); and
wherein the weight ratio between the at least one taxane compound and the at least one LNA oligonucleotide in said composition is in the range of 50:1 to 1:25.

Preferably, the injectable solution doses of an oligomeric compound are pharmaceutical compositions as defined above.

EXAMPLES

Example 1

Monomer Synthesis

The LNA monomer building blocks and derivatives thereof were prepared following published procedures and references cited therein, see:
WO 03/095467 A1
D. S. Pedersen, C. Rosenbohm, T. Koch (2002) Preparation of LNA Phosphoramidites, Synthesis 6, 802-808.
M. D. Sørensen, L. Kværnø, T. Bryld, A. E. Håkansson, B. Verbeure, G. Gaubert, P. Herdewijn, J. Wengel (2002) α-L-ribo-configured Locked Nucleic Acid (α-l-LNA): Synthesis and Properties, J. Am. Chem. Soc., 124, 2164-2176.
S. K. Singh, R. Kumari J. Wengel (1998) Synthesis of Novel Bicyclo[2.2.1] Ribonucleosides: 2'-Amino- and 2'-Thio-LNA Monomeric Nucleosides, J. Org. Chem. 1998, 63, 6078-6079.
C. Rosenbohm, S. M. Christensen, M. D. Sørensen, D. S. Pedersen, L. E. Larsen, J. Wengel, T. Koch (2003) Synthesis of 2'-amino-LNA: a new strategy, Org. Biomol. Chem. 1, 655-663.
D. S. Pedersen, T. Koch (2003) Analogues of LNA (Locked Nucleic Acid). Synthesis of the 2'-Thio-LNA Thymine and 5-Methyl Cytosine Phosphoramidites, Synthesis, accepted.

Example 2

Oligonucleotide Synthesis

Small Scale Synthesis of Olibonucleotides:
Oligonucleotides were synthesized using the phosphoramidite approach on an Expedite 8900/MOSS synthesizer (Multiple Oligonucleotide Synthesis System) at 1 μmol or 15 μmol scale. For larger scale synthesis an Äkta Oligo Pilot was used. At the end of the synthesis (DMT-on), the oligonucleotides were cleaved from the solid support using aqueous ammonia for 1-2 h at room temperature, and further deprotected for 4 h at 65° C. The oligonucleotides were purified by reverse phase HPLC (RP-HPLC). After the removal of the DMT-group, the oligonucleotides were characterized by AE-HPLC, RP-HPLC, and CGE and the molecular mass was further confirmed by ESI-MS. See below for more details.

Preparation of the LNA-solid Support:

Preparation of the LNA Succinyl Hemiester

5'-O-Dmt-3'-hydroxy-LNA monomer (500 mg), succinic anhydride (1.2 eq.) and DMAP (1.2 eq.) were dissolved in DCM (35 mL). The reaction was stirred at room temperature overnight. After extractions with $NaH_2PO_4$ 0.1 M pH 5.5 (2×) and brine (1×), the organic layer was further dried with anhydrous $Na_2SO_4$ filtered and evaporated. The hemiester derivative was obtained in 95% yield and was used without any further purification.

Preparation of the LNA-support

The above prepared hemiester derivative (90 μmol) was dissolved in a minimum amount of DMF, DIEA and pyBOP (90 μmol) were added and mixed together for 1 min. This pre-activated mixture was combined with LCAA-CPG (500 Å, 80-120 mesh size, 300 mg) in a manual synthesizer and stirred. After 1.5 h at room temperature, the support was filtered off and washed with DMF, DCM and MeOH. After drying, the loading was determined to be 57 μmol/g (see Tom Brown, Dorcas J. S.Brown. Modern machine-aided methods of oligodeoxyribonucleotide synthesis. In: F. Eckstein, editor. Oligonucleotides and Analogues A Practical Approach. Oxford: IRL Press, 1991: 13-14).

Elongation of the Oligonucleotide

The coupling of phosphoramidites (A(bz), G(ibu), 5-methyl-C(bz)) or T-β-cyanoethyl-phosphoramidite) is performed by using a solution of 0.1 M of the 5'-O-DMT-protected amidite in acetonitrile and DCI (4,5-dicyanoimidazole) in acetonitrile (0.25 M) as activator. The thiolation is carried out by using xanthane hydride (0.01 M in acetonitrile:pyridine 10%). The rest of the reagents are the ones typically used for oligonucleotide synthesis. The protocol provided by the supplier was conveniently optimised.

| Purification by RP-HPLC: | |
|---|---|
| Column: | Xterra $RP_{18}$ |
| Flow rate: | 3 mL/min |
| Buffers: | 0.1 M ammonium acetate pH 8 and acetonitrile |

Abbreviations
DMT: Dimethoxytrityl
DCI: 4,5-Dicyanoimidazole
DMAP: 4-Dimethylaminopyridine
DCM: Dichloromethane
DMF: Dimethylformamide
THF: Tetrahydrofurane
DIEA: N,N-diisopropylethylamine
PyBOP: Benzotriazole-1-yl-oxy-tris-pyrrolldino-phosphonium hexafluorophosphate
Bz: Benzoyl
Ibu: Isobutyryl Large-scale Synthesis of Oligonucleotides:

Oligonucleotides in large scale were synthesized using the phosphoramidite approach on an ÄKTA oligopilot in scales from 200 μmole to 1 mmole. After the DMT-OFF-synthesis of the oligo and following DEA-treatment, also performed on the syntheziser. The cleavage of the oligonucleotide from the solid support, and the removal of the protecting groups was done by treatment with aqueous ammonia for 12 hours at 55° C. The oligonucleotides were then purified by ion-exchange (IEX) on an ÄKTA pilot. The desalting was performed on Sephadex™ G-25 Medium followed by freeze-drying. The oligonucleotides were characterized by IEX-HPLC, CGE and ESI-MS.

The coupling of DNA-phosphoramidites (A(bz), C(bz), G(ibu) and (T)) and LNA-phosphoramidites (C(bz) and (T)) is performed by using a 0.2 M solution of the amidite in acetonitril, and a 0.75 M DCI (4,5-dicyanoimidazole) as activator. The thiolation is carried out by using xanthan hydride (0.0175 M in acetonitril:pyridine 20%). The rest of the reagents are the ones typically used for oligonucleotide synthesis.

Example 3

Design of the Oligomeric Compound

TABLE 1

Oligomeric compounds of the invention
In the present application, the oligomeric compounds are referred to by means of the specified sequence number, e.g. "SEQ ID NO: 15". The compound "SEQ ID NO: 56" is also called obilmersen sodium and is used herein as a reference compound.

| SEQ ID NO: | Sequence | Design |
|---|---|---|
| | Complementary 18mers | |
| 1 | $T_sC_st_sc_sc_sc_sa_sg_sc_sg_st_sg_sc_sg_sc_sC_sA_st$ | gap 13 |
| 2 | $T_sC_sT_sc_sc_sc_sa_sg_sc_sg_st_sg_sc_sg_sC_sC_sA_st$ | gap 11 |
| 3 | $T_sC_sT_sC_sc_sc_sa_sg_sc_sg_st_sg_sc_sG_sC_sC_sA_st$ | gap 9 |
| 4 | $t_sC_sT_sC_sc_sc_sa_sg_sc_sg_st_sg_sc_sg_sC_sC_sA_st$ | gap 10 |
| 5 | $T_sC_sT_sc_sc_sc_sa_sg_sc_sg_st_sg_sc_sg_sC_sC_sA_sT$ | gap 11 |

TABLE 1-continued

Oligomeric compounds of the invention
In the present application, the oligomeric compounds are referred
to by means of the specified sequence number, e.g.
"SEQ ID NO: 15". The compound "SEQ ID NO: 56" is also
called obilmersen sodium and is used herein as a reference compound.

| SEQ ID NO: | Sequence | Design |
|---|---|---|
| 6 | $T^α_sC^α_sT^α_sc_sc_sc_sa_sg_sc_sg_st_sg_sc_sg_sC^α_sC^α_sA^α_st$ | gap 11 |
| 7 | $t_sC^α_sT^α_sC^α_sc_sc_sa_sg_sc_sg_st_sg_sc_sg_sC^α_sC^α_sA^α_st$ | gap 10 |
| | Complementary 16mers | |
| 8 | $C_sT_sc_sc_sc_sa_sg_sc_sg_st_sg_sc_sg_sC_sC_sa$ | gap 11 |
| 9 | $C^α_sT^α_sc_sc_sc_sa_sg_sc_sg_st_sg_sc_sg_sC^α_sC^α_sa$ | gap 11, α-L-LNA |
| 10 | $C_sT_sc_sc_sc_sa_sg_sc_sg_st_sg_sc_sg_sC_sC_sA$ | LNA 3'-end |
| 11 | $C_sT_sc_sc_sc_sa_sg_sc_sg_st_sg_sc_sg_sC_sC_sA$ | LNA 3'-end |
| 12 | $C_sT_sC_sc_sc_sa_sg_sc_sg_st_sg_sc_sg_sG_sC_sC_sa$ | gap 9 |
| 13 | $C_sT_sC_sc_sc_sa_sg_sc_sg_st_sg_sc_sG_sG_sC_sC_sa$ | gap 7 |
| 14 | $C_sT_sC_sc_sc_sa_sg_sc_sg_st_sg_sc_sG_sC_sC_sA$ | gap 9 |
| | $c_st_sc_sc_sc_sa_sM_sc_sg_st_sg_sc_sg_sc_sa$, 16mers | |
| 15 | $C_sT_sc_sc_sc_sa_sa_sc_sg_st_sg_sc_sg_sC_sC_sa$ | gap 11 |
| 16 | $C^α_sT^α_sc_sc_sc_sa_sa_sc_sg_st_sg_sc_sg_sC^α_sC^α_sa$ | gap 11, α-L-LNA |
| 17 | $C_sT_sC_sc_sc_sa_sa_sc_sg_st_sg_sc_sg_sC_sC_sa$ | gap 9 |
| 18 | $C_sT_sC_sc_sc_sa_st_sc_sg_st_sg_sc_sg_sC_sC_sa$ | gap 9 |
| 19 | $C_sT_sC_sC_sc_sa_sa_sc_sg_st_sg_sc_sG_sC_sC_sa$ | gap 7 |
| 20 | $C_sT_sc_sc_sc_sa_sa_sc_sg_st_sg_sc_sG_sC_sC_sa$ | gap 10 |
| | $c_st_sc_sc_sc_sa_sg_sc_sg_sM_sg_sc_sg_sc_sc_sa$, 16mers | |
| 21 | $C_sT_sc_sc_sc_sa_sg_sc_sg_sc_sg_sc_sg_sC_sC_sa$ | gap 11 |
| 22 | $C_sT_sC_sc_sc_sa_sg_sc_sg_sc_sg_sc_sG_sC_sC_sa$ | gap 9 |
| 23 | $C_sT_sC_sC_sc_sa_sg_sc_sg_sc_sg_sc_sG_sC_sC_sa$ | gap 7 |
| 24 | $C_sT_sc_sc_sc_sa_sg_sc_sg_sc_sg_sc_sg_sC_sC_sa$ | gap 11 |
| 25 | $C_sT_sc_sc_sc_sa_sg_sc_sg_sc_sg_sc_sg_sC_sC_sa$ | gap 11 |
| | $t_sc_st_sc_sc_sc_sa_sg_sM_sg_st_sg_sc_sg_sc_sa,t$, 18mers | |
| 26 | $TC_sT_sc_sc_sc_sa_sg_sa_sg_st_sg_sc_sg_sC_sC_sA_st$ | gap 11 |
| 27 | $TC_sT_sc_sc_sc_sa_sg_st_sg_st_sg_sc_sg_sC_sC_sA_st$ | gap 11 |
| 28 | $TC_sT_sc_sc_sc_sa_sg_sg_sg_st_sg_sc_sg_sC_sC_sA_st$ | gap 11 |
| | Standards | |
| 29 | $C_sT_sc_sc_sc_sa_sa_sc_sg_st_sg_sc_sg_sC$ | N-1, 3'-end |
| 30 | $C_sT_sc_sc_sc_sa_sa_sc_sg_st_sg_sc_sg_sC$ | N-2, 3'-end (ref.) |
| 31 | $C_sT_sc_sc_sc_sa_sa_sc_sg_st_sg_sc_sg_s$ | N-3, 3'-end (ref.) |
| 32 | $T_sc_sc_sc_sa_sa_sc_sg_st_sg_sc_sg_sC_sC_sa$ | N-1, 5'-end (ref.) |
| 33 | $c_sc_sc_sa_sa_sc_sg_st_sg_sc_sg_sC_sC_sa$ | N-2, 5'-end (ref.) |

TABLE 1-continued

Oligomeric compounds of the invention
In the present application, the oligomeric compounds are referred
to by means of the specified sequence number, e.g.
"SEQ ID NO: 15". The compound "SEQ ID NO: 56" is also
called obilmersen sodium and is used herein as a reference compound.

| SEQ ID NO: | Sequence | Design |
|---|---|---|
| 34 | $c_s c_s a_s a_s c_s g_s t_s g_s c_s g_s C_s C_s a$ | N-3, 5'-end (ref.) |
| 35 | $C_s T_s c_s c_s c_s a_s g_s c_s g_s t_s g_s c_s g_s C_s C$ | N-1, 3'-end |
| 36 | $C_s T_s c_s c_s c_s a_s g_s c_s g_s t_s g_s c_s g_s C$ | N-2, 3'-end (ref.) |
| 37 | $C_s T_s c_s c_s c_s a_s g_s c_s g_s t_s g_s c_s g_s$ | N-3, 3'-end (ref.) |
| 38 | $T_s c_s c_s c_s a_s g_s c_s g_s t_s g_s c_s g_s C_s C_s a$ | N-1, 5'-end (ref.) |
| 39 | $c_s c_s c_s a_s g_s c_s g_s t_s g_s c_s g_s C_s C_s a$ | N-2, 5'-end (ref.) |
| 40 | $c_s c_s a_s g_s c_s g_s t_s g_s c_s g_s C_s C_s a$ | N-3, 5'-end (ref.) |
| 41 | $C_s T_s c_s c_s c_s a_s g_s c_s g_s t_s g_s c_s g_s c_s C_s A_s t$ | gap 12 |
| 42 | $C_s T_s C_s c_s c_s a_s g_s c_s g_s t_s g_s c_s g_s C_s C_s A_s t$ | gap 10 |
| 43 | $C_s T_s C_s C_s c_s a_s g_s c_s g_s t_s g_s c_s G_s C_s C_s A_s t$ | gap 8 |
| 44 | $T_s C_s t_s c_s c_s c_s a_s g_s c_s g_s t_s g_s c_s g_s C_s C_s a$ | gap 12 |
| 45 | $T_s C_s T_s c_s c_s c_s a_s g_s c_s g_s t_s g_s c_s G_s C_s C_s a$ | gap 10 |
| 46 | $T_s C_s T_s C_s c_s c_s a_s g_s c_s g_s t_s g_s C_s G_s C_s C_s a$ | gap 8 |
| 47 | $T_s C_s t_s c_s c_s c_s a_s g_s c_s g_s t_s g_s c_s G_s C_s c$ | gap 11 |
| 48 | $T_s C_s T_s c_s c_s c_s a_s g_s c_s g_s t_s g_s c_s G_s C_s c$ | gap 9 |
| 49 | $T_s C_s T_s C_s c_s c_s a_s g_s c_s g_s t_s G_s C_s G_s C_s c$ | gap 7 |
| 50 | $T_s C_s c_s c_s a_s g_s c_s g_s t_s g_s c_s g_s c_s C_s A_s t$ | gap 11 |
| 51 | $T_s C_s C_s c_s a_s g_s c_s g_s t_s g_s c_s g_s C_s C_s A_s t$ | gap 9 |
| 52 | $T_s C_s C_s C_s a_s g_s c_s g_s t_s g_s c_s G_s C_s C_s A_s t$ | gap 7 |
| 53 | $TC_s C_s T_s c_s c_s c_s a_s g_s c_s a_s t_s g_s c_s g_s C_s C_s A_s t$ | gap 11 |
| 54 | $TC_s C_s T_s c_s c_s c_s a_s g_s c_s t_s t_s g_s c_s g_s C_s C_s A_s t$ | gap 11 |
| 55 | $TC_s C_s T_s c_s c_s c_s a_s g_s c_s c_s t_s g_s c_s g_s C_s C_s A_s t$ | gap 11 |
| 56 | $t_s c_s t_s c_s c_s c_s a_s g_s c_s g_s t_s g_s c_s g_s c_s c_s a_s t$ | Reference |
| 57 | $T_s C_s T_s c_s c_s c_s a_s g_s c_s a_s t_s g_s t_s g_s C_s C_s A_s t$ | 2 mismatches |
| 58 | $A_s C_s c_s g_s c_s g_s t_s g_s c_s g_s a_s c_s c_s C_s T_s c$ | Reference; reversed polarity |
| 59 | $t_s{}^m c_s t_s{}^m c_s{}^m c_s a_s g_s{}^m c_s g_s t_s g_s{}^m c_s g_s{}^m c_s{}^m c_s a_s t$ | Reference |
| 60 | $C_s T_s c_s c_s c_s a_s a_s c^m{}_s g_s t_s g_s c^m{}_s g_s C_s C_s a$ | gap 11 |
| 61 | $C_s T_s{}^m c_s{}^m c_s{}^m c_s a_s a_s{}^m c_s g_s t_s g_s{}^m c_s g_s C_s C_s a$ | gap 11 |
| | Primers | |
| 62 | catgtgtgtggagagcgtcaa | |
| 63 | gccggttcaggtactcagtca | |
| 64 | FAM-cctggtggacaacatcgccdgt-TAMRA | |

In Table 1, capital letters denote LNA nucleotides, superscript "α" denotes that the LNA nucleotide is an alpha-L-LNA nucleotide (i.e. an LNA analogue nucleotide), and subscript "S" denotes that the neighbouring nucleotides are linked by a phosphorothioate group. All LNA-C monomers are methyl-C.

Example 4

In vitro Model: Cell Culture

The effect of antisense compounds on target nucleic acid expression can be tested in any of a variety of cell types provided that the target nucleic acid is present at measurable levels. Target can be expressed endogenously or by transient or stable transfection of a nucleic acid encoding said nucleic acid.

The expression level of target nucleic acid can be routinely determined using, for example, Northern blot analysis, Quantitative PCR, Ribonuclease protection assays or other quantitative methods. The following cell types are provided for illustrative purposes, but other cell types can be routinely used, provided that the target is expressed in the cell type chose.

Cells were cultured in the appropriate medium as described below and maintained at 37° C. at 95-98% humidity and 5% $CO_2$. Cells were routinely passaged 2-3 times weekly.

15PC3: The human prostate cancer cell line 15PC3 was kindly donated by Dr. F. Baas, Neurozintuigen Laboratory, AMC, The Netherlands and was cultured in DMEM (Sigma)+10% fetal bovine serum (FBS)+Glutamax I+gentamicin.

PC3: The human prostate cancer cell line PC3 was purchased from ATCC and was cultured in F12 Coon's with glutamine (Glbco)+10% FBS+gentamicin.

518A2: The human melanoma cancer cell line 518A2 was kindly donated by Dr. B. Jansen, Section of experimental Oncology, Molecular Pharmacology, Department of Clinical Pharmacology, University of Vienna and was cultured in DMEM (Sigma)+10% fetal bovine serum (FBS)+Glutamax I+gentamicin.

Example 5

In vitro model: Treatment with Antisense Oligonucleotide

The cells were treated with oligonucleotide using the cationic liposome formulation LipofectAMINE 2000 (Gibco) as transfection vehicle.

The cells were seeded in 12-well cell culture plates (NUNC) and treated at confluence of 80-90%. Oligomer concentrations used ranged from 0.2 nM to 100 nM final concentration. Formulation of oligomer-lipid complexes were carried out essentially as described in Dean et al. (Journal of Biological Chemistry 1994, 269, 16416-16424) using serum-free OptiMEM (Gibco) and a final lipid concentration of 10 µg/ml LipofectAMINE 2000 in 500 µl total volume.

Cells were transfected by incubation at 37° C. for 4 hours. Subsequently the transfection media was removed and cells were washed before serum-containing media was added. Cells were cultured for different length of time ranging from 0-72 hours.

Example 6

In Vitro Model: Extraction of RNA and cDNA Synthesis

Total RNA Isolation

Total RNA was isolated either using either RNeasy mini kit (Qiagen cat. No. 74104) or the Trizol reagent (Life technologies cat. No. 15596). For RNA isolation from cell lines, RNeasy is the preferred method, and for tissue samples Trizol is the preferred method.

Total RNA was isolated from cell lines using the Qiagen RNA OPF Robot—BIO Robot 3000 according to the protocol provided by the manufacturer.

Tissue samples were homogenised and total RNA was isolated using the Trizol reagent protocol provided by the manufacturer.

First Strand Synthesis

First strand synthesis was performed using OmniScript Reverse Transcriptase kit (cat# 205113, Qiagen) according to the manufacturers instructions.

For each sample 0.5 µg total RNA was adjusted to 12 µl each with RNase free $H_2O$ and mixed with 2 µl poly $(dT)_{12-18}$ (2.5 µg/ml) (Life Technologies, GibcoBRL, Roskilde, DK), 2 µl dNTP mix (5 mM each dNTP), 2 µl 10× Buffer RT, 1 µl RNAguard™Rnase INHIBITOR (33.3 U/ml), (cat# 27-0816-01, Amersham Pharmacia Biotech, Hørsholm, DK) and 1 µl OmniScript Reverse Transcriptase (4 U/µl) followed by incubation at 37° C. for 60 minutes and heat inactivation of the enzyme at 93° C. for 5 minutes.

Example 7

In Vitro Model: Analysis of Oligonudeotide Inhibition of Bcl-2 Expression by Real-time PCR Antisense modulation of Bcl-2 expression can be assayed in a variety of ways known in the art. For example, Bcl-2 mRNA levels can be quantitated by, e.g., Northern blot analysis or quantitative PCR. Quantitative real-time PCR is presently preferred. RNA analysis can be performed on total cellular RNA or mRNA.

Methods of RNA isolation and RNA analysis such as Northern blot analysis are routine In the art and is taught in, for example, Current Protocols in Molecular Biology, John Wiley and Sons.

Quantitative real-time (PCR) can be conveniently accomplished using the commercially available iQ Multi-Color Real Time PCR Detection System available from BioRAD Laboratories.

Real-time Quantitative PCR Analysis of Bcl-2 mRNA Levels

Quantitation of mRNA levels was determined by real-time quantitative PCR using the iQ Multi-Color Real Time PCR Detection System (BioRAD) according to the manufacturers instructions.

Real-time Quantitative PCR is a technique well-known in the art and is taught in for example Heid et al. Real time quantitative PCR, Genome Research (1996), 6: 986-994.

Platinum Quantitative PCR SuperMix UDG 2×PCR master mix was obtained from Invitrogen cat# 11730. Primers and TaqMan® probes were obtained from MWG-Biotech AG, Ebersberg, Germany.

Probes and primers to human Bcl-2 were designed to hybridise to a human Bcl-2 sequence, using published sequence information (GenBank accession number NM 001168, incorporated herein as SEQ ID NO: 1001).

For human Bcl-2 the PCR primers were:

```
forward primer:
                                              (SEQ ID NO: 62)
5'catgtgtgtggagagcgtcaa 3'
(final concentration in the assay; 0.6 µM)
``` reverse primer: 5' gccggttcaggtactcagtca 3' (final concentration in the assay; 0.6 µM) (SEQ ID NO: 63) and the PCR probe was: 5' FAM-cctggtggacaacatcgccctgt-TAMRA 3' (final concentration in the assay; 0.1 µM) (SEQ ID NO: 64)

Glyceraldehyde-3-phosphate dehydrogenase (GAPDH) mRNA quantity was used as an endogenous control for normalizing any variance in sample preparation.

The sample content of human GAPDH mRNA was quantified using the human GAPDH ABI Prism Pre-Developed TaqMan Assay Reagent (Applied Biosystems cat. No. 4310884E) according to the manufacturer's instructions.

Real Time PCR

The cDNA from the first strand synthesis performed as described hereinabove was diluted 2-20 times, and analyzed by real time quantitative PCR. The primers and probe were mixed with 2× Platinum Quantitative PCR SuperMix UDG (cat. # 11730, Invitrogen) and added to 3.3 µl cDNA to a final volume of 25 µl. Each sample was analysed in triplicates. Assaying 2 fold dilutions of a cDNA that had been prepared on material purified from a cell line expressing the RNA of interest generated standard curves for the assays. Sterile $H_2O$ was used instead of cDNA for the no template control. PCR program: 50° C. for 2 minutes, 95° C. for 10 minutes followed by 40 cycles of 95° C., 15 seconds, 60° C., 1 minutes.

Relative quantities of target mRNA sequence were determined from the calculated Threshold cycle using the iCycler iQ Real-time Detection System software. (See Table 3)

Example 8

In vitro analysis: Western blot analysis of Bcl-2 protein levels

Protein levels of Bcl-2 can be quantitated in a variety of ways well-known in the art, such as immunoprecipitation, Western blot analysis (immunoblotting), ELISA, RIA (Radio Immuno Assay) or fluorescence-activated cell sorting (FACS) and others. Antibodies directed to Bcl-2 can be identified and obtained from a variety of sources, such as Upstate Biotechnologies (Lake Placid, USA), Novus Biologicals (Littleton, Colo.), Santa Cruz Biotechnology (Santa Cruz, Calif.), DAKO (Glostrup, Denmark) or can be prepared via conventional antibody generation methods. Western blotting:

The effect of Bcl-2 oligoes on Bcl-2 protein levels in vitro was determined by Western Blotting.

Figure 2A:
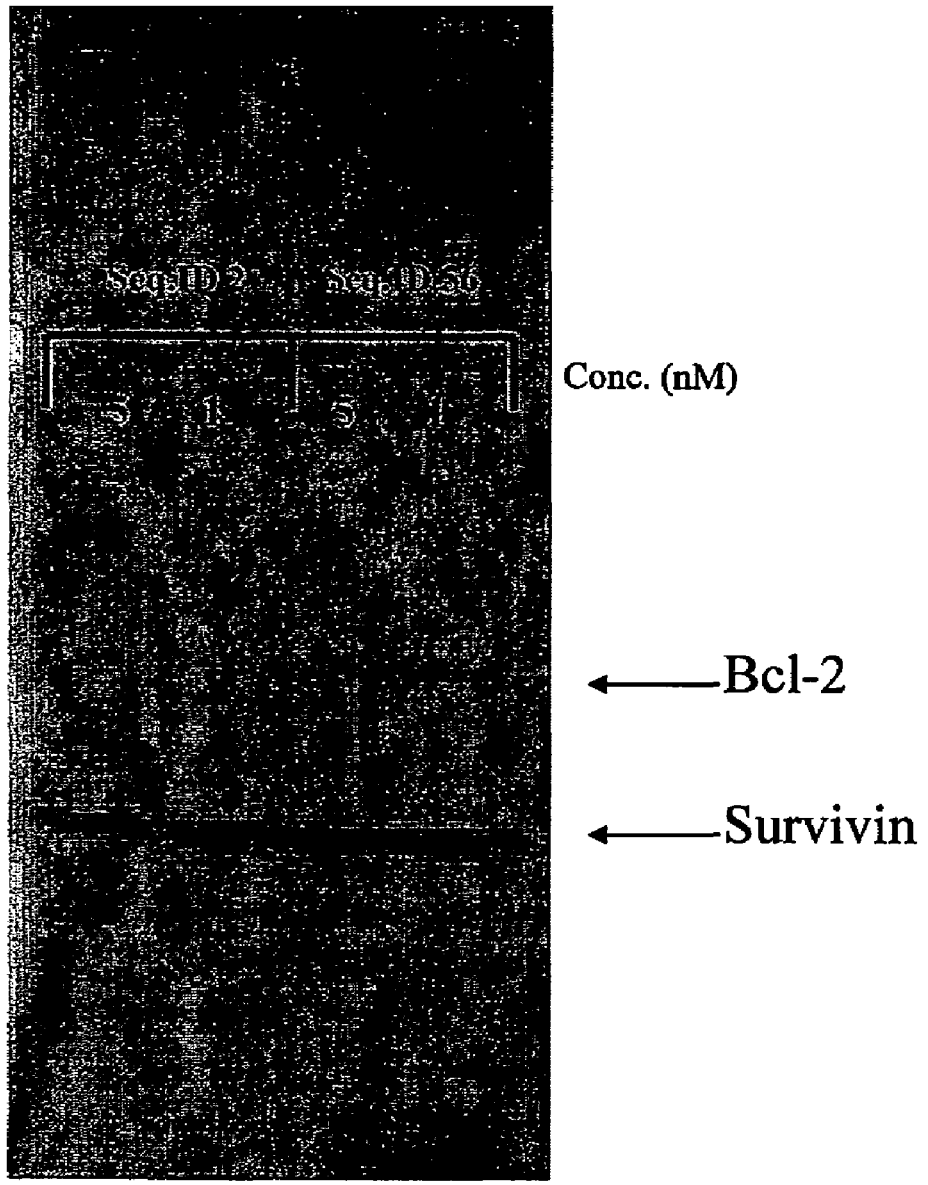
FIG. 2A shows down-regulation of Bcl-2 in 15PC3 cells transfected with LNA oligomeric compounds and analyzed by western blotting and visualized using a chemiluminescense detection system. SEQ ID NO: 2 was significantly more potent than SEQ ID NO: 56 (reference). The survivin protein served as a control.
Figure 2B:
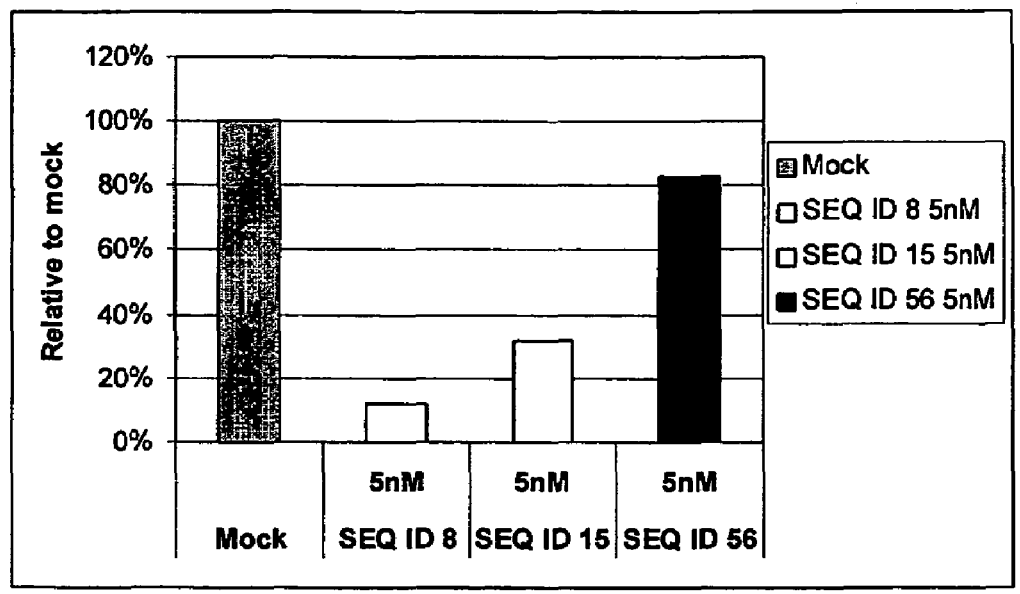
FIG. 2B shows a Western blot. 518A2 cells were lipofected with 5 nM of SEQ ID NO: 56 (reference), SEQ ID NO: 8 and SEQ ID NO: 15, respectively. Protein was analysed after 48 hours. SEQ ID NO: 15 remains active through out this time span. The graph shows the data when normalised to tubulin.
Figure 2B:
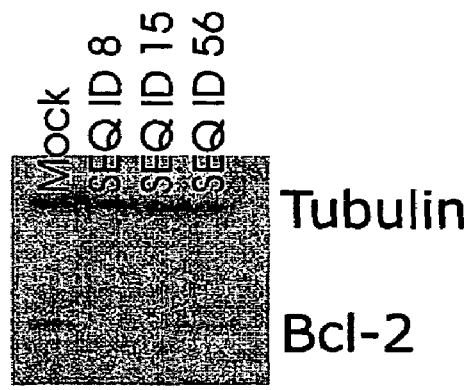
Figure 2C:
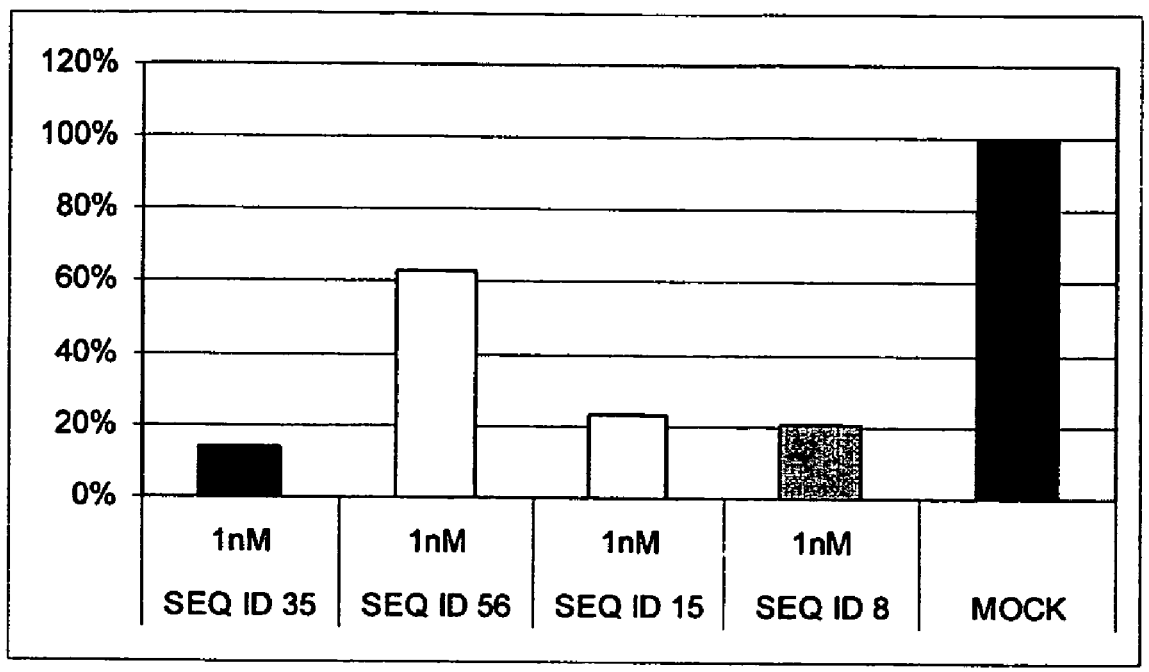
FIG. 2C shows a Western blot. 518A2 cells were lipofected with 5 nM of SEQ ID NO: 56, SEQ ID NO: 8, SEQ ID NO: 15 and SEQ ID NO: 35, respectively, which is the n-1 15-mer version of SEQ ID NO: 15. Protein was analysed at 48 hours. SEQ ID NO: 35 was as potent as SEQ ID NO: 15. Data were normalised to tubulin.
Figure 6:
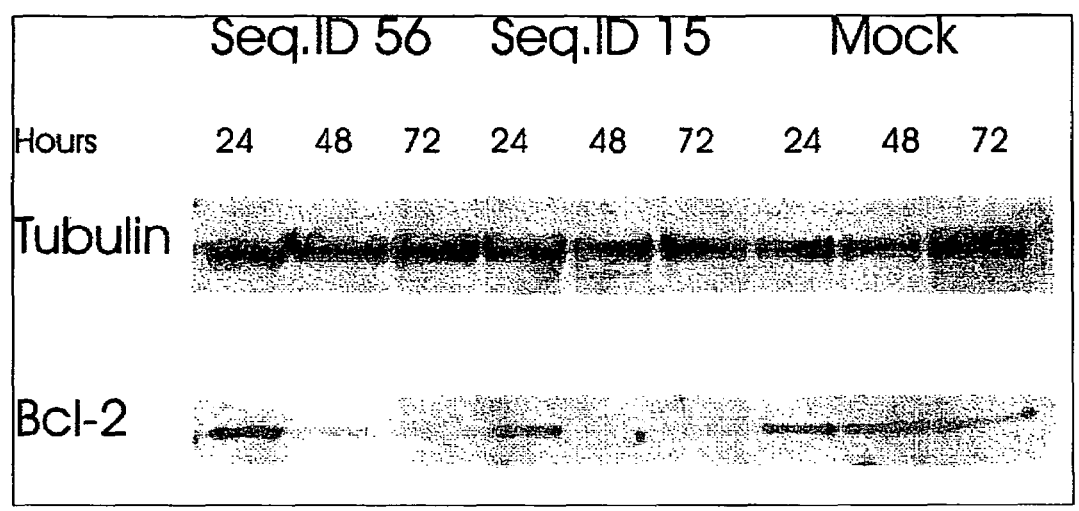
FIG. 6 shows a Western blot. 518A2 cells were lipofected with 10 nM of SEQ ID NO: 56 (reference) and SEQ ID NO: 15, respectively. Protein was analysed at 24 hours, 48 hours and 72 hours. SEQ ID NO: 15 remains active through out this time span. At 24 hours the Bcl-2 protein is still visible due the length of the protein half-life.

Cells were transfected as described in Example 5. At timepoints ranging from 0-72 hours after transfection, cells were harvested, lysed in 2.5% SDS, 5 mM DTT and 6 M urea supplemented with protease inhibitor cocktail tablets (Roche). Total protein concentrations were measured using a Bradford reagent. 150 µg total proteins were run on 12% Bis-Tris gels in MOPS buffer and blotted onto PVDF membranes according to manufacturer's recommendations (Invitrogen). After overnight incubation in blocking buffer (Invitrogen), the membrane was incubated two hours with monoclonal anti-Bcl-2 (DAKO) and anti-Survivin antibodies (Novus Biologicals 500-205 clone 60.11) or anti-tubulin (NeoMarkers) followed by one hour incubation in secondary antibodies. A chromogenic immunodetection kit (Invitrogen) was used to visualize Bcl-2, Survivin or tubulin. Alternatively, the membrane was incubated with HRP conjugated mouse immunoglobulins (DAKO) followed by incubation with ECL$^+$ Plus reagent (Amersham) and visualized using VersaDoc chemiluminescence detection system. See FIGS. 1, 2A, 2B and 2C. FIG. 6 shows duration of the activity of SEQ ID NO: 15 on Bcl-2 protein. Table 2 shows the chemiluminescense values for a gel with 10 nM and 10 nM compound concentration (gel not shown). FIG. 2A shows gel from a similar experiment but with other doses (1 nM and 5 nM).

TABLE 2

| Oligomeric compound and concentration | Amount of Bcl-2 (%) normalized to SEQ ID NO: 56, 10 nM |
|---|---|
| SEQ ID NO: 56 (ref.), 10 nM | 100 |
| SEQ ID NO: 56 (ref.), 100 nM | 72 |
| SEQ ID NO: 2, 10 nM | 33 |
| SEQ ID NO: 2, 100 nM | 4 |

Example 9

In Vitro Analysis: Antisense Inhibition of Human Bcl-2 Expression Using Antisense Oligonucleotides In accordance with the present invention, a series of oligonucleotides were designed to hybridise to a specific region of the human Bcl-2 mRNA, i.e. the region around the translation initiation codon. The oligonucleotides of different design and length are shown in Table 1. Oligomeric compounds were evaluated for their potential to knockdown Bcl-2 in 15PC3 and 518A2 through transfection into these cell lines. Bcl-2 transcript steady state was monitored by Real-time PCR and normalised to the GAPDH transcript steady state level. Table 3 shows a series of potent compounds compared to SEQ ID NO: 56 (Oblimersen sodium; a fully modified phosporothioate; reference).

TABLE 3

Bcl-2 mRNA expression determined by realtime PCR. 15PC3 or 518A2 cells were transfected with the indicated concentration of the oligomeric compound, and RNA was extracted after 24 hours incubation. Down-regulation is presented relative to mock treated.

| | Cell line: | | | | | |
|---|---|---|---|---|---|---|
| | 15PC3 | | | 518A2 | | |
| | Concentration (nM) | | | | | |
| SEQ ID NO: | 1 | 5 | 25 | 1 | 5 | 25 |
| 56 (reference) | 0% | 70% | 88% | | 42% | 66% |
| 59 (reference) | 29% | 70% | 90% | | | |
| 1 | 72% | 87% | 91% | | | |
| 2 | 74% | 92% | 89% | | 72% | 89% |
| 3 | 34% | 45% | 84% | | | |
| 4 | 53% | 82% | 90% | | 78% | 90% |
| 8 | 61% | 80% | ND | 44% | 60% | 82% |
| 12 | 62% | 92% | 91% | | 78% | 92% |
| 13 | 36% | ND | 60% | | | |
| 15 | 24% | 79% | 89% | | 72% | 84% |
| 18 | 0% | 71% | 88% | | | |
| 19 | 0% | 0% | 37% | | | |
| 21 | 23% | 80% | 89% | | 74% | 86% |
| 23 | 45% | 62% | 70% | | | |
| 24 | 39% | 85% | 92% | | 70% | 82% |
| 57 | 0% | 37% | 91% | | 61% | 81% |
| 16 | | | | 18% | 36% | 68% |
| 9 | | | | 26% | ND | 78% |

Example 10

Apoptosis Induction by LNA Antisense Oligomeric Compounds

Figure 3A:
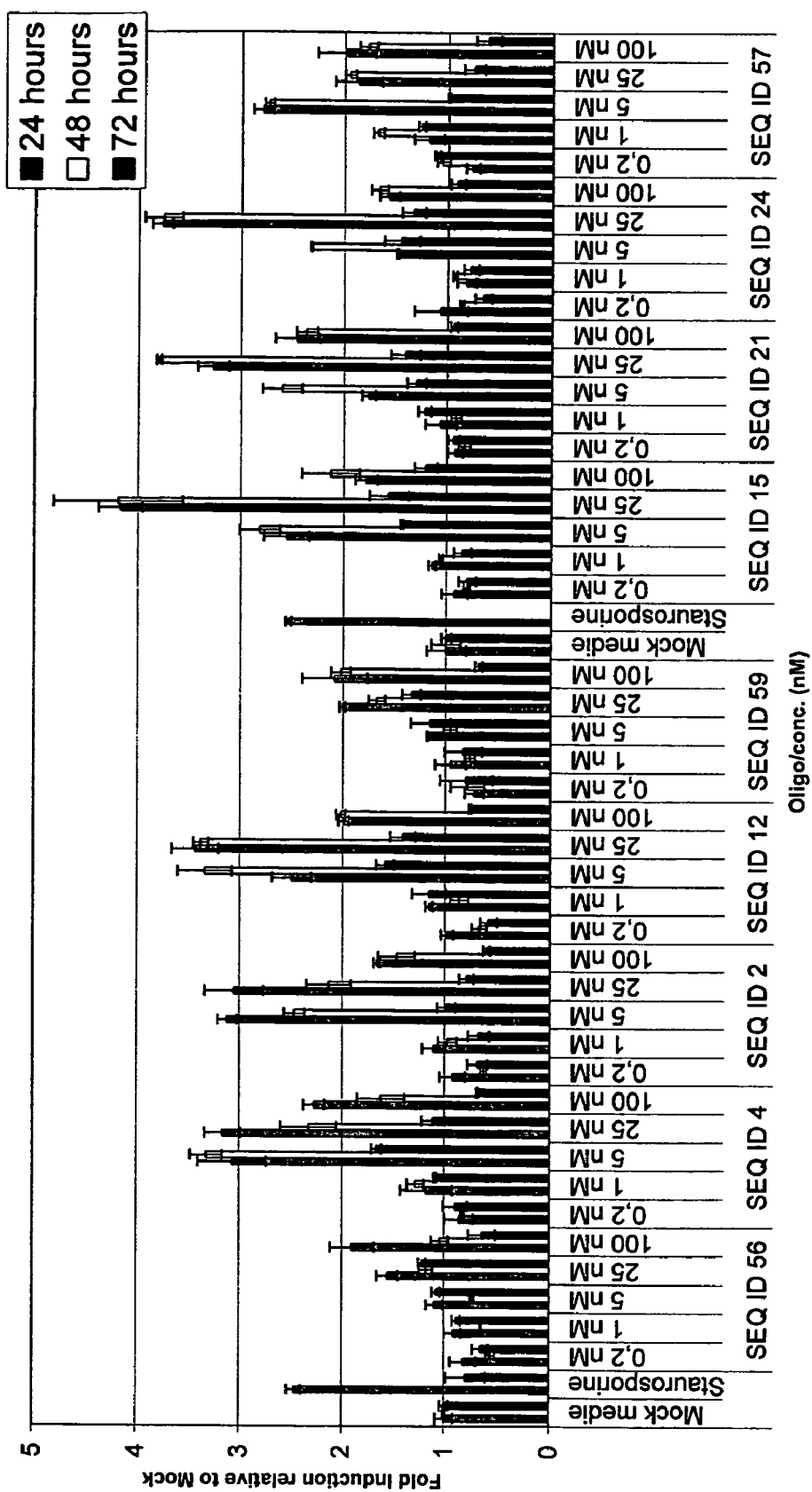
FIG. 3A shows the induction of apoptosis measured by activity of Caspase 3/7 by LNA containing compound in 518A2 cells after 24, 48 and 72 h. The LNA oligomeric SEQ ID NOS: 2, 4, 12, 15, 21, 24 and 57 induced apoptosis more efficiently than SEQ ID NO: 56 (reference) and the corresponding cytosine methylated compound called SEQ ID NO: 59. Lower values of Caspase 3/7 at the later time points (e.g. at 72 h) is due to cell death through apoptosis at earlier activation of Caspase 3/7. Thus, maximum activation has been reached before the time of monitoring.
Figure 3B:
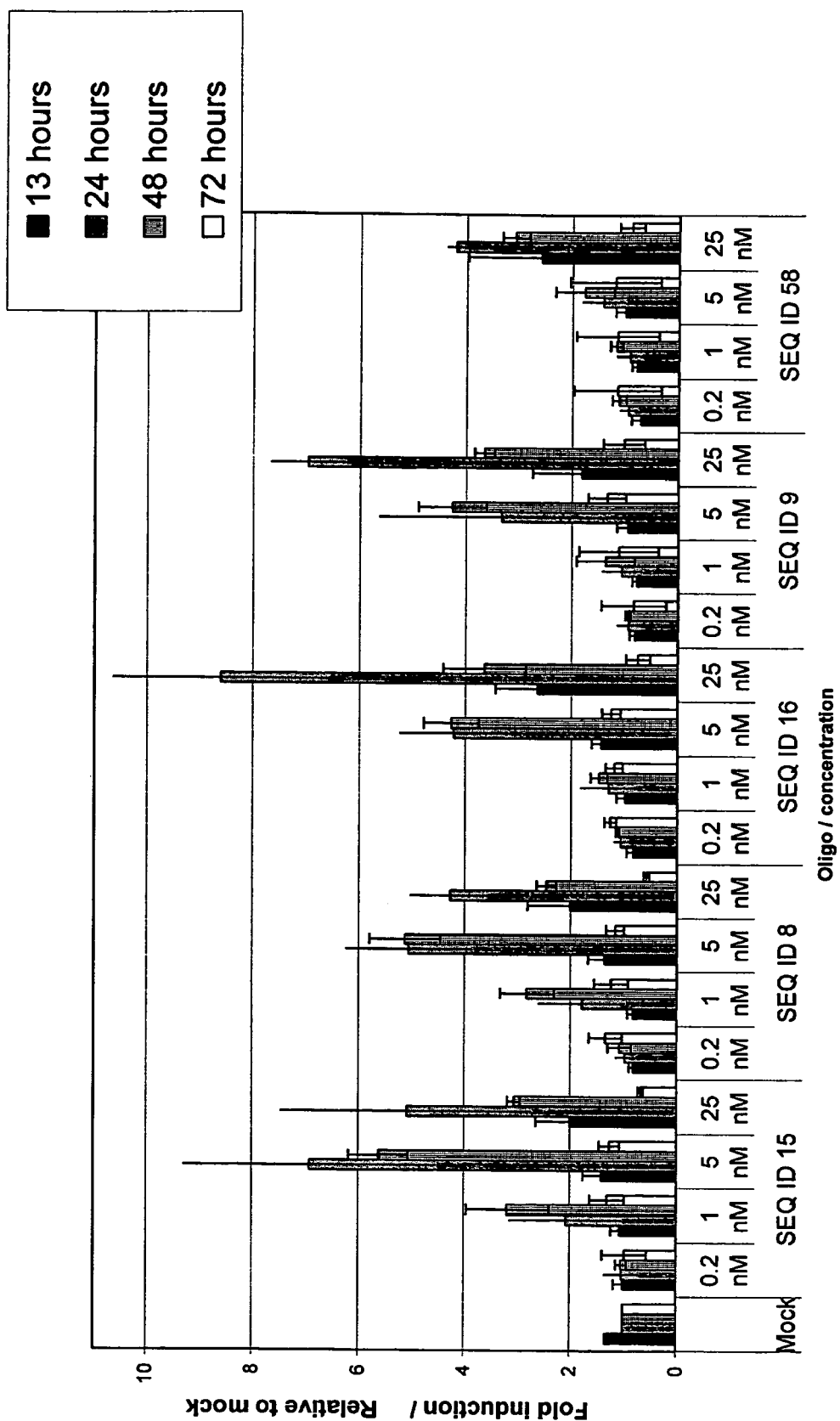
FIG. 3B shows the induction of apoptosis measured by activity of Caspase 3/7 by LNA containing compound in 518A2 cells after 13, 24, 48 and 72 h. The LNA oligomeric compounds SEQ ID NO: 8, 9, 15 and 16 induced apoptosis more efficiently compared to a SEQ ID NO: 58, i.e. a reverse polarity control oligonucleotide also containing LNA.

Cells were seeded to a density of 12,000 cells per well in white 96 well plate (Nunc 136101) in DMEM the day prior to transfection. The next day cells were washed once in prewarmed OptiMEM followed by addition of 72 μl OptiMEM containing 5 μg/ml Lipofectamine2000 (In vitrogen). Cells were incubated for 7 min before adding 18 μl oligonucleotides diluted in OptiMEM. The final oligonucleotide concentration ranged from 0.2 nM to 25 nM. After 4 h of treatment, cells were washed in OptiMEM and 50 μl DMEM containing serum was added. Following treatment with the oligomeric compound, cells were allowed to recover for the period indicated before they were removed from the $CO_2$ incubator and equilibrated to room temperature for 15 min. An equal volume of highly sensitive Caspase 3/7-Glo™ Reagent (Promega) was added directly to the cells in 96 wells, and plates were incubated for 60 min before recording luminescence (luciferase activity) in Luminoskan Ascent instrument from Thermo Labsystems after further 1 min lag period. The luciferase activity is measured as Relative Light Units per seconds (RLU/s). The data were processed in the Ascent software 2.6 and graphs were drawn in excel. (See FIGS. 3A and 3B).

Annexin V-FITC flow cytometry analysis: $0.4 \times 10^6$ HeLa cells were seeded in T25 flasks one day prior to transfection. On the day of transfection the cells were washed once in 37° C. OptiMEM followed by addition of 2.8 ml OptiMEM containing 5 μg/ml Lipofectamine2000 (In vitrogen). Cells were incubated for 7 min before adding 700 μl oligonucleotides diluted in OptiMEM to a final oligonucleotide concentration of 5 nM or 25 nM. Cells transfected without oligonucleotide served as control. After 4 h of treatment cells were washed in OptiMEM and 3 ml culture medium was added. Following oligo treatment cells were allowed to recover for 48 h before they were harvested (by scraping) washed twice in PBS. $0.2 \times 10^6$ cells were incubated with 5 μl Annexin V-FITC and 10 μl propidium iodide (PI-10 mg/ml) and incubated for 15 min at RT In the dark.

Figure 3C:
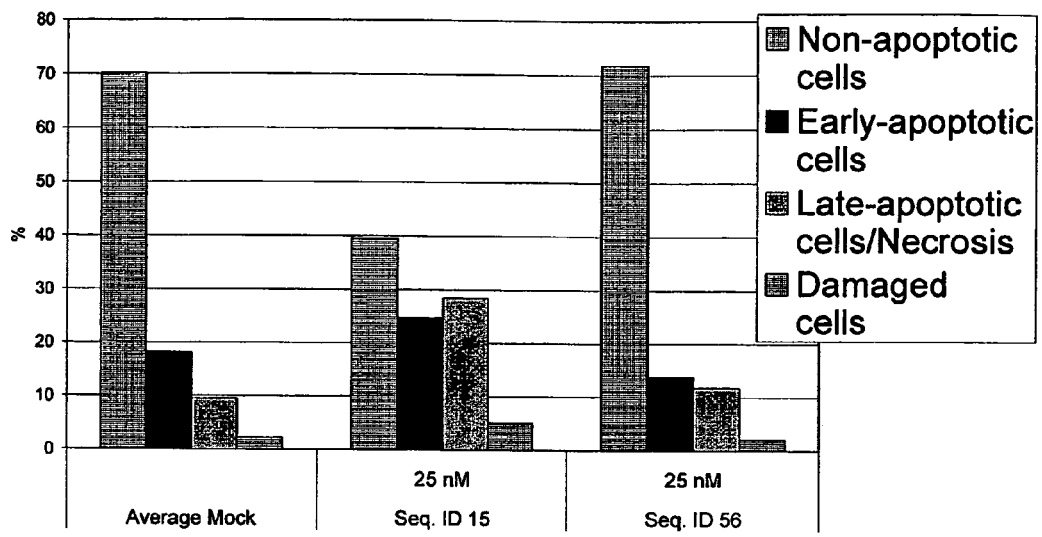
FIG. 3C shows the induction of late-apoptotic cell stage measured by Annexin V-FITC flow cytometry analysis. The HeLa cells treated with the LNA oligomeric compound SEQ ID NO: 15 were classified as more "late apoptotic" or "damaged" compared to mock and SEQ ID NO: 56 (reference) treated cells.
Figure 3D:
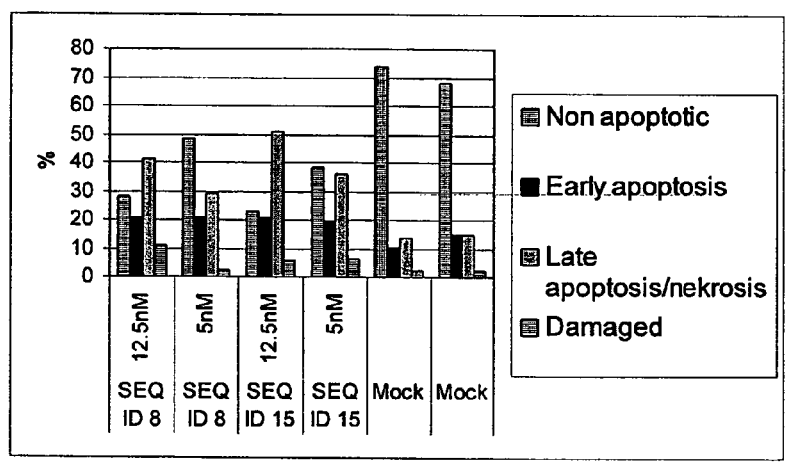
FIG. 3D shows treatment of cells with 5 nM and 12.5 nM SEQ ID NO: 8 and SEQ ID NO: 15 leads to induction of early and late stage apoptosis measured by Annexin V-FITC flow cytometry analysis compared to mock treated cells.

Transfected cells incubated with purified recombinant Annexin V, which block Annexin V binding prior to adding Annexin V-FITC were used to demonstrate specificity and selectivity of the staining. Moreover, TRAIL (Apo2L) induced HeLA cells (0.5 μg/ml) were used as positive control (data not shown). (See FIGS. 3C and 3D)

Example 11

Antisense Oligonucleotide Inhibition of Bcl-2 in Proliferating Cancer Cells

Figure 4:
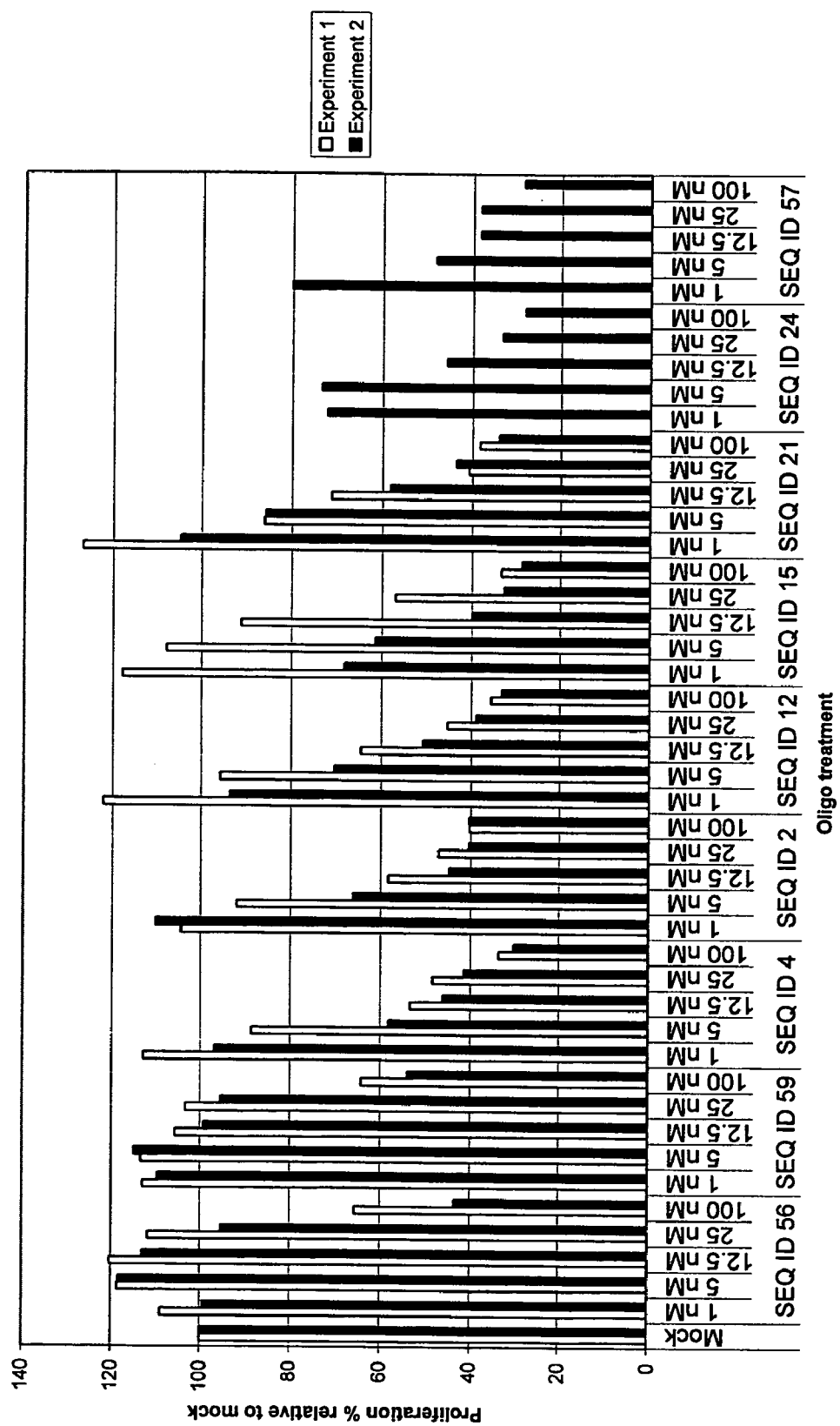
FIG. 4 shows the inhibition of Bcl-2 in proliferating cancer cells (MTS assay), 518A2 cells, measured 48 h after treatment with Bcl-2 LNA oligomeric compound. SEQ ID NOS: 2, 4, 12, 15, 21, 24, and 57 were all more potent inhibitors of proliferation compared to SEQ ID NO: 56 (reference) and the corresponding cytosine methylated compound, SEQ ID NO: 59 (reference). Data were adjusted to a mock treated control. Experiment 1 and Experiment 2 represents two separate experiments.
Figure 5:
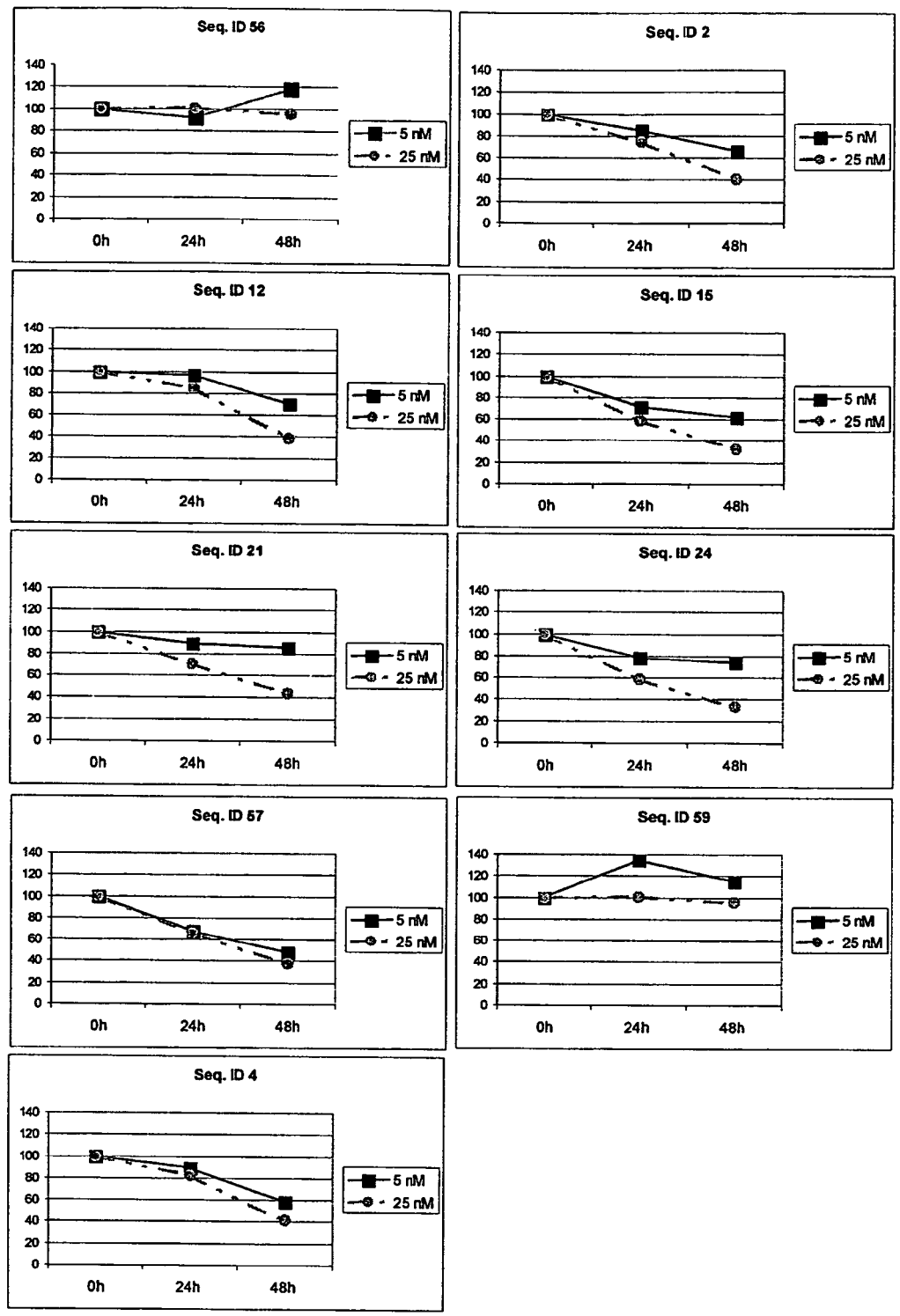
FIG. 5 shows the inhibition of Bcl-2 in proliferating cancer cells, 518A2 cells, measured in a time-course of 0-48 h after treatment with Bcl-2 LNA oligomeric compound. SEQ ID NOS: 2, 4, 12, 15, 21, 24, and 57 were all more potent inhibitors of proliferation compared to the SEQ ID NO: 56 (reference) and the corresponding cytosine methylated compound, SEQ ID NO: 59 (reference). Data were adjusted to a mock treated control.

Cells were seeded to a density of 12000 cells per well in white 96 well plate (Nunc 136101) in DMEM the day prior to transfection. The next day, cells were washed once In prewarmed OptiMEM followed by addition of 72 μl OptiMEM containing 5 μg/ml Lipofectamine2000 (In vitrogen). Cells were incubated for 7 min. before adding 18 μl oligonucleotides diluted in OptiMEM. The final oligonucleotide concentration ranged from 5 nM to 100 nM. After 4 h of treatment, cells were washed In OptiMEM and 100 μl serum containing DMEM was added. Following treatment with the oligomeric compound, cells were allowed to recover for the period indicated, viable cells were measured by adding 20 μl the tetrazolium compound [3-(4,5-dimethyl-2-yl)-5-(3-carboxymethoxyphenyl)-2-(4-sulfophenyl)-2H-tetrazolium, inner salt; MTS] and an electron coupling reagent (phenazine ethosulfate; PES) (Celmter 96® $AQ_{ueous}$ One Solution Cell Proliferation Assay, Promega) per 100 μl DMEM. Viable cells were measured at 490 nm in a Powerwave (Biotek Instruments). Growth rates (ΔOD/h) were plotted against the concentration of the oligomeric compound (see FIGS. 4 and 5).

Example 12

In Vivomodel: Tumour Growth Inhibition of Human Xenotransplanted PC-3 Tumour Cells Grown In Vivo by Systemic Treatment with Antisense Oligonucleotides Female Balb/c athymic nude mice of 6 weeks old were purchased from M&B, Denmark and allowed to acclimatize for at least one week before entering experiments. Human cancer cells typically $3 \times 10^6$ cells suspended in 300 μl matrigel (BD Bioscience), were subcutaneously injected into the flank. For double xenograft models, two tumours are implanted, one in each flank. When the tumour growth was established, typically 5-12 days post tumour cell injection; different antisense oligonucleotides were administrated at 0.01 to 20 mg/kg/day for up to 30 days using IP (intaperitoneal) route of administration either daily, twice a day, every second or third day or weekly. Control animals received saline alone for the same period and by the same administration route. Each experimental group included at least 5 mice. Anti-tumour activities were estimated by the inhibition of tumour growth measured by tumour volume. Tumour growth was followed regularly by measuring 2 perpendicular diameters. Tumour volumes were calculated according to the formula in Teicher BA, Tumour Models In Cancer Research. Humana Press, NJ, USA 2002, p. 596: Tumour volume $(mm^3) = L \times W^2 \times 0.5$), where L represents the largest diameter and W is the tumour diameter perpendicular to L. At the end of treatment the animals were sacrificed and tumour weights were measured. Mean tumour volume and weights of groups were compared using Mann-Whitney's test. All analyses were made in SPSS version 11.0 for Windows. See FIGS. 7A, 7B, 7C and 7D.

Example 13

In Vivo Analysis: Inhibition of Bcl-2 in Human Xenotransplanted PC-3 Tumour Cells Grown In Vivo, by Systemic Treatment with Antisense Oligonucleotides Female Balb/c-nude athymic mice of 6 weeks old were purchased from M&B, Denmark and allowed to acclimatize for at least one week before entering experiments. Human cancer cells, typically $3 \times 10^6$ cells suspended in 300 μl matrigel (BD Bioscience), were subcutaneously injected into the flank. For double xenograft models, two tumours are implanted, one in each flank. When the tumour growth was established, typically 5-12 days post tumour cell injection; different antisense oligonucleotides were administrated at 0.01 to 20 mg/kg/day for up to 30 days using IV (intraveneous) or IP (intaperitoneal) either daily, twice a day, every second or third day or weekly. Control animals received saline alone for the same period and by the same administration route. Each experimental group included at least 5 mice. At the end of treatment period mice were anaesthetised and the tumours were excised and either immediately frozen in liquid nitrogen.

To measure if the antisense oligonucleotides have an inhibitory effect on protein levels, Western blot analysis was performed. The tumours were homogenized in lysis buffer (i.e. 20 mM Tris-Cl [pH 7.5]; 2% Triton X-100; 1/100 vol. Protease Inhibitor Cocktail Set III (Calbiochem); 1/100 vol. Protease Inhibitor Cocktail Set II (Calbiochem) at 4° C. with the use of a motor-driven homogeniser. 500 μl lysis buffer was applied per 100 mg tumour tissue. Tumour lysates from each group of mice were pooled and centrifuged at 13.000 g for 5 min at 4° C. to remove tissue debris. Protein concentrations of the tumour extracts were determined using the BCA Protein Assay Reagent Kit (Pierce, Rockford).

The protein extracts (50-100 μg) were fractionated on a gradient SDS-PAGE gel spanning from 4-20% and transferred to PVDF membranes and visualized by aminoblack staining. The expression of Bcl-2 was detected with anti-human Bcl-2 antibody sc-509 (Santa Cruz Biotechnology, Inc. Santa Cruz, Calif., US) or anti-human Bcl-2 antibody (clone101, Zymed) followed by horseradish peroxidase-conjugated anti-goat IgG (DAKO). Immunoreactivity was detected by the ECL Plus (Amersham biotech) and quantitated by a Versadoc 5000 lite system (Bio-Rad).

Example 14

In Vivo: LNA Bcl-2 Oligomeric Compared to the Currently Clinically Tested Oblimersen Sodium (SEQ ID NO: 56) Tested in 518A2 Human Melanoma Xenotransplanted SCID Mice.

Pathogen free female C.B-17 scid/scid (SCID) mice, 4-6 weeks old, tested for leakiness, were obtained from Harlan & Winkelmann (Borchen, Germany). Animals were housed In microisolator cages in laminar flow racks and received autoclaved food and water ad libitum. SCID mice were injected subcutaneously (s.c.) into the left lower flank with $1.5 \times 10^7$ 518 A2 human melanoma cells resuspended in 200 μl PBS. After 10 days, all mice developed palpable s.c. tumours, were randomized to treatment or control groups and treatment was initiated. For continuous s.c administration, mice were anesthetized and miniosmotic pumps (Alzet 2002, Alza, Moutain View, Calif., USA) filled with oligonucleotides in saline solution or saline as vehicle control were implanted subcutaneously into a paraspinal pocket.

Anti-tumour Activity. SEQ ID NO: 56 (reference) was administered by miniosmotic pumps s.c. for 14 days at the standard dose of 7mg/kg/d as reference schedule. The LNA oligomeric compound SEQ ID NO: 15 was administered at 7, 3.5, and 1.75 mg/kg as by continuous s.c. infusion for 14 days. Saline treated animals were used as control.

Tumour growth over time by calliper measurement and tumour weight at the time of the termination of the experiments was the main parameters to be determined.

See FIGS. 8A, 8B, 9, 10A, 10B and 10C showing data on SEQ ID NO: 15 at 1.75 mg/kg. Increasing concentration (7 and 3.5 mg/kg) did not lead to further decrease in tumour weight or tumour volume indicating that the SEQ ID NO: 15 compound has a dose response curve at lower concentrations.

FIG. 11 shows data on SEQ ID NO: 8 at 1 and 7 mg/kg and data on SEQ ID NO: 15 and SEQ ID NO: 56 at 7 mg/kg. No loss in body weight over the period of treatment was observed when administering the SEQ ID NO: 8 compound and the controls showed a similar pattern.

Example 15

Stability of SEQ ID NO: 15 and SEQ ID NO: 8 in Rat Plasma

Figure 12A:
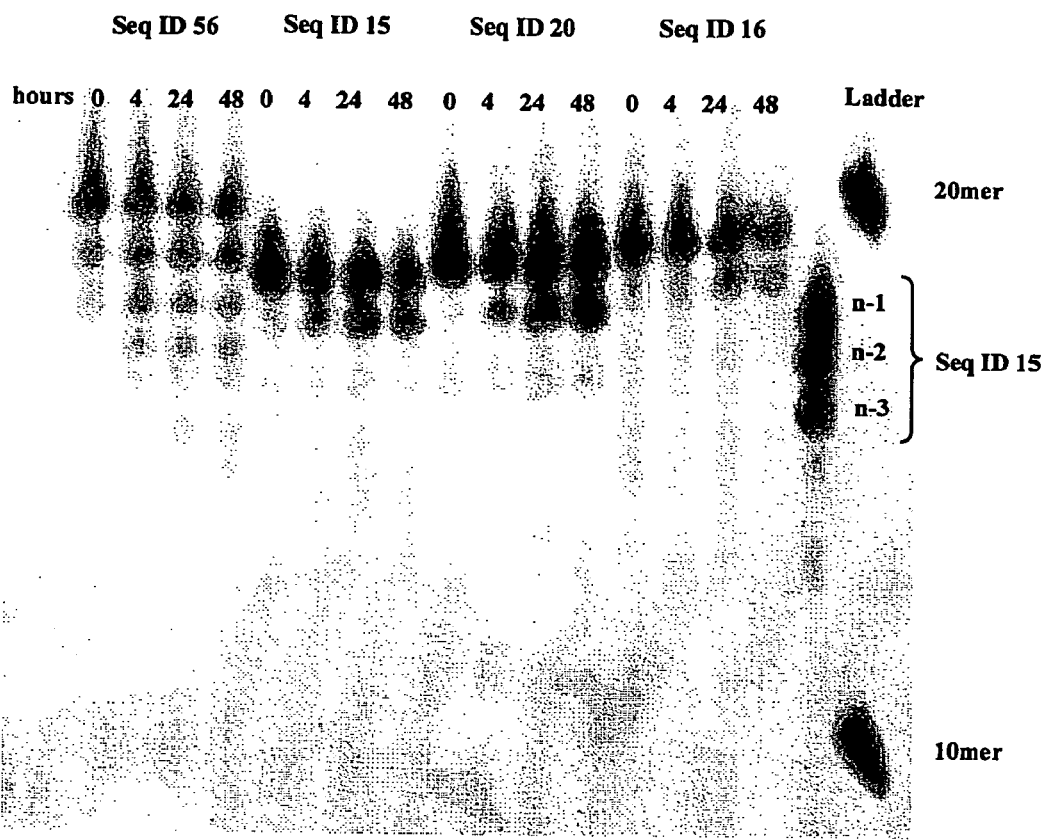
FIG. 12A shows an increased stability of SEQ ID NOS: 15, 16 and 20 in rat plasma (NtacSD male, Li-Heparine (Taconic, M&B)) compared to SEQ ID NO: 56 (reference). The oligonucleotides were incubated at 20 µM concentrations at 37° C. for 0, 4, 24 and 48 hours, respectively. The only degradation fragment present in the sample is the n-1 corresponding oligonucleotide (15 mer) that lacks the DNA residue at the 3'-end. No other degradation fragments can be detected even after 48 h digestion.

Stability of 20 μM SEQ ID NO: 15 in rat plasma (NtacSD male, LI-Heparine (Taconic, M&B)) at 37° C. at different time aliquots: 0, 4, 24 and 48 h. SEQ ID NO: 56 corresponds to SEQ ID NO: 56 (reference). SEQ ID NOS: 20 and 16 are other oligonucleotides that were also tested. The oligonucleotides corresponding to n-1, n-2 and n-3 of SEQ ID NO: 15 (from the 3'-end) were included in order to have a control that would enable the identification of possible digestion fragments of SEQ ID NO: 15. A commercially available ladder was also included (10 and 20mer are visible on the PAGE). (See FIG. 12A)

Figure 12B:
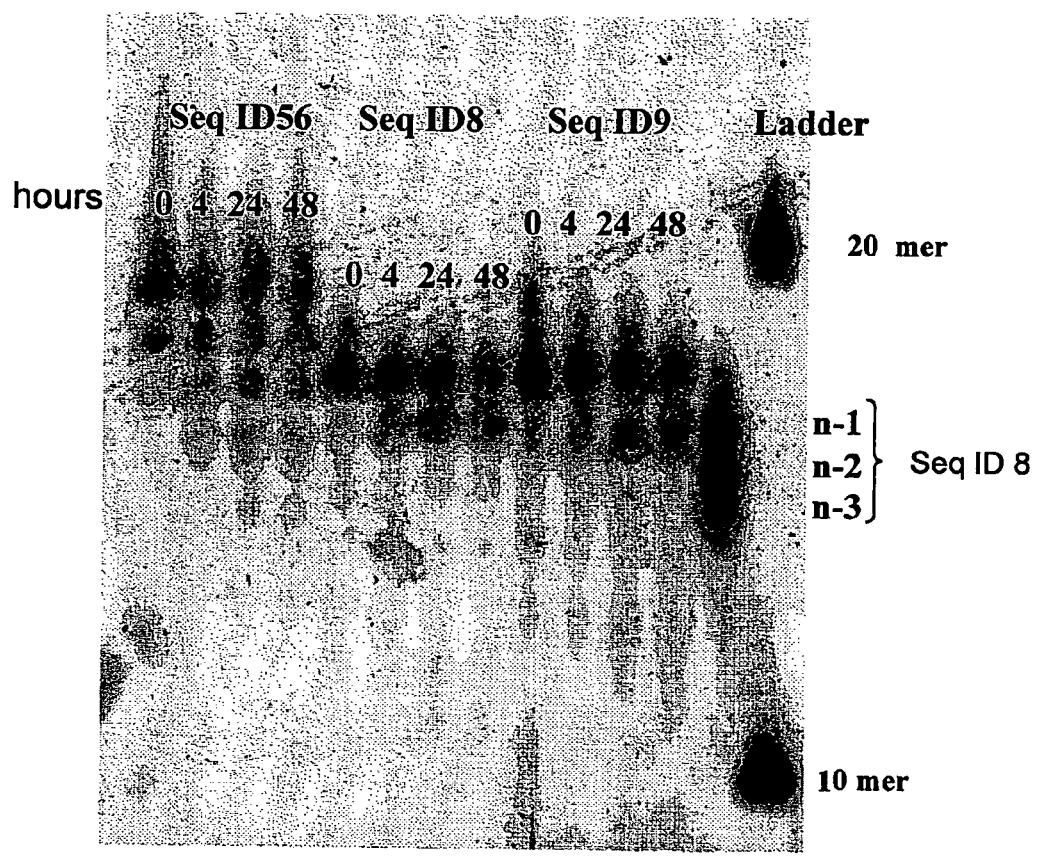
FIG. 12B shows that SEQ ID NO: 8 and 9 exhibit a high stability in rat plasma compared to SEQ ID NO: 56 (reference). The oligonucleotides were incubated at 20 µM concentrations at 37° C. for 0, 4, 24 and 48 hours, respectively. The only degradation fragment present in the sample is the n-1 corresponding oligonucleotide (15 mer) that lacks the DNA residue at the 3'-end. No other degradation fragments can be detected even after 48 h digestion.

Stability of 20 μM SEQ ID NO: 8 in rat plasma (NtacSD male, Li-Heparine (Taconic, M&B)) at 37° C. at different time aliquots: 0, 4, 24 and 48 h. SEQ ID NO: 56 corresponds to SEQ ID NO: 56 (reference). SEQ ID NO: 9 is another oligonucleotide that was also tested. The oligonucleotides corresponding to n-1, n-2 and n-3 of SEQ ID NO: 8 (from the 3'-end) were included in order to have a control that would enable the identification of possible digestion fragments of SEQ ID NO: 8. A commercially available ladder was also included (10 and 20mer are visible on the PAGE). (See FIG. 12B).

The oligomeric compounds, e.g., SEQ ID NO: 8 and SEQ ID NO: 15 were synthesised as oligonucleotides with DNA at the 3' position linked by a phosphorothioate linkage to the adjacent LNA. This 3' DNA moiety can be cleaved off by exonucleases. The degradation product is a 1 nucleotide shortened (N-1) oligomeric compound (SEQ ID NO: 35) that has a substantially Increased resistance to nuclease degradation compared to the full length parent molecule. N-1 compounds (e.g. SEQ ID NO: 35) retain the full activity in the case of e.g. SEQ ID NO: 8 (see FIG. 2C).

Example 16

Tissue Half-life Analysis of SEQ ID NO: 15 in Liver and Kidney

90 NMRI female mice (app. 30 g) were split in groups of 5 and dosed 25 mg/kg SPC 2996 i.v. (10 mL/kg, 2.5 mg/ml) over 30 sec. The control group was dosed with 0.9% saline. The groups were then taken down 30 min, 6 h, 24 h, 48 h, 72 h, and 96 h after injection. Tissue samples were taken and prepared in RNA-later.

Extraction of Oliaonucleotide from Tissue

Approximately 100 mg tissue was homogenized mechanically in 500 μl extraction buffer (0.5% Icefall CA-630, 25 mM Tris pH 8.0, 25 mM EDTA, 100 mM NaCl containing 1 mg/ml RNAse A) and incubated overnight at 37° C. 500 ml was spiked with reference oligonucleotide and extracted by adding 1 ml phenol-isoamyl-choloroform (25:1:24(v/v/v)). The aqueous phase was transferred into a new tube and extracted again. If necessary, the extract was lyophilized.

IEX-HPLC Analysis of Extracted Oliaonucleotide from Tissue Samples

A sample volume of 50 μL was separated over a DNAPac PA-100 (2×250 mm, Dionex) column equipped with a guard column DNAPac PA-100 (2×50 mm, Dionex). The columns were heated to 40° C. The flow rate was 0.25 mL/min. and the detection wavelength 260 nm. A gradient of the mobile phases A: TRIS (20 mM), EDTA (1 mM) and sodium perchlorate (10 mM) pH: 7.6, B: TRIS (20 mM), EDTA (1 mM) and sodium perchlorate (1 M) pH: 7.6, (0-13 min., A:20%, B: 20%; 14-18 min., A: 40%, B: 60%; 22-28 min., A 0%, B: 100%; 33-38 min., A: 80%, B: 20%).

FIG. 13 shows tissue half-life of SEQ ID NO: 15 in liver and kidney from NMRI mice after single dose i.v. adm. (25 mg/kg).

The disclosure of all references mentioned herein are incorporated by reference. The invention has been described with reference to preferred embodiments thereof. However, it will be appreciated that those skilled in the art, upon consideration of this disclosure, may make modifications and improvements within the spirit and scope of the invention.

The invention claimed is:

1. A method for reducing the expression of human Bcl-2 in cells or a tissue, the method comprising contacting the cells or tissue with an oligomer consisting of 16-30 nucleotides joined by internucleoside linkages, the oligomer comprising:

CTcccaacgtgcgCCa (SEQ NO: 15), wherein C is a 5-methyl cytosine beta-D-oxy-LNA or cytosine beta-D-oxy-LNA, T is a thymine beta-D-oxy LNA and a, c, g, and t are deoxyribonucleotides.

2. The method according to claim 1, wherein all internucleoside linkages in the oligomer are phosphorothioate groups.

3. A method according to claim 1 or 2, wherein the contacting step comprises contacting the cell or tissue with a pharmaceutical composition comprising the oligomer and a pharmaceutically acceptable carrier.

4. The method according to claim 1, wherein the reduction of expression of Bcl-2 in the cells or tissue results in cell apoptosis in the cells or tissue.

5. The method according to claim 1, wherein the reduction of expression of Bcl-2 in the cells or tissue results in the reduction or prevention of cell proliferation.

6. A. method of treating a mammal suffering from, or susceptible to a cancer, the method comprising administering to the mammal a therapeutically effective amount of an oligomer consisting of 16-30 nucleotides joined by internucleoside linkages, the oligomer comprising:

CTcccaacgtgcgCCa (SEQ NO: 15), wherein C is a 5-methyl cytosine beta-D-oxy-LNA or cytosine beta-D-oxy-LNA, T is a thymine beta-D-oxy LNA and a, c, g, and t are deoxyribonucleotides.

7. The method according to claim 6, wherein all internucleoside linkages in the oligomer are phosphorothioate groups.

8. The method according to claim 6 or 7, wherein the oligomer is in the form of a pharmaceutical composition comprising the oligomer and an pharmaceutically acceptable carrier.

9. A method of treating a mammal suffering from or susceptible to a disease caused by angiogenesis the method comprising administering to the mammal a therapeutically effective amount of an oligomer consisting of 16-30 nucleotides joined by internucleoside linkages, the oligomer comprising: CTcccaacgtgcgCCa (SEQ NO: 15), wherein C is a 5-methyl cytosine beta-D-oxy-LNA or cytosine beta-D-oxy-LNA, T is a thymine beta-D-oxy LNA and a, c, g, and t are deoxyribonucleotides.

10. The method according to claim 9, wherein all internucleotide linkages in the oligomer are phosphorothioate groups.

11. The method of claim 1 further comprising contacting the cells or tissue with a chemotherapeutic compound.

12. The method of claim 1 further comprising contacting the cells or tissue with a taxane compound.

13. The method of claim 12 wherein the taxane compound is selected from paclitaxel, docetaxel, and taxotere.

14. The method of claim 1 further comprising contacting the cells or tissue with fludarabine.

15. The method of claim 1 further comprising contacting the cells or tissue with dacarbazine.

16. The method of claim 1 further comprising exposing the cells or tissue to radiotherapy.

17. The method of claim 3 wherein the pharmaceutical composition further comprises a chemotherapeutic compound.

18. The method of claim 3 wherein the pharmaceutical composition further comprises a taxane compound.

19. The method of claim 18 wherein the taxane compound is selected from paclitaxel, docetaxel, and taxotere.

20. The method of claim 3 wherein the pharmaceutical composition further comprises fludarabine.

21. The method of claim 3 wherein the pharmaceutical composition further comprises dacarbazine.

22. The method of claim 6 further comprising contacting the cells or tissue with a chemotherapeutic compound.

23. The method of claim 6 further comprising contacting the cells or tissue with a taxane compound.

24. The method of claim 23 wherein the taxane compound is selected from paclitaxel, docetaxel, and taxotere.

25. The method of claim 6 further comprising contacting the cells or tissue with fludarabine.

26. The method of claim 6 further comprising contacting the cells or tissue with dacarbazine.

27. The method of claim 6 further comprising exposing the cells or tissue to radiotherapy.

28. The method of claim 8 wherein the pharmaceutical composition further comprises a chemotherapeutic compound.

29. The method of claim 8 wherein the pharmaceutical composition further comprises a taxane compound.

30. The method of claim 29 wherein the taxane compound is selected from paclitaxel, docetaxel, and taxotere.

31. The method of claim 8 wherein the pharmaceutical composition further comprises fludarabine.

32. The method of claim 8 wherein the pharmaceutical composition further comprises dacarbazine.

33. The method of claim 1 wherein C is a 5-methyl cytosine beta-D-oxy-LNA.

34. The method of claim 1 wherein C is a cytosine beta-D-oxy-LNA.

35. The method of claim 6 wherein C is a 5-methyl cytosine beta-D-oxy-LNA.

36. The method of claim 6 wherein C is a cytosine beta-D-oxy-LNA.

37. The method of claim 9 wherein C is a 5-methyl cytosine beta-D-oxy-LNA.

38. The method of claim 9 wherein C is a cytosine beta-D-oxy-LNA.

39. An oligomer consisting of 16-30 nucleotides joined by internucleoside linkages, the oligomer comprising: CTcccaacgtgcgCCa (SEQ NO: 15), wherein C is a 5-methyl cytosine beta-D-oxy-LNA or cytosine beta-D-oxy-LNA, T is a thymine beta-D-oxy LNA and a, c, g, and t are deoxyribonucleotides.

40. The oligomer of claim 39 wherein C is a 5-methyl cytosine beta-D-oxy-LNA.

41. The oligomer of claim 39 wherein C is a cytosine beta-D-oxy-LNA.

42. The oligomer of claim 39 wherein internucleotide linkages in the oligomer arc phosphorothioate groups.

43. An oligomer consisting of CTcccaacgtgcgCCa (SEQ NO: 15), wherein C is a 5-methyl cytosine beta-D-oxy-LNA or cytosine beta-D-oxy-LNA, T is a thymine beta-D-oxy LNA and a, c, g, and t are deoxyribonucleotides.

44. The oligomer of claim 43 wherein C is a 5-methyl cytosine beta-D-oxy-LNA.

45. The oligomer of claim 43 wherein C is a cytosine beta-D-oxy-LNA.

46. The oligomer of claim 43 wherein internucleoside linkages in the oligomer are phosphorothioate groups.

47. A pharmaceutical composition comprising the oligomer of claim 39 or claim 43 and a pharmaceutically acceptable carrier.

48. A pharmaceutical composition comprising the oligomer of claim 40 and a pharmaceutically acceptable carrier.

49. A pharmaceutical composition comprising the oligomer of claim 44 and a pharmaceutically acceptable carrier.

50. The pharmaceutical composition of claim 47, wherein the pharmaceutical composition further comprises a chemotherapeutic compound.

51. The pharmaceutical composition of claim 47, wherein the pharmaceutical composition further comprises a taxane compound.

52. The pharmaceutical composition according to claim 51 wherein the taxane compound is selected from paclitaxel, docetaxel, and taxotere.

53. The pharmaceutical composition of claim 47, wherein the pharmaceutical composition further comprises fludarabine.

54. The pharmaceutical composition of claim 47, wherein the pharmaceutical composition further comprises dacarbazine.

55. The method of claim 1 wherein the oligomer consists of CTcccaacgtgcgCCa (SEQ ID NO: 15).

56. The method of claim 6 wherein the oligomer consists of CTcccaacgtgcgCCa (SEQ ID NO: 15).

57. The method of claim 9 wherein the oligomer consists of CTcccaacgtgcgCCa (SEQ ID NO: 15).

* * * * *

UNITED STATES PATENT AND TRADEMARK OFFICE
CERTIFICATE OF CORRECTION

PATENT NO. : 7,622,453 B2
APPLICATION NO. : 11/021729
DATED : November 24, 2009
INVENTOR(S) : Frieden et al.

It is certified that error appears in the above-identified patent and that said Letters Patent is hereby corrected as shown below:

On the Title Page, Column 1, line 5 Item (75) delete "Residence Not Provided (DK)" and insert -- Copenhagen K (DK) --

On the Title Page, Column 2, line 16 delete "264." and insert -- 264, --

In Column 104, line 49 delete "A." and insert -- A --

In Column 104, line 49 delete "from," and insert -- from --

In Column 106, line 20 delete "arc" and insert -- are --

Signed and Sealed this

Nineteenth Day of January, 2010

David J. Kappos
*Director of the United States Patent and Trademark Office*

UNITED STATES PATENT AND TRADEMARK OFFICE
CERTIFICATE OF CORRECTION

PATENT NO.        : 7,622,453 B2                                             Page 1 of 1
APPLICATION NO.   : 11/021729
DATED             : November 24, 2009
INVENTOR(S)       : Frieden et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 464 days.

Signed and Sealed this

Fourteenth Day of December, 2010

David J. Kappos
*Director of the United States Patent and Trademark Office*